United States Patent
Hayashi et al.

(10) Patent No.: US 8,083,810 B2
(45) Date of Patent: Dec. 27, 2011

(54) AZO COMPOUND, AZO PIGMENT, DISPERSION CONTAINING THE AZO COMPOUND OR AZO PIGMENT, COLORING COMPOSITION, INK FOR INKJET RECORDING, INK TANK FOR INKJET RECORDING, INKJET RECORDING METHOD AND RECORDED MATERIAL

(75) Inventors: Shinya Hayashi, Fujinomiya (JP); Keiichi Tateishi, Fujinomiya (JP); Naoyuki Hanaki, Odawara (JP)

(73) Assignee: Fujifilm Corporation, Tokyo (JP)

( * ) Notice: Subject to any disclaimer, the term of this patent is extended or adjusted under 35 U.S.C. 154(b) by 0 days.

(21) Appl. No.: 12/921,309

(22) PCT Filed: Mar. 5, 2009

(86) PCT No.: PCT/JP2009/054179
§ 371 (c)(1),
(2), (4) Date: Sep. 7, 2010

(87) PCT Pub. No.: WO2009/110556
PCT Pub. Date: Sep. 11, 2009

(65) Prior Publication Data
US 2011/0001777 A1  Jan. 6, 2011

(30) Foreign Application Priority Data

Mar. 7, 2008 (JP) .................. 2008-058713
Feb. 6, 2009 (JP) .................. 2009-026195

(51) Int. Cl.
*A61Q 5/10* (2006.01)
*C09D 11/00* (2006.01)
(52) U.S. Cl. ...... 8/637.1; 8/639; 8/690; 8/692; 106/31.6
(58) Field of Classification Search .................. 8/637.1, 8/639, 690, 692; 106/31.6
See application file for complete search history.

(56) References Cited

U.S. PATENT DOCUMENTS
2,936,306 A    5/1960   Schmid et al.
(Continued)

FOREIGN PATENT DOCUMENTS
EP    1 906 401 A2    4/2008
(Continued)

OTHER PUBLICATIONS
STIC Search Report dated Jun. 9, 2011.*
(Continued)

*Primary Examiner* — Eisa Elhilo
(74) *Attorney, Agent, or Firm* — Sughrue Mion, PLLC

(57) ABSTRACT

To provide an azo pigment excellent in coloristic characteristics such as tinctorial strength and hue and at the same time, excellent in the durability such as light fastness and ozone resistance, a pigment dispersion containing the azo pigment, a coloring composition, and an ink for inkjet recording. An azo pigment represented by the following formula (1), its tautomer, or a salt or hydrate thereof:

Formula (1):

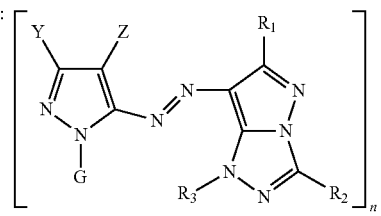

(wherein $R_1$, $R_2$, $R_3$, Y, Z and G each independently represents a hydrogen atom or a substituent; n represents and integer of 2 to 4; and the formula represents a dimer through $R_1$, $R_2$, $R_3$, Y, Z or G when n is 2, represents a trimer through $R_1$, $R_2$, $R_3$, Y, Z or G when n is 3, and represents a tetramer through $R_1$, $R_2$, $R_3$, Y, Z or G when n is 4).

17 Claims, 1 Drawing Sheet

U.S. PATENT DOCUMENTS

| | | | |
|---|---|---|---|
| 4,870,164 A | | 9/1989 | Kuhne et al. |
| 2005/0126431 A1 | | 6/2005 | Potenza et al. |
| 2008/0012930 A1 | * | 1/2008 | Fujie et al. ............ 347/217 |

FOREIGN PATENT DOCUMENTS

| | | |
|---|---|---|
| JP | 56-38354 A | 4/1981 |
| JP | 11-100519 A | 4/1999 |
| JP | 2003-277662 A | 10/2003 |
| JP | 2005-162812 A | 6/2005 |
| JP | 2005-220217 A | 8/2005 |
| JP | 2008-007732 A | 1/2008 |

OTHER PUBLICATIONS

International Search Report dated Jun. 2, 2009, 3 pages (for Int'l Application No. PCT/JP2009/054179).

Written Opinion (PCT/ISA/237) for PCT/JP2009/054179, dated Jun. 2, 2009.

Supplementary Extended European Search Report dated Oct. 4, 2011 in European Application No. 09717322.3.

* cited by examiner

US 8,083,810 B2

AZO COMPOUND, AZO PIGMENT, DISPERSION CONTAINING THE AZO COMPOUND OR AZO PIGMENT, COLORING COMPOSITION, INK FOR INKJET RECORDING, INK TANK FOR INKJET RECORDING, INKJET RECORDING METHOD AND RECORDED MATERIAL

TECHNICAL FIELD

The present invention relates to an azo compound, an azo pigment, a dispersion containing the azo compound or azo pigment, a coloring composition, an ink for inkjet recording, an ink tank for inkjet recording, an inkjet recording method and a recorded material.

BACKGROUND ART

In recent years, a material for forming particularly a color image is predominating as an image recording material. Specifically, an inkjet recording material, a heat-sensitive transfer recording material, an electrophotographic recording material, a transfer silver halide light-sensitive material, a printing ink, a recording pen and the like are popularly used. Also, a color filter for recording and reproducing a color image is used, in the case of the filming equipment, in an imaging device such as CCD and, in the case of the display, in LCD or PDP. In these color image recording materials and color filters, colorants (dyes or pigments) of three primary colors by a so-called additive or subtractive color mixing method are used for displaying or recording a full color image, but a colorant having absorption characteristics capable of realizing a preferred color reproduction region and having fastness high enough to endure various use conditions and environmental conditions is not found at present, and improvements are keenly demanded.

The dyes and pigments used in the above-described applications are commonly required to have the following properties. For example, it is required to have good absorption characteristics in terms of color reproduction and show good fastness to usage environment conditions, such as light resistance, heat resistance and resistance to an oxidative gas such as ozone. In addition, in the case where the colorant is a pigment, the requisite properties further include, for example, being substantially insoluble in water or an organic solvent, showing good chemical resistance, and not impairing the preferred absorption characteristics in the molecular dispersion state even when used as a particle. These requisite characteristics can be controlled by the degree of the intermolecular interaction, but absorption characteristics and fastness are in a trade-off relationship and therefore, it is difficult to satisfy both at the same time. In using a pigment, other than the properties described above, it is also required, for example, to have a particle size and a particle shape necessary for bringing out the desired transparency, to show good fastness to usage environment conditions, such as light fastness, heat resistance, resistance to an oxidative gas such as ozone, and chemical resistance to an organic solvent, a sulfurous acid gas or the like, and to be capable of dispersing even into a microparticle in the medium used and keeping stable the dispersed state. Above all, a pigment having good yellow hue and high resistance to light, wet heat and environmental active gases, in particular, a pigment having high tinctorial strength and being fast to light, is strongly demanded.

More specifically, the performance required of the pigment is diversified as compared with the dye that is required to have performances as a colorant molecule, and not only performances as a colorant molecule but also all of the above-described requisite performances as a solid (fine particle dispersion) resulting from aggregation of colorant molecules must be satisfied. In turn, the compound group usable as a pigment is extremely limited as compared with the dye and even when a pigment is derived from a high-performance dye, the pigment capable of satisfying the requisite performances as a fine particle dispersion is very few in number and cannot be easily developed. This can be confirmed also by the fact that the number of pigments registered in the Color Index is less than 1/10 of the number of dyes.

Azo pigments are widely used in a printing ink, an inkjet ink, an electrophotographic material and the like because of their excellent coloristic characteristics, i.e., hue and tinctorial strength. Of these, a diarylide pigment is most typically used as a yellow azo dye. Examples of the diarylide pigment include C.I. Pigment Yellow 12, C.I. Pigment Yellow 13 and C.I. Pigment Yellow 17. However, the diarylide pigment is very poor in the fastness, particularly light fastness, and when the printed material is exposed to light, the pigment is decomposed to cause fading. Thus, this pigment is not suitable for storage of the printed material for a long period of time.

In order to overcome such a defect, an azo pigment improved in the fastness by increasing the molecular weight or introducing a group having strong intermolecular interaction is disclosed (see, for example, Patent Documents 1 to 3). However, even the improved pigment is still insufficient, though the light fastness of the pigment described, for example, in Patent Document 1 is improved. Also, the pigments described, for example, in Patent Documents 2 to 3 bring about green tinting in the hue and decrease in the tinctorial strength and disadvantageously suffer from poor coloristic characteristics.

In Patent Documents 4, 5 and 6, colorants having excellent absorption characteristics for color reproduction and sufficiently high fastness are disclosed. However, all of specific compounds described in these patent documents dissolve in water or an organic solvent and are insufficient in the chemical resistance.

In the case of reproducing a full color by a primary color mixing method using three colors of yellow, magenta and cyan or four colors with the addition of black, when a pigment poor in the fastness is used as the pigment for yellow, the gray balance of the printed material is changed with the passage of time, and when a pigment poor in the coloristic characteristics is used, the color reproducibility at the printing is decreased. Accordingly, for obtaining a printed material capable of maintaining high color reproducibility for a long period of time, a yellow pigment or pigment dispersion satisfying both coloristic characteristics and fastness is demanded.

Patent Document 1: JP-A-56-38354 (the term "JP-A" as used herein means an "unexamined published Japanese patent application")
Patent Document 2: U.S. Pat. No. 2,936,306
Patent Document 3: JP-A-11-100519
Patent Document 4: JP-A-2003-277662
Patent Document 5: JP-A-2005-220217
Patent Document 6: JP-A-2008-7732

DISCLOSURE OF THE INVENTION

Problems that the Invention is to Solve

An object of the present invention is to provide an azo compound, an azo pigment, which are excellent in coloristic characteristics such as tinctorial strength and hue and at the same time, excellent in the durability such as light fastness and ozone resistance, a dispersion containing the azo compound or azo pigment, a coloring composition, an ink for inkjet recording, an ink tank for inkjet recording using the ink, an inkjet recording method, and a recorded material excellent in the coloristic characteristics and durability.

Means for Solving the Problems

Under these circumstances, the present inventors have made intensive studies, as a result, a novel azo pigment has been discovered and this pigment has been found to be an excellent pigment capable of satisfying both coloristic characteristics and durability. The present invention has been accomplished based on these findings.

That is, the present invention includes the followings.

[1] An azo pigment represented by the following formula (1), its tautomer, or a salt or hydrate thereof:

Formula (1):

[Chem. 1]

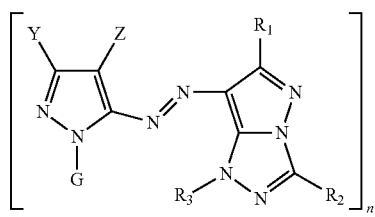

(wherein $R_1$, $R_2$, $R_3$, Y, Z and G each independently represents a hydrogen atom or a substituent; n represents and integer of 2 to 4; and the formula represents a dimer through $R_1$, $R_2$, $R_3$, Y, Z or G when n is 2, represents a trimer through $R_1$, $R_2$, $R_3$, Y, Z or G when n is 3, and represents a tetramer through $R_1$, $R_2$, $R_3$, Y, Z or G when n is 4).

[2] An azo pigment represented by the following formula (2), its tautomer, or a salt or hydrate thereof:

Formula (2):

[Chem. 2]

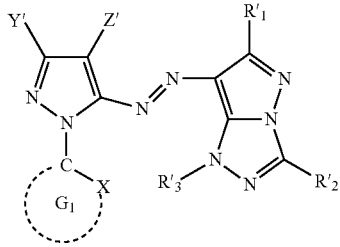

(wherein $R'_1$, $R'_2$ and Y' each independently represents a hydrogen atom, a linear or branched alkyl group having a carbon number of 1 to 4, an alkenyl group having a carbon number of 2 to 4, an alkynyl group having a carbon number of 2 to 4, an acyl group having a carbon number of 1 to 5, an aralkyl group having a carbon number of 7 to 9, a 5- to 8-membered saturated or unsaturated hydrocarbon ring group, or a 5- to 8-membered saturated or unsaturated heterocyclic group; $R'_3$ represents a hydrogen atom or a monovalent substituent; Z' represents an electron-withdrawing group having a Hammett's σp value of 0.2 or more; X represents a heteroatom at the position adjacent to the carbon atom bonded to the pyrazole ring; $G_1$ represents an atomic group for forming a 5- to 8-membered saturated or unsaturated heterocyclic ring; when any one of $R'_1$, $R'_2$, $R'_3$, Y' and $G_1$ represents a 5- to 8-membered saturated or unsaturated heterocyclic ring, the ring is a monocyclic ring or a condensed ring; and when any one of $R'_1$, $R'_2$, $R'_3$, Y' and $G_1$ represents a 5-membered unsaturated heterocyclic ring, the ring contains two or more nitrogen atoms therein).

[3] The azo pigment, its tautomer or a salt or hydrate thereof as described in [2], wherein X in formula (2) is a nitrogen atom.

[4] The azo pigment, its tautomer or a salt or hydrate thereof as described in [2], wherein $G_1$ in formula (2) is any one selected from the group of substituents represented by the following formula (3)-1 to (3)-6:

Formula (3):

[Chem. 3]

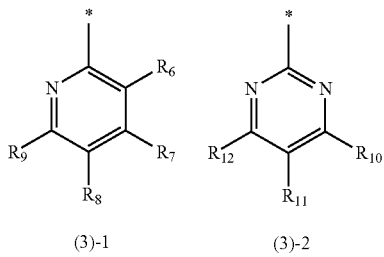

(3)-1     (3)-2

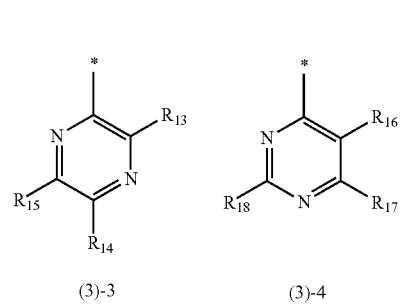

(3)-3     (3)-4

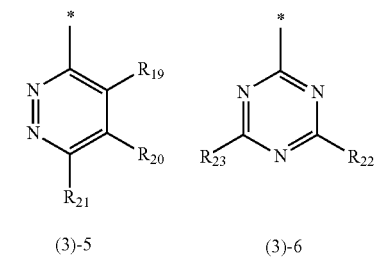

(3)-5     (3)-6

(wherein $R_6$ to $R_{23}$ each independently represents a hydrogen atom or a substituent, and $R_6$ to $R_{21}$ may combine with each other to form a ring).

[5] The azo pigment, its tautomer or a salt or hydrate thereof as described in [1], wherein the azo pigment represented by formula (1) is an azo pigment represented by the following formula (4):

Formula (4):

[Chem. 4]

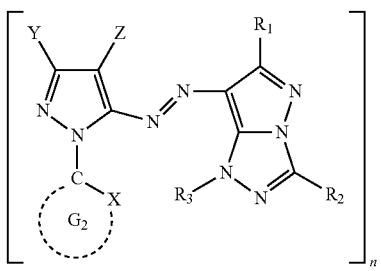

(wherein n, $R_1$, $R_2$, $R_3$, Y and Z each independently has the same meaning as n, $R_1$, $R_2$, $R_3$, Y or Z in formula (1); X represents a heteroatom at the position adjacent to the carbon atom bonded to the pyrazole ring; $G_2$ represents an atomic group for forming a 5- to 8-membered saturated or unsaturated heterocyclic ring; the formula represents a dimer through $R_1$, $R_2$, $R_3$, Y, Z or $G_2$ when n is 2, represents a trimer through $R_1$, $R_2$, $R_3$, Y, Z or $G_2$ when n is 3, and represents a tetramer through $R_1$, $R_2$, $R_3$, Y, Z or $G_2$ when n is 4; and when any one of $R_1$, $R_2$, $R_3$, Y and $G_2$ represents a 5- to 8-membered saturated or unsaturated heterocyclic ring, the ring is a monocyclic ring or a condensed ring).

[6] The azo pigment, its tautomer or a salt or hydrate thereof as described in [5], wherein X in formula (4) is a nitrogen atom.

[7] The azo pigment, its tautomer or a salt or hydrate thereof as described in [5] or [6], wherein $G_2$ in formula (4) is any one group selected from the group of monovalent to trivalent substituents represented by (3)-1 to (3)-6 in the following formula (3):

Formula (3):

[Chem. 5]

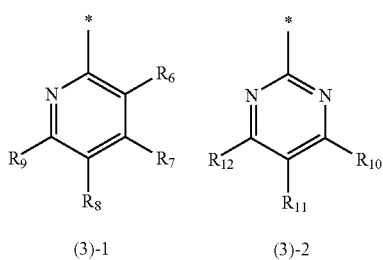

(3)-1      (3)-2

-continued

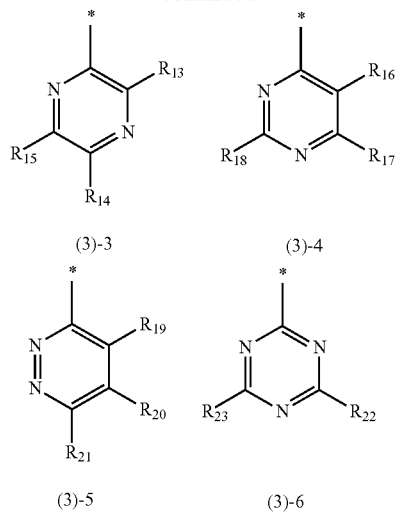

(3)-3      (3)-4

(3)-5      (3)-6

(wherein $R_6$ to $R_{23}$ each independently represents a hydrogen atom or a substituent, and $R_6$ to $R_{21}$ may combine with each other to form a ring).

[8] An azo compound represented by the following formula (2):

Formula (2):

[Chem. 6]

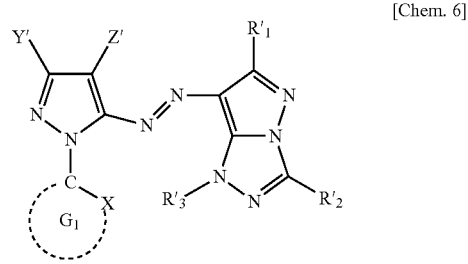

(wherein $R'_1$, $R'_2$ and Y' each independently represents a hydrogen atom, a linear or branched alkyl group having a carbon number of 1 to 4, an alkenyl group having a carbon number of 2 to 4, an alkynyl group having a carbon number of 2 to 4, an acyl group having a carbon number of 1 to 5, an aralkyl group having a carbon number of 7 to 9, a 5- to 8-membered saturated or unsaturated hydrocarbon ring group, or a 5- to 8-membered saturated or unsaturated heterocyclic group; $R'_3$ represents a hydrogen atom or a monovalent substituent; Z' represents an electron-withdrawing group having a Hammett's σp value of 0.2 or more; X represents a heteroatom at the position adjacent to the carbon atom bonded to the pyrazole ring; $G_1$ represents an atomic group for forming a 5- to 8-membered saturated or unsaturated heterocyclic ring; when any one of $R'_1$, $R'_2$, $R'_3$, Y' and $G_1$ represents a 5- to 8-membered saturated or unsaturated heterocyclic ring, the ring is a monocyclic ring or a condensed ring; and when any one of $R'_1$, $R'_2$, $R'_3$, Y' and $G_1$ represents a 5-membered unsaturated heterocyclic ring, the ring contains two or more nitrogen atoms therein).

[9] The azo compound as described in [8], wherein $G_1$ in formula (2) is any one selected from the group of substituents represented by the following formula (3)-1 to (3)-6:

Formula (3): [Chem. 7]

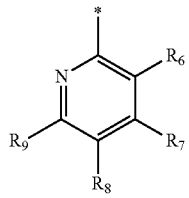

(3)-1

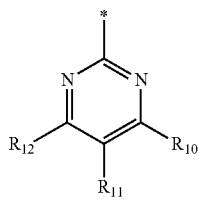

(3)-2

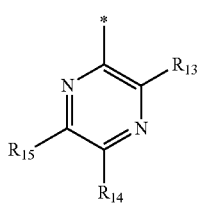

(3)-3

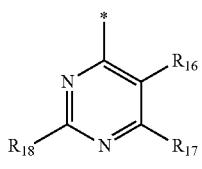

(3)-4

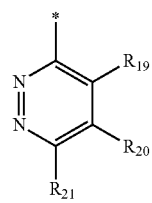

(3)-5

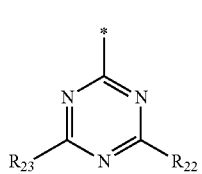

(3)-6

(wherein $R_6$ to $R_{23}$ each independently represents a hydrogen atom or a substituent, and $R_6$ to $R_{21}$ may combine with each other to form a ring).

[10] An azo compound represented by the following formula (4):

Formula (4): [Chem. 8]

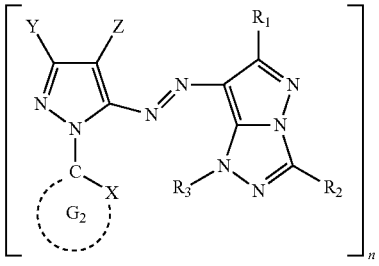

(wherein $R_1$, $R_2$, $R_3$, Y and Z each independently represents a hydrogen atom or a substituent; n represents an integer of 2 to 4; X represents a heteroatom at the position adjacent to the carbon atom bonded to the pyrazole ring; $G_2$ represents an atomic group for forming a 5- to 8-membered saturated or unsaturated heterocyclic ring; the formula represents a dimer through $R_1$, $R_2$, $R_3$, Y, Z or $G_2$ when n is 2, represents a trimer through $R_1$, $R_2$, $R_3$, Y, Z or $G_2$ when n is 3, and represents a tetramer through $R_1$, $R_2$, $R_3$, Y, Z or $G_2$ when n is 4; and when any one of $R_1$, $R_2$, $R_3$, Y and $G_2$ represents a 5- to 8-membered saturated or unsaturated heterocyclic ring, the ring is a monocyclic ring or a condensed ring).

[11] The azo compound as described in [10], wherein $G_2$ in formula (4) is any one group selected from the group of monovalent to trivalent substituents represented by (3)-1 to (3)-6 in the following formula (3):

Formula (3): [Chem. 9]

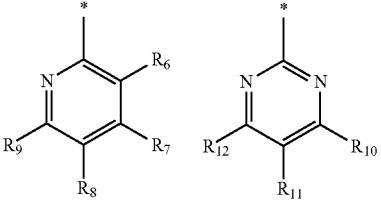

(3)-1    (3)-2

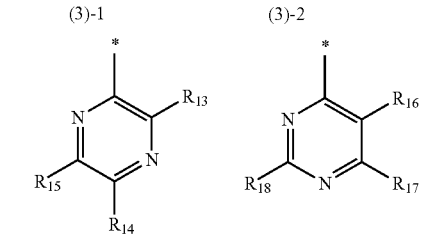

(3)-3    (3)-4

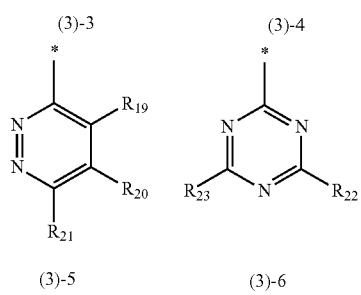

(3)-5    (3)-6

(wherein $R_6$ to $R_{23}$ each independently represents a hydrogen atom or a substituent, and $R_6$ to $R_{21}$ may combine with each other to form a ring).

[12] A dispersion comprising at least one member of the azo pigment, its tautomer or a salt or hydrate thereof described in any one of [1] to [7] and the azo compound described in any one of [8] to [11].
[13] A coloring composition comprising the dispersion described in [12].
[14] An ink for inkjet recording, comprising the dispersion described in [12].
[15] An ink tank for inkjet recording, comprising the ink for inkjet recording described in [14].
[16] An inkjet recording method, using the ink for inkjet recording described in [14].
[17] A recorded material obtained using the ink for inkjet recording described in [14].

ADVANTAGE OF THE INVENTION

According to the present invention, an azo pigment exhibiting good performance in coloristic characteristics such as tinctorial strength and hue and in the durability such as ozone resistance, particularly excellent in the light fastness and dispersibility, is provided. By using the pigment of the present invention, a pigment dispersion excellent in coloristic characteristics, durability and dispersion stability is provided. Also, according to the present invention, a coloring composition and an ink for inkjet recording, each containing the azo pigment and being excellent in the coloristic characteristics such as tinctorial strength and hue and at the same time, excellent in the light fastness and dispersibility, are obtained. The pigment dispersion can be used, for example, in an ink for printing such as inkjet recording, a color toner for electrophotography, a color filter for a display such as LCD and PDP or an imaging device such as CCD, a coating material, and a colored plastic.

BEST MODE FOR CARRYING OUT THE INVENTION

Figure 1:
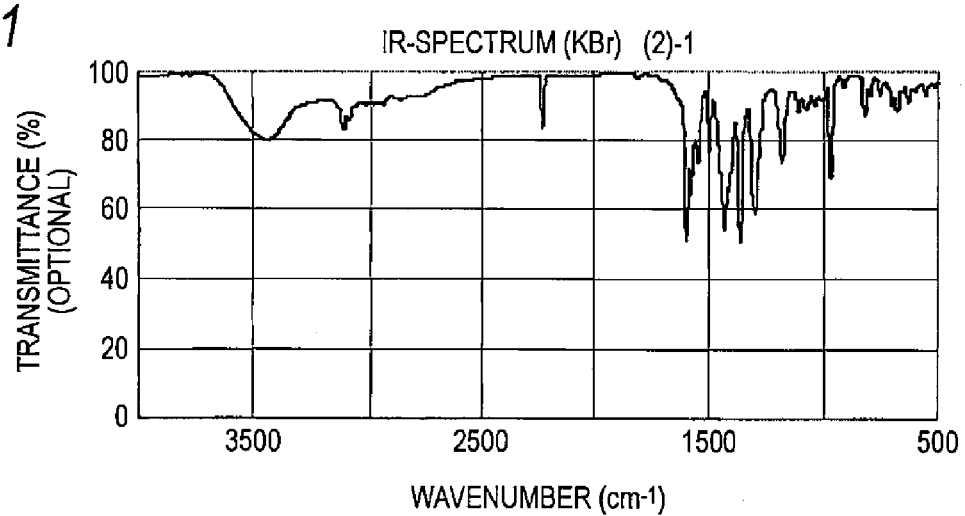
FIG. 1 The infrared absorption spectrum of Azo Pigment (2)-1 obtained in Example 2.

The present invention is described in detail below.
Here, the Hammett's substituent constant σp value used in the present invention is described briefly.
The Hammett's rule is an empirical rule advocated by L. P. Hammett in 1935 so as to quantitatively discuss the effect of substituent on the reaction or equilibrium of benzene derivatives and its propriety is widely admitted at present. The substituent constant determined by the Hammett's rule includes a σp value and a σm value and these values can be found in a large number of general publications and described in detail, for example, in J. A. Dean (compiler), *Lange's Handbook of Chemistry*, 12th ed., McGraw-Hill (1979), and *Kagakuno Ryoiki* (*Chemistry Region*), special number, No. 122, pp. 96-103, Nankodo (1979). In the present invention, each substituent is limited or described by using the Hammett's substituent constant σp but this does not mean that the substituent is limited only to those having a known value which can be found in the above-described publications. Needless to say, the substituent includes substituents whose σp value is not known in the publications but when measured based on the Hammett's rule, falls within the range specified. The compounds represented by formulae (1), (2), (4) and (5) of the present invention are not a benzene derivative, but the σp value is used as a measure for showing the electron effect of the substituent irrespective of the substitution site. In the present invention, the σp value is used in this meaning.

[Azo Pigment]

A pigment is in a state where molecules are firmly bonded to each other by an aggregation energy due to a strong interaction between colorant molecules. It is described, for example, in *Journal of the Imaging Society of Japan*, Vol. 43, page 10 (2004) that creation of this state requires an intermolecular van der Waals force or an intermolecular hydrogen bonding.

For strengthening the intermolecular van der Waals force, introduction or the like of an aromatic group, a polar group and/or a heteroatom into the molecule may be considered, and in order to form an intermolecular hydrogen bonding, for example, introduction of a substituent containing a hydrogen atom bonded to a heteroatom and/or introduction of an electron-donating substituent may be considered. Furthermore, the polarity of the entire molecule is supposed to be preferably higher. This implies, for example, that the chain group such as alkyl group is preferably shorter and the molecular weight/the value of azo group are preferably smaller.

From these viewpoints, the pigment molecule preferably contains an amide bond, a sulfonamide bond, an ether bond, a sulfone group, an oxycarbonyl group, an imide group, a carbamoylamino group, a heterocyclic ring, a benzene ring or the like.

The azo pigment of the present invention is represented by formula (1). Thanks to its specific structure, the compound represented by formula (1) can be an azo pigment that readily forms an intermolecular interaction of colorant molecules and shows low solubility in water, an organic solvent or the like.

Unlike the dye that is used by dissolving it in a molecular dispersion state in water, an organic solvent or the like, the pigment is used by finely dispersing it as a solid particle such as molecular aggregate in a solvent.

The azo pigment represented by formula (1), and a tautomer, a crystalline polymorph, a salt and a complex thereof are described in detail below.

Formula (1):

[Chem. 10]

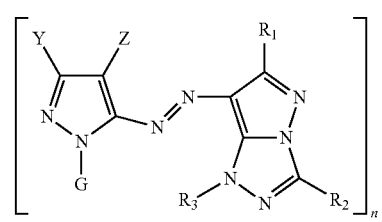

(wherein $R_1$, $R_2$, $R_3$, Y, Z and G each independently represents a hydrogen atom or a substituent; n represents and integer of 2 to 4; and the formula represents a dimer through $R_1$, $R_2$, $R_3$, Y, Z or G when n is 2, represents a trimer through $R_1$, $R_2$, $R_3$, Y, Z or G when n is 3, and represents a tetramer through $R_1$, $R_2$, $R_3$, Y, Z or G when n is 4.)

Formula (1) is described in detail below.
In formula (1), n represents an integer of 2 to 4 and is preferably 2 or 3, more preferably 2.

When n is 2 or more, the molecular weight becomes large, and the intermolecular interaction such as π-π stacking between molecules is more strengthened. The tight intermolecular interaction enhances the solvent resistance. Furthermore, the tight intermolecular interaction and the increase in crystallinity readily allow for the occurrence of energy relaxation due to lattice vibration or the like, and the light fastness is enhanced. If n exceeds 4, the molecular weight becomes large, but the molecule can hardly keep the planarity due to steric hindrance, as a result, the intermolecular interaction is weakened and the light fastness or solvent resistance tends to decrease.

$R_1$, $R_2$, $R_3$, Y, Z and G may have a substituent.

In formula (1), the group represented by $R_1$, $R_2$, $R_3$, Y, Z and G includes a hydrogen atom, a linear or branched alkyl group having a carbon number of 1 to 6, a linear or branched aralkyl group having a carbon number of 7 to 12, a linear or branched alkenyl group having a carbon number of 2 to 6, a linear or branched alkynyl group having a carbon number of 2 to 6, a cycloalkyl group having a carbon number of 3 to 6, a cycloalkenyl group having a carbon number of 3 to 10 (e.g., methyl, ethyl, n-propyl, i-propyl, n-butyl, i-butyl, sec-butyl, tert-butyl, 2-ethylhexyl, 2-methylsulfonylethyl, 3-phenoxypropyl, trifluoromethyl, cyclopentyl), a halogen atom (e.g., fluorine, chlorine, bromine), an aryl group (e.g., phenyl, 4-tert-butylphenyl, 2,4-di-tert-amylphenyl, 4-acetamidophenyl), a heterocyclic group (e.g., imidazolyl, pyrazolyl, triazolyl, 2-furyl, 2-thienyl, 2-pyridinyl, 2-pyrimidinyl, 2-benzothiazolyl), a cyano group, a hydroxyl group, a nitro group, a carboxy group, an amino group, an alkyloxy group (e.g., methoxy, ethoxy, 2-methoxyethoxy, 2-methylsulfonylethoxy), an aryloxy group (e.g., phenoxy, 2-methylphenoxy, 4-tert-butylphenoxy, 3-nitrophenoxy, 3-tert-butyloxycarbonylphenoxy, 3-methoxycarbonylphenyloxy), an acylamino group (e.g., acetamido, benzamido, 4-(3-tert-butyl-4-hydroxyphenoxy)butanamido), an alkylamino group (e.g., methylamino, butylamino, diethylamino, methylbutylamino), an arylamino group (e.g., phenylamino, 2-chloroanilino), a ureido group (e.g., phenylureido, methylureido, N,N-dibutylureido), a sulfamoylamino group (e.g., N,N-dipropylsulfamoylamino), an alkylthio group (e.g., methylthio, octylthio, 2-phenoxyethylthio), an arylthio group (e.g., phenylthio, 2-butoxy-5-tert-octylphenylthio, 2-carboxyphenylthio), an alkyloxycarbonylamino group (e.g., methoxycarbonylamino), alkylsulfonylamino and arylsulfonylamino groups (e.g., methylsulfonylamino, phenylsulfonylamino, p-toluenesulfonylamino), a carbamoyl group (e.g., carbamoyl, N-ethylcarbamoyl, N,N-dibutylcarbamoyl), a sulfamoyl group (e.g., N-ethylsulfamoyl, N,N-dipropylsulfamoyl, N-phenylsulfamoyl), a sulfonyl group (e.g., methylsulfonyl, phenylsulfonyl, p-toluenesulfonyl), an alkyloxycarbonyl group (e.g., methoxycarbonyl, ethoxycarbonyl), a heterocyclic oxy group (e.g., 1-phenyltetrazol-5-oxy, 2-tetrahydropyranyloxy), an azo group (e.g., phenylazo, 4-methoxyphenylazo, 4-pivaloylaminophenylazo, 2-hydroxy-4-propanoylphenylazo), an acyloxy group (e.g., acetoxy), a carbamoyloxy group (e.g., N-methylcarbamoyloxy, N-phenylcarbamoyloxy), a silyloxy group (e.g., trimethylsilyloxy, dibutylmethylsilyloxy), an aryloxycarbonylamino group (e.g., phenoxycarbonylamino), an imido group (e.g., N-succinimido, N-phthalimido), a heterocyclic thio group (e.g., 2-benzothiazolylthio, 2,4-di-phenoxy-1,3,5-triazole-6-thio, 2-pyridylthio), a sulfinyl group (e.g., 3-phenoxypropylsulfinyl), a phosphonyl group (e.g., phenoxyphosphonyl, octyloxyphosphonyl, phenylphosphonyl), an aryloxycarbonyl group (e.g., phenoxycarbonyl), an acyl group (e.g., acetyl, 3-phenylpropanoyl, benzoyl), and an ionic hydrophilic group (e.g., carboxyl, sulfo, phosphono, quaternary ammonium).

In the case where the azo pigment of the present invention contains an ionic hydrophilic group as the substituent, a salt with a polyvalent metal cation (for example, magnesium ion, calcium ion or barium ion) is preferred. In particular, a lake pigment is preferred.

In formula (1), $R_1$ and $R_2$ each is independently, preferably a hydrogen atom, a linear or branched alkyl group having a carbon number of 1 to 6, a linear or branched alkenyl group having a carbon number of 2 to 6, a linear or branched alkynyl group having a carbon number of 2 to 6, an aralkyl group having a carbon number of 7 to 9, a substituted or unsubstituted 5- to 8-membered aryl group or a substituted or unsubstituted 5- to 8-membered heterocyclic group, more preferably a hydrogen atom, a linear or branched alkyl group having a carbon number of 1 to 4 or a substituted or unsubstituted 5- to 8-membered aryl group, and most preferably a linear or branched alkyl group having a carbon number of 1 to 4 or a substituted or unsubstituted 5- or 6-membered aryl group.

In formula (1), the monovalent substituent represented by $R_3$ includes a linear or branched alkyl group having a carbon number of 1 to 6 (e.g., methyl, ethyl, n-propyl, i-propyl, n-butyl, i-butyl, sec-butyl, tert-butyl, 2-ethylhexyl, 2-methylsulfonylethyl, 3-phenoxypropyl, trifluoromethyl), an aralkyl group having a carbon number of 7 to 12 (e.g., benzyl, 4-aminophenylmethyl), a linear or branched alkenyl group having a carbon number of 2 to 6 (e.g., ethenyl, 1-propenyl, 1,3-butanedienyl), a linear or branched alkynyl group having a carbon number of 2 to 6 (e.g., ethynyl, 1-propynyl, 1-butynyl), a cycloalkyl group having a carbon number of 3 to 6 (e.g., cyclopentyl), a cycloalkenyl group having a carbon number of 3 to 10 (e.g., cyclohexenyl, cyclohexanedienyl), an aryl group (e.g., phenyl, 4-tert-butylphenyl, 2,4-di-tert-amylphenyl), a heterocyclic group (e.g., imidazolyl, pyrazolyl, triazolyl, 2-furyl, 2-thienyl, 2-pyrimidinyl, 2-benzothiazolyl), an alkyloxycarbonyl group (e.g., methoxycarbonyl, butyloxycarbonyl), an aryloxycarbonyl group (e.g., phenoxycarbonyl) and an acyl group (e.g., acetyl, 3-phenylpropanoyl, benzoyl).

Preferred examples of $R_3$ include a hydrogen atom, a linear or branched alkyl group having a carbon number of 1 to 4 (e.g., methyl, ethyl, n-propyl, i-propyl, n-butyl, i-butyl, sec-butyl, tert-butyl), an alkenyl group having a carbon number of 2 to 4 (e.g., ethenyl) and an alkynyl group having a carbon number of 2 to 4 (e.g., ethynyl).

$R_3$ is more preferably a hydrogen atom, a methyl group, an ethyl group, an ethenyl group or an ethynyl group, still more preferably a hydrogen atom.

Preferred examples of Y include a hydrogen atom, a linear or branched alkyl group having a carbon number of 1 to 6, a linear or branched alkenyl group having a carbon number of 2 to 6, a linear or branched alkynyl group having a carbon number of 2 to 6, a carbamoyl group having a carbon number of 1 to 6, an alkoxycarbonyl group having a carbon number of 1 to 6, a substituted or unsubstituted 5- to 8-membered aryl group and a substituted or unsubstituted 5- to 8-membered heterocyclic group. Y is more preferably a hydrogen atom, a linear or branched alkyl group having a carbon number of 1 to 4, a carbamoyl group having a carbon number of 1 to 4, an alkoxycarbonyl group having a carbon number of 1 to 5 or a substituted or unsubstituted 5- to 8-membered aryl group, still more preferably a hydrogen atom, a methyl group, a tert-butyl group or a substituted or unsubstituted 5- or 6-membered aryl group.

In formula (1), Z is preferably an electron-withdrawing group having a Hammett's substituent constant σp value of 0.2 or more, more preferably an electron-withdrawing group having a σp value of 0.3 or more. As for the upper limit, an electron-withdrawing group of 1.0 or less is preferred.

Specific examples of Z that is an electron-withdrawing group having a σp value of 0.2 or more include an acyl group, an acyloxy group, a carbamoyl group, an alkyloxycarbonyl group, an aryloxycarbonyl group, a cyano group, a nitro group, a dialkylphosphono group, a diarylphosphono group, a diaryl phosphinyl group, an alkylsulfinyl group, an arylsulfinyl group, an alkylsulfonyl group, an arylsulfonyl group, a sulfonyloxy group, an acylthio group, a sulfamoyl group, a thiocyanate group, a thiocarbonyl group, a halogenated alkyl group, a halogenated alkoxy group, a halogenated aryloxy group, a halogenated alkylamino group, a halogenated alkylthio group, an aryl group substituted with other electron-withdrawing group having a σp value of 0.2 or more, a heterocyclic group, a halogen atom, an azo group and a selenocyanate group.

Preferred examples of Z include an acyl group having a carbon number of 2 to 6, an acyloxy group having a carbon number of 2 to 6, a carbamoyl group having a carbon number of 1 to 8, an alkyloxycarbonyl group having a carbon number of 2 to 8, an aryloxycarbonyl group having a carbon number of 7 to 12, a cyano group, a nitro group, an alkylsulfinyl group having a carbon number of 1 to 6, an arylsulfinyl group having a carbon number of 6 to 10, an alkylsulfonyl group having a carbon number of 1 to 6, an arylsulfonyl group having a carbon number of 6 to 10, a sulfamoyl group having a carbon number of 0 to 9, a halogenated alkyl group having a carbon number of 1 to 6, a halogenated alkyloxy group having a carbon number of 1 to 6, a halogenated alkylthio group having a carbon number of 1 to 6, a halogenated aryloxy group having a carbon number of 6 to 12, an aryl group having a carbon number of 7 to 12 substituted with other two or more electron-withdrawing groups having a σp value of 0.2 or more, and a 5- to 8-membered heterocyclic group having a carbon number of 1 to 10 and containing a nitrogen atom, an oxygen atom or a sulfur atom.

Z is more preferably a cyano group, an alkyloxycarbonyl group having a carbon number of 2 to 8, an alkylsulfonyl group having a carbon number of 1 to 6, an arylsulfonyl group having a carbon number of 6 to 10 or a sulfamoyl group having a carbon number of 0 to 9, still more preferably a cyano group, an alkyloxycarbonyl group having a carbon number of 2 to 8, an alkylsulfonyl group having a carbon number of 1 to 4, an arylsulfonyl group having a carbon number of 6 to 8 or a sulfamoyl group having a carbon number of 0 to 8, and most preferably a cyano group.

In formula (1), preferred examples of G include a hydrogen atom, a linear or branched alkyl group, a cycloalkyl group, an acyl group, an alkenyl group, an alkynyl group, an aralkyl group, a 5- to 8-membered saturated or unsaturated hydrocarbon ring and a 5- to 8-membered saturated or unsaturated heterocyclic ring, and when G represents a 5- to 8-membered saturated or unsaturated hydrocarbon ring or heterocyclic ring, the ring is a monocyclic ring or a condensed ring. G may have a substituent. More preferred examples of G include a hydrogen atom, a linear or branched alkyl group having a carbon number of 1 to 6, an acyl group having a carbon number of 1 to 6, a 5- to 8-membered saturated or unsaturated hydrocarbon ring and a 5- to 8-membered saturated or unsaturated heterocyclic ring, and when G represents a 5- to 8-membered saturated or unsaturated hydrocarbon ring or heterocyclic ring, the ring is a monocyclic ring or a condensed ring. G may have a substituent. In particular, G is preferably a 5- to 8-membered substituted or unsubstituted aromatic hydrocarbon ring or a 5- to 8-membered substituted or unsubstituted heterocyclic group. When G represents a 5- to 8-membered substituted or unsubstituted aromatic hydrocarbon ring or a 5- to 8-membered substituted or unsubstituted heterocyclic group, the ring is a monocyclic ring or a condensed ring.

In formula (1), examples of the heterocyclic group represented by G include, as set forth without limiting the substitution position, a pyridyl group, a pyrazinyl group, a pyridazinyl group, a pyrimidinyl group, a triazinyl group, a quinolinyl group, an isoquinolinyl, a quinazolinyl group, a cinnolinyl group, a phthalazinyl group, a quinoxalinyl group, a pyrrolyl group, an indolyl group, a furanyl group, a benzofuranyl group, a thiophenyl group, a benzothiophenyl group, a pyrazolyl group, an imidazolyl group, a benzimidazolyl group, a triazolyl group, an oxazolyl group, a benzoxazolyl group, a thiazolyl group, a benzothiazolyl group, an isothiazolyl group, a benzisothiazolyl group, a thiadiazolyl group, an isoxazolyl group, a benzisoxazolyl group, a pyrrolidinyl group, a piperidinyl group, a piperazinyl group, an imidazolidinyl group, a thiazolinyl group and a sulfolanyl group.

Among these, a pyridyl group, a pyrazinyl group, a pyrimidinyl group, a pyridazinyl group and a triazinyl group are preferred, and a pyridyl group, a pyrimidinyl group and a triazinyl group are more preferred.

In the case where G is a group that can further have a substituent, examples of the substituent include the same groups as those described for $R_1, R_2, R_3, Y, Z$ and G in formula (1).

$R_1, R_2, R_3, Y$ and Z may further have a substituent, and examples of the substituent include the same substituents as those described for $R_1, R_2, R_3, Y, Z$ and G in formula (1).

In the case where $R_1, R_2, R_3, Y, Z$ and G each represents a divalent group, the divalent group is preferably an alkylene group (e.g., methylene, ethylene, propylene, butylene, pentylene), an alkenylene group (e.g., ethenylene, propenylene), an alkynylene group (e.g., ethynylene, propynylene), an arylene group (e.g., phenylene, naphthylene), a divalent heterocyclic group (e.g., 6-chloro-1,3,5-triazine-2,4-diyl, pyrimidine-2,4-diyl, pyrimidine-4,6-diyl, quinoxaline-2,3-diyl, pyridazine-3,6-diyl), —O—, —CO—, —NR'— (R' is a hydrogen atom, an alkyl group or an aryl group), —S—, —SO$_2$—, —SO— or a combination thereof (e.g., —NHCH$_2$CH$_2$NH—, —NHCONH—).

The alkylene group, the alkenylene group, the alkynylene group, the arylene group, the divalent heterocyclic group and the alkyl group or aryl group of R' may have a substituent.

Examples of the substituent include the same substituents as those described for $R_1, R_2, R_3, Y, Z$ and G in formula (1).

The alkyl group and aryl group of R' have the same meanings as the substituents described when $R_1, R_2, R_3, Y, Z$ and G in formula (1) each is an alkyl group or an aryl group.

The divalent group is more preferably an alkylene group having a carbon atom of 6 or less, an alkenylene group having a carbon number of 6 or less, an alkynylene group having a carbon number of 6 or less, an arylene group having a carbon number of 6 to 10, a divalent heterocyclic group, —S—, —SO—, —SO$_2$— or a combination thereof (e.g., —SCH$_2$CH$_2$S—, —SCH$_2$CH$_2$CH$_2$S—).

The total carbon number of the divalent linking group is preferably from 0 to 20, more preferably from 0 to 15, and most preferably from 0 to 10.

In the case where $R_1$, $R_2$, $R_3$, Y, Z and G each represents a trivalent group, the trivalent group is preferably a trivalent hydrocarbon group, a trivalent heterocyclic group, >N—, or a combination of this and a divalent group (e.g., >NCH$_2$CH$_2$NH—, >NCONH—).

The total carbon number of the trivalent linking group is preferably from 0 to 20, more preferably from 0 to 15, and most preferably from 0 to 10.

As for the combination of preferred groups in the pigment represented by formula (1) of the present invention, a compound where at least one of various groups is the above-described preferred group is preferred, a compound where a larger number of various groups are the above-described preferred groups is more preferred, and a compound where all groups are the above-described preferred groups is most preferred.

The particularly preferred combination as the azo pigment represented by formula (1) of the present invention includes the following (i) to (vi).

(i) n represents an integer of 2 to 4 and is preferably an integer of 2 to 3, more preferably 2.

(ii) $R_1$ and $R_2$ each is independently, preferably a hydrogen atom, a linear or branched alkyl group having a carbon number of 1 to 6, a linear or branched alkenyl group having a carbon number of 2 to 6, a linear or branched alkynyl group having a carbon number of 2 to 6, a substituted or unsubstituted 5- to 8-membered aryl group or a substituted or unsubstituted 5- to 8-membered heterocyclic group, more preferably a hydrogen atom, a linear or branched alkyl group having a carbon number of 1 to 4 or a substituted or unsubstituted 5- to 8-membered aryl group, still more preferably a linear or branched alkyl group having a carbon number of 1 to 4 or an unsubstituted 5- or 6-membered aryl group, yet still more preferably a linear or branched alkyl group having a carbon number of 1 to 4. The linear or branched alkyl group having a carbon number of 1 to 4 is preferably a methyl group or a tert-butyl group, more preferably a methyl group.

(iii) Y is preferably a hydrogen atom, a linear or branched alkyl group having a carbon number of 1 to 6, a linear or branched alkenyl group having a carbon number of 2 to 6, a linear or branched alkynyl group having a carbon number of 2 to 6, a carbamoyl group having a carbon number of 1 to 6, an alkoxycarbonyl group having a carbon number of 1 to 6, a substituted or unsubstituted 5- to 8-membered aryl group or a substituted or unsubstituted 5- to 8-membered heterocyclic group, more preferably a hydrogen atom, a linear or branched alkyl group having a carbon number of 1 to 4, a carbamoyl group having a carbon number of 1 to 4, an alkoxycarbonyl group having a carbon number of 1 to 4 or a substituted or unsubstituted 5- to 8-membered aryl group, still more preferably a hydrogen atom, a methyl group or a substituted or unsubstituted 5- or 6-membered aryl group, and most preferably a hydrogen atom.

(iv) $R_3$ is preferably a hydrogen atom or a monovalent substituent, more preferably a hydrogen atom, a methyl group, an ethyl group, an ethenyl group or an ethynyl group, and most preferably a hydrogen atom.

(v) Z is preferably a cyano group, an acyl group having a carbon number of 2 to 6, an acyloxy group having a carbon number of 2 to 6, a carbamoyl group having a carbon number of 1 to 8, an alkyloxycarbonyl group having a carbon number of 2 to 8, an aryloxycarbonyl group having a carbon number of 7 to 12, a nitro group, an alkylsulfinyl group having a carbon number of 1 to 6, an arylsulfinyl group having a carbon number of 6 to 10, an alkylsulfonyl group having a carbon number of 1 to 6, an arylsulfonyl group having a carbon number of 6 to 10, a sulfamoyl group having a carbon number of 0 to 9, a halogenated alkyl group having a carbon number of 1 to 6, a halogenated aryl group having a carbon number of 1 to 6, a halogenated alkyloxy group having a carbon number of 1 to 6, a halogenated alkylthio group having a carbon number of 1 to 6, a halogenated aryloxy group having a carbon number of 6 to 12 or a 5- to 8-membered heterocyclic group, more preferably a cyano group, an alkyloxycarbonyl group having a carbon number of 2 to 8, an alkylsulfonyl group having a carbon number of 1 to 6, an arylsulfonyl group having a carbon number of 6 to 10 or a sulfamoyl group having a carbon number of 0 to 8, and most preferably a cyano group.

(vi) G is preferably a hydrogen atom, a linear or branched alkyl group having a carbon number of 1 to 6, an acyl group having a carbon number of 1 to 4, an alkenyl group having a carbon number of 2 to 6, an alkynyl group having a carbon number of 2 to 6, an aralkyl group having a carbon number of 7 to 10, a 5- to 8-membered saturated or unsaturated hydrocarbon ring or a 5- to 8-membered saturated or unsaturated heterocyclic ring, and when G represents a 5- to 8-membered saturated or unsaturated hydrocarbon ring or heterocyclic ring, the ring is a monocyclic ring or a condensed ring. G may have a substituent. G is more preferably a substituted or unsubstituted 5- to 8-membered aromatic hydrocarbon ring or a substituted or unsubstituted 5- to 8-membered heterocyclic group, and when G represents a 5- to 8-membered aromatic hydrocarbon ring or aromatic heterocyclic ring, the ring is a monocyclic ring or a condensed ring. G is most preferably a substituted or unsubstituted 6-membered aromatic heterocyclic ring, and in this case, the substituted or unsubstituted 6-membered aromatic heterocyclic ring is a monocyclic ring or a condensed ring.

Tautomers of the azo pigment represented by formula (1) are also included in the scope of the present invention. Formula (1) is shown in the form of a canonical formula out of several kinds of tautomers possible in terms of chemical structure, but the pigment may be a tautomer other than the structure shown, and a mixture containing a plurality of kinds of tautomers may also be used. For example, the pigment represented by formula (1) is considered to have an azo-hydrazone tautomer represented by the following formula (1').

The compound represented by the following formula (1'), which is a tautomer of the azo pigment represented by formula (1), is also included in the scope of the present invention.

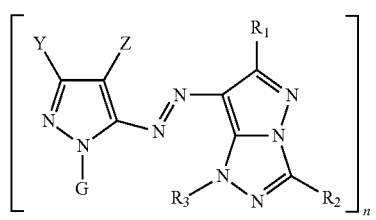

Formula (1)

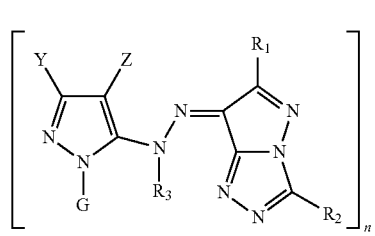

Formula (1')

[Chem. 11]

(wherein in formula (1'), n, $R_1$, $R_2$, $R_3$, Y, Z and G have the same meanings as n, $R_1$, $R_2$, $R_3$, Y, Z and G in formula (1)).

The present invention also relates to an azo pigment represented by formula (2), its tautomer and a salt or hydrate thereof.

The azo pigment represented by formula (2), its tautomer and a salt or hydrate thereof are described in detail below.

Formula (2):

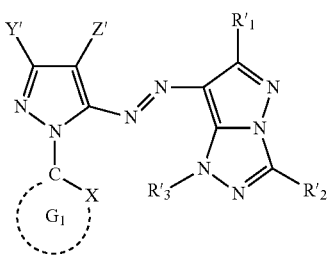

[Chem. 12]

(wherein $R'_1$, $R'_2$ and Y' each independently represents a hydrogen atom, a linear or branched alkyl group having a carbon number of 1 to 4, an alkenyl group having a carbon number of 2 to 4, an alkynyl group having a carbon number of 2 to 4, an acyl group having a carbon number of 1 to 5, an aralkyl group having a carbon number of 7 to 9, a 5- to 8-membered saturated or unsaturated hydrocarbon ring group, or a 5- to 8-membered saturated or unsaturated heterocyclic group; $R'_3$ represents a hydrogen atom or a monovalent substituent; Z' represents an electron-withdrawing group having a Hammett's σp value of 0.2 or more; X represents a heteroatom at the position adjacent to the carbon atom bonded to the pyrazole ring; $G_1$ represents an atomic group for forming a 5- to 8-membered saturated or unsaturated heterocyclic ring; when any one of $R'_1$, $R'_2$, $R'_3$, Y' and $G_1$ represents a 5- to 8-membered saturated or unsaturated heterocyclic ring, the ring is a monocyclic ring or a condensed ring; and when any one of $R'_1$, $R'_2$, $R'_3$, Y' and $G_1$ represents a 5-membered unsaturated heterocyclic ring, the ring contains two or more nitrogen atoms therein).

$R'_1$, $R'_2$, $R'_3$, Y', Z', X and $G_1$ in formula (2) are described in more detail below.

$R'_1$, $R'_2$, $R'_3$, Y', Z' and $G_1$ may have a substituent.

In formula (2), $R'_1$ and $R'_2$ each is independently, preferably a hydrogen atom, a linear or branched alkyl group having a carbon number of 1 to 4, an alkenyl group having a carbon number of 2 to 4, an alkynyl group having a carbon number of 2 to 4, an aralkyl group having a carbon number of 7 to 9, a 5- to 8-membered saturated or unsaturated hydrocarbon ring group or a 5- to 8-membered saturated or unsaturated heterocyclic group. When either one of $R'_1$ and $R'_2$ represents a 5- to 8-membered saturated or unsaturated hydrocarbon ring group or a 5- to 8-membered saturated or unsaturated heterocyclic group, the ring is a monocyclic ring or a condensed ring, and when substitutable, $R'_1$ and $R'_2$ each may have a substituent or may be unsubstituted. $R'_1$ and $R'_2$ each is more preferably a hydrogen atom, a linear or branched alkyl group having a carbon number of 1 to 4, a 5- to 8-membered saturated or unsaturated hydrocarbon ring group or a 5- to 8-membered saturated or unsaturated heterocyclic group. When either one of $R'_1$ and $R'_2$ represents a 5- to 8-membered saturated or unsaturated hydrocarbon ring group or a 5- to 8-membered saturated or unsaturated heterocyclic group, the ring is a monocyclic ring or a condensed ring and when substitutable, $R'_1$ and $R'_2$ each may have a substituent or may be unsubstituted. $R'_1$ and $R'_2$ each is most preferably a methyl group, a tert-butyl group, a substituted or unsubstituted 5- to 8-membered aryl group or a substituted or unsubstituted 5- to 8-membered aromatic heterocyclic group.

Examples of the group of $R'_3$ are the same as examples of $R_3$ in formula (1), and preferred examples are also the same.

Examples of the group of Z' are the same as examples of Z in formula (1), and preferred examples are also the same.

In formula (2), Y' is preferably a hydrogen atom, a linear or branched alkyl group having a carbon number of 1 to 4, an alkenyl group having a carbon number of 2 to 4, an alkynyl group having a carbon number of 2 to 4, an aralkyl group having a carbon number of 7 to 9, a 5- to 8-membered saturated or unsaturated hydrocarbon ring group or a 5- to 8-membered saturated or unsaturated heterocyclic group. When Y' represents a 5- to 8-membered saturated or unsaturated hydrocarbon ring group or a 5- to 8-membered saturated or unsaturated heterocyclic group, the ring is a monocyclic ring or a condensed ring, and when substitutable, Y' may have a substituent or may be unsubstituted. Y' is more preferably a hydrogen atom, a linear or branched alkyl group having a carbon number of 1 to 4, a 5- to 8-membered saturated or unsaturated hydrocarbon ring group or a 5- to 8-membered saturated or unsaturated heterocyclic group. When Y' represents a 5- to 8-membered saturated or unsaturated hydrocarbon ring group or a 5- to 8-membered saturated or unsaturated heterocyclic group, the ring is a monocyclic ring or a condensed ring and when substitutable, Y' may have a substituent or may be unsubstituted. Y' is still more preferably a hydrogen atom, a methyl group, a tert-butyl group, a substituted or unsubstituted 6-membered aromatic hydrocarbon ring group or a substituted or unsubstituted 6-membered aromatic heterocyclic group.

In formula (2), X represents an atom at the position adjacent to the carbon atom and is preferably a heteroatom, more preferably a nitrogen atom, a sulfur atom, an oxygen atom or a selenium atom, still more preferably a nitrogen atom, a sulfur atom or an oxygen atom, and most preferably a nitrogen atom.

When X is a nitrogen atom, this makes it easy to form more strongly not only the intermolecular interaction of colorant molecules but also the intramolecular interaction. In turn, a pigment having a more stable molecular arrangement can be easily configured, and the pigment advantageously exhibits good hue and high fastness (resistance to light, gas, heat, solvent or the like).

$G_1$ is preferably a 5- to 8-membered saturated or unsaturated heterocyclic ring, and when $G_1$ represents a 5- to 8-membered saturated or unsaturated heterocyclic ring, the ring is a monocyclic ring or a condensed ring. $G_1$ may have a substituent. $G_1$ is more preferably a substituted or unsubstituted 5- to 8-membered aromatic heterocyclic ring. When $G_1$ represents a 5- to 8-membered aromatic heterocyclic ring, the ring is a monocyclic ring or a condensed ring, and when $G_1$ represents a 5-membered aromatic heterocyclic ring, the ring contains two or more nitrogen atoms therein. In particular, $G_1$ is preferably a substituted or unsubstituted 6-membered aromatic heterocyclic ring, more preferably any one selected from the group of substituents represented by (3)-1 to (3)-6 in the following formula (3), and the group of substituents represented by (3)-1 or (3)-2 is most preferred.

Formula (3):

[Chem. 13]

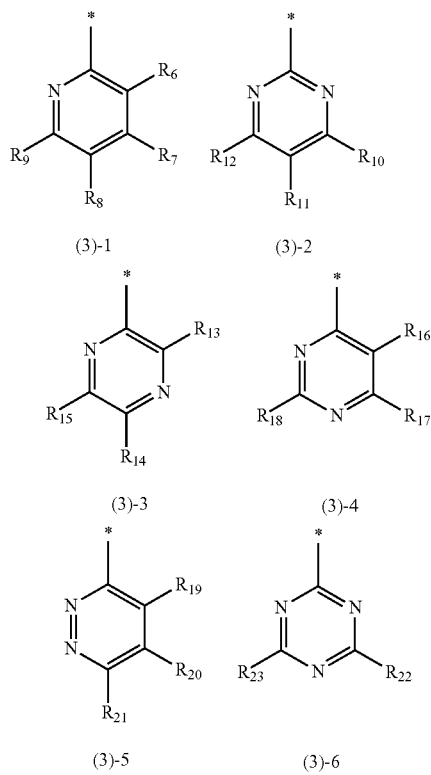

In formula (3), $R_6$ to $R_{23}$ each independently represents a hydrogen atom, a hydroxyl group, an amino group, a linear or branched alkyl group having a carbon number of 1 to 4, a cycloalkyl group having a carbon number of 5 to 8, an acyl group having a carbon number of 1 to 5, an alkenyl group having a carbon number of 2 to 4, an alkynyl group having a carbon number of 2 to 4, an alkyloxy group having a carbon number of 1 to 4, an alkylamino group having a carbon number of 1 to 8, an alkyloxycarbonyl group having a carbon number of 2 to 5, an amide group having a carbon number of 1 to 5, an aralkyl group having a carbon number of 7 to 10, a 5- to 8-membered saturated or unsaturated hydrocarbon ring or a 5- to 8-membered saturated or unsaturated heterocyclic ring. When $R_6$ to $R_{23}$ each represents a 5- to 8-membered saturated or unsaturated hydrocarbon ring or heterocyclic ring, the ring is a monocyclic ring or a condensed ring, and when substitutable, $R_6$ to $R_{23}$ each may have a substituent or may be unsubstituted. $R_6$ to $R_{23}$ each is more preferably a hydrogen atom, a hydroxyl group, an amino group, a linear or branched alkyl group having a carbon number of 1 to 4, an acyl group having a carbon number of 1 to 5, an alkyloxy group having a carbon number of 1 to 4, an alkylamino group having a carbon number of 1 to 8, an alkyloxycarbonyl group having a carbon number of 2 to 5 or an amide group having a carbon number of 0.1 to 5, still more preferably a hydrogen atom, a hydroxyl group, an amino group, a methyl group, a methyloxy group, a methylamino group or an acetamide group.

$R_6$ to $R_{21}$ may form a bond with each other, and in this case, $R_6$ to $R_{21}$ each is preferably a nonmetallic atom group necessary for forming a 5- to 7-membered hydrocarbon ring or a 5- to 7-membered heteroatom ring, more preferably a nonmetallic atom group necessary for forming a 6-membered aromatic hydrocarbon ring or a 6-membered aromatic heteroatom ring.

In formula (2), examples of the heterocyclic group represented by $G_1$ include, as set forth without limiting the substitution position, a pyridyl group, a pyrazinyl group, a pyridazinyl group, a pyrimidinyl group, a triazinyl group, a quinolinyl group, an isoquinolinyl, a quinazolinyl group, a cinnolinyl group, a phthalazinyl group, a quinoxalinyl group, a pyrrolyl group, an indolyl group, a furanyl group, a benzofuranyl group, a pyrazolyl group, an imidazolyl group, a benzimidazolyl group, a triazolyl group, an oxazolyl group, a benzoxazolyl group, a thiadiazolyl group, an isoxazolyl group, a benzisoxazolyl group, a pyrrolidinyl group, a piperidinyl group, a piperazinyl group, an imidazolidinyl group and a sulfolanyl group.

Among these, a pyridyl group, a pyrazinyl group, a pyrimidinyl group, a pyridazinyl group and a triazinyl group are preferred, and a pyridyl group, a pyrimidinyl group and a triazinyl group are more preferred.

In the case where $G_1$ is a group that can further have a substituent, examples of the substituent include the same groups as those described for $R_1$, $R_2$, $R_3$, Y, Z and G in formula (1).

As for the combination of preferred substituents in the pigment represented by formula (2) of the present invention, a compound where at least one of various groups is the above-described preferred group is preferred, a compound where a larger number of various groups are the above-described preferred groups is more preferred, and a compound where all groups are the above-described preferred groups is most preferred.

The particularly preferred combination as the azo pigment represented by formula (2) of the present invention includes the following (i) to (vii).

(i) $R'_1$ and $R'_2$ each is independently, preferably a hydrogen atom, a linear or branched alkyl group having a carbon number of 1 to 4, an alkenyl group having a carbon number of 2 to 4, an alkynyl group having a carbon number of 2 to 4, an aralkyl group having a carbon number of 7 to 9, a 5- to 8-membered saturated or unsaturated hydrocarbon ring group or a 5- to 8-membered saturated or unsaturated heterocyclic group. When either one of $R'_1$ and $R'_2$ represents a 5- to 8-membered saturated or unsaturated hydrocarbon ring group or a 5- to 8-membered saturated or unsaturated heterocyclic group, the ring is a monocyclic ring or a condensed ring, and when substitutable, $R'_1$ and $R'_2$ each may have a substituent or may be unsubstituted. Moreover, $R'_1$ and $R'_2$ each is more preferably a hydrogen atom, a linear or branched alkyl group having a carbon number of 1 to 4, a 5- to 8-membered saturated or unsaturated hydrocarbon ring group or a 5- to 8-membered saturated or unsaturated heterocyclic group. When either one of $R'_1$ and $R'_2$ represents a 5- to 8-membered saturated or unsaturated hydrocarbon ring group or a 5- to 8-membered saturated or unsaturated heterocyclic group, the ring is a monocyclic ring or a condensed ring and when substitutable, $R'_1$ and $R'_2$ each may have a substituent or may be unsubstituted. $R'_1$ and $R'_2$ each is still more preferably a linear or branched alkyl group having a carbon number of 1 to 4, a substituted or unsubstituted 5- to 8-membered aryl group or a substituted or unsubstituted 5- to 8-membered aromatic heterocyclic group, yet still more preferably a linear or branched alkyl group having a carbon number of 1 to 4. The linear or branched alkyl group having a carbon number of 1 to 4 is preferably a methyl group or a tert-butyl group, more preferably a methyl group.

(ii) Y' is preferably a hydrogen atom, a linear or branched alkyl group having a carbon number of 1 to 4, an alkenyl group having a carbon number of 2 to 4, an alkynyl group having a carbon number of 2 to 4, an aralkyl group having a carbon number of 7 to 9, a 5- to 8-membered saturated or unsaturated hydrocarbon ring group or a 5- to 8-membered saturated or unsaturated heterocyclic group. When Y' represents a 5- to 8-membered saturated or unsaturated hydrocarbon ring group or a 5- to 8-membered saturated or unsaturated heterocyclic group, the ring is a monocyclic ring or a condensed ring, and when substitutable, Y' may have a substituent or may be unsubstituted. Y' is more preferably a hydrogen atom, a linear or branched alkyl group having a carbon number of 1 to 4, a 5- to 8-membered saturated or unsaturated hydrocarbon ring group or a 5- to 8-membered saturated or unsaturated heterocyclic group. When Y' represents a 5- to 8-membered saturated or unsaturated hydrocarbon ring group or a 5- to 8-membered saturated or unsaturated heterocyclic group, the ring is a monocyclic ring or a condensed ring and when substitutable, Y' may have a substituent or may be unsubstituted. Y' is still more preferably a hydrogen atom, a methyl group, a tert-butyl group, a substituted or unsubstituted 6-membered aromatic hydrocarbon ring group or a substituted or unsubstituted 6-membered aromatic heterocyclic group, and most preferably a hydrogen atom.

$R'_3$ is preferably a hydrogen atom or a monovalent substituent, more preferably a hydrogen atom, a methyl group, an ethyl group, an ethenyl group or an ethynyl group, and most preferably a hydrogen atom.

(iv) Z' is preferably a cyano group, an acyl group having a carbon number of 2 to 6, an acyloxy group having a carbon number of 2 to 6, a carbamoyl group having a carbon number of 1 to 8, an alkyloxycarbonyl group having a carbon number of 2 to 8, an aryloxycarbonyl group having a carbon number of 7 to 12, a nitro group, an alkylsulfinyl group having a carbon number of 1 to 6, an arylsulfinyl group having a carbon number of 6 to 10, an alkylsulfonyl group having a carbon number of 1 to 6, an arylsulfonyl group having a carbon number of 6 to 10, a sulfamoyl group having a carbon number of 0 to 9, a halogenated alkyl group having a carbon number of 1 to 6, a halogenated aryl group having a carbon number of 1 to 6, a halogenated alkyloxy group having a carbon number of 6 to 12, a halogenated alkylthio group having a carbon number of 1 to 6, a halogenated aryloxy group having a carbon number of 6 to 12 or a 5- to 8-membered heterocyclic group having a carbon number of 1 to 10, more preferably a cyano group, an alkyloxycarbonyl group having a carbon number of 2 to 8, an alkylsulfonyl group having a carbon number of 1 to 6, an arylsulfonyl group having a carbon number of 6 to 10 or a sulfamoyl group having a carbon number of 0 to 8, and most preferably a cyano group.

(v) X is preferably a heteroatom, more preferably a nitrogen atom, an oxygen atom, a sulfur atom or a selenium atom, still more preferably a nitrogen atom, an oxygen atom or a sulfur atom, and most preferably a nitrogen atom.

(vi) $G_1$ is preferably a 5- to 8-membered saturated or unsaturated heterocyclic ring, and when $G_1$ represents a 5- to 8-membered saturated or unsaturated heterocyclic ring, the ring is a monocyclic ring or a condensed ring. $G_1$ may have a substituent. When $G_1$ represents a 5-membered unsaturated heterocyclic ring, the ring contains two or more nitrogen atoms therein. $G_1$ is more preferably a substituted or unsubstituted 5- to 8-membered aromatic heterocyclic ring, and when $G_1$ represents a 5- to 8-membered aromatic heterocyclic ring, the ring is a monocyclic ring or a condensed ring. When $G_1$ represents a 5-membered aromatic heterocyclic ring, the ring contains two or more nitrogen atoms therein. In particular, $G_1$ is preferably a substituted or unsubstituted 6-membered aromatic heterocyclic ring, more preferably any one selected from the group of substituents represented by (3)-1 to (3)-6 in the following formula (3), and the group of substituents represented by (3)-1 or (3)-2 is most preferred.

Formula (3):

[Chem. 14]

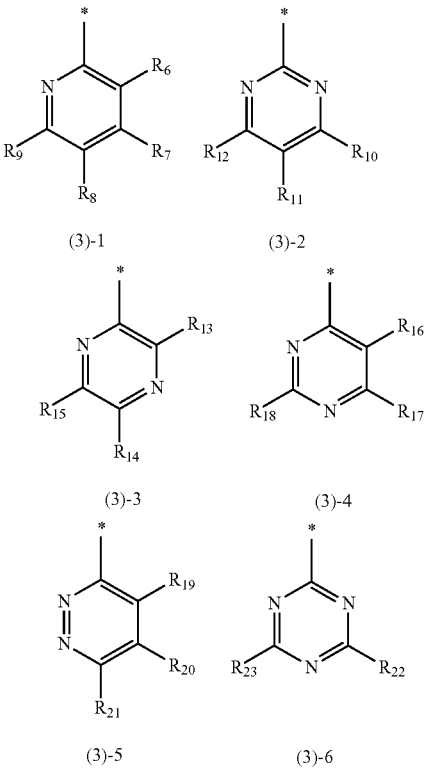

(vii) $R_6$ to $R_{23}$ each is independently a hydrogen atom, a hydroxyl group, an amino group, a linear or branched alkyl group having a carbon number of 1 to 4, a cycloalkyl group having a carbon number of 5 to 8, an acyl group having a carbon number of 1 to 5, an alkenyl group having a carbon number of 2 to 4, an alkynyl group having a carbon number of 2 to 4, an alkyloxy group having a carbon number of 1 to 4, an alkylamino group having a carbon number of 1 to 8, an alkyloxycarbonyl group having a carbon number of 2 to 5, an amide group having a carbon number of 1 to 5, an aralkyl group having a carbon number of 7 to 10, a 5- to 8-membered saturated or unsaturated hydrocarbon ring or a 5- to 8-membered saturated or unsaturated heterocyclic ring. When $R_6$ to $R_{23}$ each represents a 5- to 8-membered saturated or unsaturated hydrocarbon ring or heterocyclic ring, the ring is a monocyclic ring or a condensed ring. $R_6$ to $R_{23}$ may have a substituent. $R_6$ to $R_{23}$ each is preferably a hydrogen atom, a hydroxyl group, an amino group, a linear or branched alkyl group having a carbon number of 1 to 4, an acyl group having a carbon number of 1 to 5, an alkyloxy group having a carbon number of 1 to 4, an alkylamino group having a carbon number of 1 to 8, an alkyloxycarbonyl group having a carbon number of 2 to 5 or an amide group having a carbon number of 1 to 5, more preferably a hydrogen atom, a hydroxyl group, an amino group, a methyl group, a methyloxy group, a methylamino group or an acetamide group.

$R_6$ to $R_{21}$ may combine with each other to form ring, and in this case, $R_6$ to $R_{21}$ each is preferably a nonmetallic atom group necessary for forming a 5- to 7-membered hydrocarbon ring or a 5- to 7-membered heteroatom ring, more preferably a nonmetallic atom group necessary for forming a 6-membered aromatic hydrocarbon ring or a 6-membered aromatic heteroatom ring.

Tautomers of the azo pigment represented by formula (2) are also included in the scope of the present invention. Formula (2) is shown in the form of a canonical formula out of several kinds of tautomers possible in terms of chemical structure, but the pigment may be a tautomer other than the structure shown, and a mixture containing a plurality of kinds of tautomers may also be used. For example, the pigment represented by formula (2) is considered to have an azohydrazone tautomer represented by the following formula (2').

The compound represented by the following formula (2'), which is a tautomer of the azo pigment represented by formula (2), is also included in the scope of the present invention.

Formula (4):

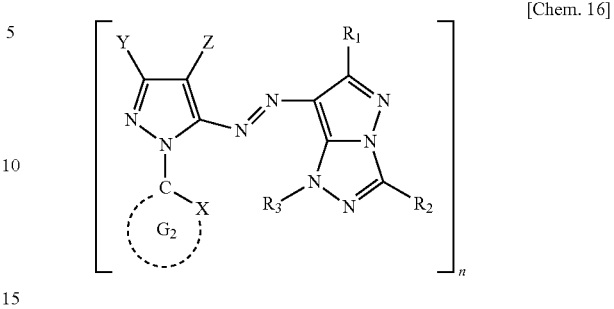

[Chem. 16]

In formula (4), n, $R_1$, $R_2$, $R_3$, Y and Z each independently has the same meaning as n, $R_1$, $R_2$, $R_3$, Y or Z in formula (1), and X has the same meaning as X in formula (2). $G_2$ represents an atomic group for forming a 5- to 8-membered saturated or unsaturated heterocyclic ring, and the formula represents a dimer through $R_1$, $R_2$, $R_3$, Y, Z or $G_2$ when n is 2, represents a trimer through $R_1$, $R_2$, $R_3$, Y, Z or $G_2$ when n is 3, and represents a tetramer through $R_1$, $R_2$, $R_3$, Y, Z or $G_2$ when n is 4. When any one of $R_1$, $R_2$, $R_3$, Y and $G_2$ represents a 5- to 8-membered saturated or unsaturated heterocyclic ring, the ring is a monocyclic ring or a condensed ring.

n, $R_1$, $R_2$, $R_3$, Y, Z, X and $G_2$ in formula (4) are described in more detail below.

In formula (4), examples of each group of n, $R_1$, $R_2$, $R_3$, Y and Z are independently the same as examples of respective groups of n, Rt, $R_2$, $R_3$, Y and Z in formula (1), and preferred examples are also the same.

Examples of each X are independently the same as examples of X in formula (2), and preferred examples are also the same.

$G_2$ is preferably a 5- to 8-membered saturated or unsaturated heterocyclic ring, and when $G_2$ represents a 5- to 8-membered saturated or unsaturated heterocyclic ring, the ring is a monocyclic ring or a condensed ring. $G_2$ may have a substitu-

[Chem. 15]

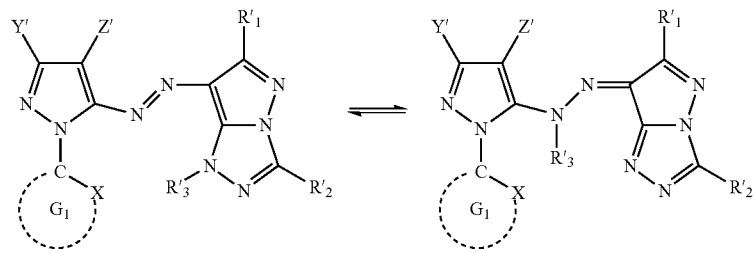

Formula (2)    Formula (2')

(wherein in formula (2'), $R'_1$, Y', Z' and $G_1$ have the same meanings as $R'_1$, $R'_2$, $R'_3$, Y', Z' and $G_1$ in formula (2)).

The azo pigment represented by formula (1) is preferably an azo pigment represented by the following formula (4).

The azo pigment represented by formula (4), its tautomer and a salt or hydrate thereof are described in detail below.

ent. $G_2$ is more preferably a substituted or unsubstituted 5- to 8-membered aromatic heterocyclic ring, and when $G_2$ represents a 5- to 8-membered aromatic heterocyclic ring, the ring is a monocyclic ring or a condensed ring. $G_2$ is still more preferably a substituted or unsubstituted 6-membered aromatic heterocyclic ring, and most preferably any one selected from the group of substituents represented by (3)-1 to (3)-6 in the following formula (3).

Formula (3):

(3)-1
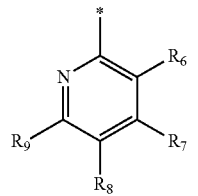

(3)-2
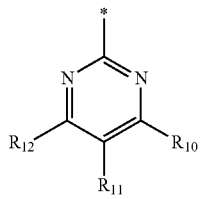

(3)-3
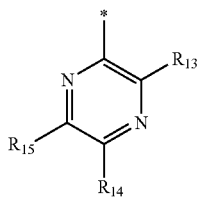

(3)-4
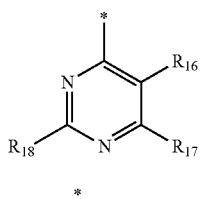

(3)-5
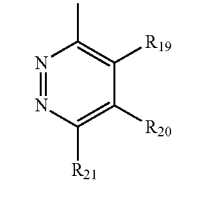

(3)-6
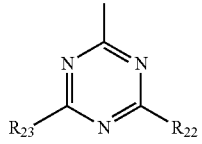

In formula (3), $R_6$ to $R_{23}$ each independently represents a hydrogen atom, a hydroxyl group, an amino group, a linear or branched alkyl group having a carbon number of 1 to 4, a cycloalkyl group having a carbon number of 5 to 8, an acyl group having a carbon number of 1 to 5, an alkenyl group having a carbon number of 2 to 4, an alkynyl group having a carbon number of 2 to 4, an alkyloxy group having a carbon number of 1 to 4, an alkylamino group having a carbon number of 1 to 8, an alkyloxycarbonyl group having a carbon number of 2 to 5, an amide group having a carbon number of 1 to 5, an aralkyl group having a carbon number of 7 to 10, a 5- to 8-membered saturated or unsaturated hydrocarbon ring or a 5- to 8-membered saturated or unsaturated heterocyclic ring. When $R_6$ to $R_{23}$ each represents a 5- to 8-membered saturated or unsaturated hydrocarbon ring or heterocyclic ring, the ring is a monocyclic ring or a condensed ring, and when substitutable, $R_6$ to $R_{23}$ each may have a substituent or may be unsubstituted. $R_6$ to $R_{23}$ each is more preferably a hydrogen atom, a hydroxyl group, an amino group, a linear or branched alkyl group having a carbon number of 1 to 4, an acyl group having a carbon number of 1 to 5, an alkyloxy group having a carbon number of 1 to 4, an alkylamino group having a carbon number of 1 to 8, an alkyloxycarbonyl group having a carbon number of 2 to 5 or an amide group having a carbon number of 1 to 5, still more preferably a hydrogen atom, a hydroxyl group, an amino group, a methyl group, a methyloxy group, a methylamino group or an acetamide group.

In the case where $R_6$ to $R_{21}$ form a bond with each other, $R_6$ to $R_{21}$ each is preferably a nonmetallic atom group necessary for forming a 5- to 7-membered hydrocarbon ring or a 5- to 7-membered heteroatom ring, more preferably a nonmetallic atom group necessary for forming a 6-membered aromatic hydrocarbon ring or a 6-membered aromatic heteroatom ring.

In formula (4), examples of the heterocyclic group represented by $G_2$ include, as set forth without limiting the substitution position, a pyridyl group, a pyrazinyl group, a pyridazinyl group, a pyrimidinyl group, a triazinyl group, a quinolinyl group, an isoquinolinyl, a quinazolinyl group, a cinnolinyl group, a phthalazinyl group, a quinoxalinyl group, a pyrrolyl group, an indolyl group, a furanyl group, a benzofuranyl group, a thiophenyl group, a benzothiophenyl group, a pyrazolyl group, an imidazolyl group, a benzimidazolyl group, a triazolyl group, an oxazolyl group, a benzoxazolyl group, a thiazolyl group, a benzothiazolyl group, an isothiazolyl group, a benzisothiazolyl group, a thiadiazolyl group, an isoxazolyl group, a benzisoxazolyl group, a pyrrolidinyl group, a piperidinyl group, a piperazinyl group, an imidazolidinyl group and a sulfolanyl group.

Among these, a pyridyl group, a pyrazinyl group, a pyrimidinyl group, a pyridazinyl group and a triazinyl group are preferred, and a pyridyl group, a pyrimidinyl group and a triazinyl group are more preferred.

In the case where $G_2$ is a group that can further have a substituent, examples of the substituent include the same groups as those described for $R_1$, $R_2$, $R_3$, Y, Z and G in formula (1).

In the case where $R_1$, $R_2$, $R_3$, Y and Z each represents a divalent group, the divalent group is preferably an alkylene group (e.g., methylene, ethylene, propylene, butylene, pentylene), an alkenylene group (e.g., ethenylene, propenylene), an alkynylene group (e.g., ethynylene, propynylene), an arylene group (e.g., phenylene, naphthylene), a divalent heterocyclic group (e.g., 6-chloro-1,3,5-triazine-2,4-diyl, pyrimidine-2,4-diyl, pyrimidine-4,6-diyl, quinoxaline-2,3-diyl, pyridazine-3,6-diyl), —O—, —CO—, —NR'— (R' is a hydrogen atom, an alkyl group or an aryl group), —S—, —SO$_2$—, —SO— or a combination thereof (e.g., —NHCH$_2$CH$_2$NH—, —NH-CONH—).

The alkylene group, the alkenylene group, the alkynylene group, the arylene group, the divalent heterocyclic group and the alkyl group or aryl group of R' may have a substituent.

Examples of the substituent include the same substituents as those described for $R_1$, $R_2$, $R_3$, Y, Z and G in formula (1).

The alkyl group and aryl group of R' have the same meanings as the substituents described above when $R_1$, $R_2$, $R_3$, Y, Z and G each is an alkyl group or an aryl group.

The divalent group is more preferably an alkylene group having a carbon atom of 6 or less, an alkenylene group having a carbon number of 6 or less, an alkynylene group having a carbon number of 6 or less, an arylene group having a carbon number of 6 to 10, a divalent heterocyclic group, —S—, —SO—, —SO$_2$— or a combination thereof (e.g., —SCH$_2$CH$_2$S—, —SCH$_2$CH$_2$CH$_2$S—).

In the case where G$_2$ represents a divalent group, the divalent group is preferably a divalent heterocyclic group (e.g., 6-chloro-1,3,5-triazine-2,4-diyl, pyrimidine-2,4-diyl, pyrimidine-4,6-diyl, quinoxaline-2,3-diyl, pyridazine-3,6-diyl).

The divalent heterocyclic group may have a substituent.

Examples of the substituent are the same as those of the substituents described for R$_1$, R$_2$, R$_3$, Y, Z and G in formula (1).

The total carbon number of the divalent linking group is preferably from 0 to 20, more preferably from 0 to 15, and most preferably from 0 to 10.

In the case where R$_1$, R$_2$, R$_3$, Y and Z each represents a trivalent group, the trivalent group is preferably a trivalent hydrocarbon group, a trivalent heterocyclic group, >N—, or a combination of this and a divalent group (e.g., >NCH$_2$CH$_2$NH—, >NCONH—).

In the case where G$_2$ represents a trivalent group, the trivalent group is preferably a trivalent heterocyclic group (e.g., 1,3,5-triazine-2,4,6-triyl, pyrimidine-2,4,6-triyl).

The total carbon number of the trivalent linking group is preferably from 0 to 20, more preferably from 0 to 15, and most preferably from 0 to 10.

As for the combination of preferred substituents in the pigment represented by formula (4) of the present invention, a compound where at least one of various groups is the above-described preferred group is preferred, a compound where a larger number of various groups are the above-described preferred groups is more preferred, and a compound where all groups are the above-described preferred groups is most preferred.

The particularly preferred combination as the azo pigment represented by formula (4) of the present invention includes the following (i) to (vii).

(i) n represents an integer of 2 to 4 and is preferably an integer of 2 to 3, more preferably 2.

(ii) R$_1$ and R$_2$ each is independently, preferably a hydrogen atom, a linear or branched alkyl group having a carbon number of 1 to 6, a linear or branched alkenyl group having a carbon number of 2 to 6, a linear or branched alkynyl group having a carbon number of 2 to 6, a substituted or unsubstituted 5- to 8-membered aryl group or a substituted or unsubstituted 5- to 8-membered heterocyclic group, more preferably a hydrogen atom, a linear or branched alkyl group having a carbon number of 1 to 4 or a substituted or unsubstituted 5- to 8-membered aryl group, still more preferably a linear or branched alkyl group having a carbon number of 1 to 4 or an unsubstituted 5- or 6-membered aryl group, yet still more preferably a linear or branched alkyl group having a carbon number of 1 to 4. The linear or branched alkyl group having a carbon number of 1 to 4 is preferably a methyl group or a tert-butyl group, more preferably a methyl group.

(iii) Y is preferably a hydrogen atom, a linear or branched alkyl group having a carbon number of 1 to 6, a linear or branched alkenyl group having a carbon number of 2 to 6, a linear or branched alkynyl group having a carbon number of 2 to 6, a carbamoyl group having a carbon number of 1 to 6, an alkoxycarbonyl group having a carbon number of 1 to 6, a substituted or unsubstituted 5- to 8-membered aryl group or a substituted or unsubstituted 5- to 8-membered heterocyclic group, more preferably a hydrogen atom, a linear or branched alkyl group having a carbon number of 1 to 4, a carbamoyl group having a carbon number of 1 to 4, an alkoxycarbonyl group having a total carbon number of 1 to 4 or a substituted or unsubstituted 5- to 8-membered aryl group, still more preferably a hydrogen atom, a methyl group or a substituted or unsubstituted 5- or 6-membered aryl group, and most preferably a hydrogen atom.

(iv) R$_3$ is preferably a hydrogen atom or a monovalent substituent, more preferably a hydrogen atom, a methyl group, an ethyl group, an ethenyl group or an ethynyl group, and most preferably a hydrogen atom.

(v) Z is preferably a cyano group, an acyl group having a carbon number of 2 to 6, an acyloxy group having a carbon number of 2 to 6, a carbamoyl group having a carbon number of 1 to 8, an alkyloxycarbonyl group having a carbon number of 2 to 8, an aryloxycarbonyl group having a carbon number of 7 to 12, a nitro group, an alkylsulfinyl group having a carbon number of 1 to 6, an arylsulfinyl group having a carbon number of 6 to 10, an alkylsulfonyl group having a carbon number of 1 to 6, an arylsulfonyl group having a carbon number of 6 to 10, a sulfamoyl group having a carbon number of 0 to 9, a halogenated alkyl group having a carbon number of 1 to 6, a halogenated aryl group having a carbon number of 1 to 6, a halogenated alkyloxy group having a carbon number of 1 to 6, a halogenated alkylthio group having a carbon number of 1 to 6, a halogenated aryloxy group having a carbon number of 6 to 12 or a 5- to 8-membered heterocyclic group, more preferably a cyano group, an alkyloxycarbonyl group having a carbon number of 2 to 8, an alkylsulfonyl group having a carbon number of 1 to 6, an arylsulfonyl group having a carbon number of 6 to 10 or a sulfamoyl group having a carbon number of 0 to 8, and most preferably a cyano group.

(vi) X is preferably a heteroatom, more preferably a nitrogen atom, an oxygen atom, a sulfur atom or a selenium atom, still more preferably a nitrogen atom, an oxygen atom or a sulfur atom, and most preferably a nitrogen atom.

(vii) G$_2$ is preferably a 5- to 8-membered saturated or unsaturated heterocyclic ring, and when G$_2$ represents a 5- to 8-membered saturated or unsaturated heterocyclic ring, the ring is a monocyclic ring or a condensed ring. Also, when substitutable, G$_2$ may further have a substituent or may be unsubstituted. When G$_2$ represents a 5-membered unsaturated heterocyclic ring, the ring contains two or more nitrogen atoms therein. G$_2$ is more preferably a substituted or unsubstituted 5- to 8-membered aromatic heterocyclic ring, and when G$_2$ represents a 5- to 8-membered aromatic heterocyclic ring, the ring is a monocyclic ring or a condensed ring. When G$_2$ represents a 5-membered aromatic heterocyclic ring, the ring contains two or more nitrogen atoms therein. In particular, G$_2$ is preferably a substituted or unsubstituted 6-membered aromatic heterocyclic ring, more preferably any one selected from the group of substituents represented by (3)-1 to (3)-6 in the following formula (3), and the group of substituents represented by (3)-1 or (3)-2 is most preferred.

Formula (3):

[Chem. 18]

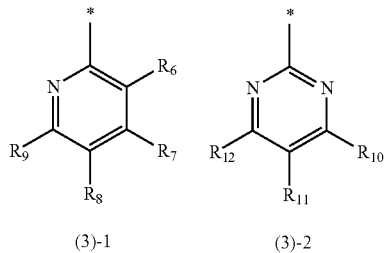

(3)-1        (3)-2

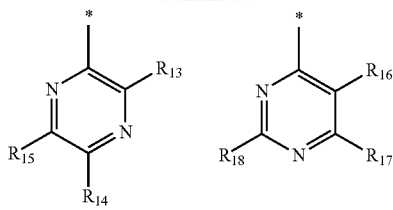

(3)-3  (3)-4

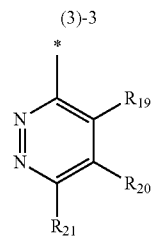  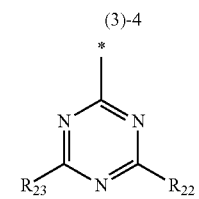

(3)-5  (3)-6

$R_6$ to $R_{21}$ may form a bond with each other, and in this case, $R_6$ to $R_{21}$ each is preferably a nonmetallic atom group necessary for forming a 5- to 7-membered hydrocarbon ring or a 5- to 7-membered heteroatom ring, more preferably a nonmetallic atom group necessary for forming a 6-membered aromatic hydrocarbon ring or a 6-membered aromatic heteroatom ring.

Tautomers of the azo pigment represented by formula (4) are also included in the scope of the present invention. Formula (4) is shown in the form of a canonical formula out of several kinds of tautomers possible in terms of chemical structure, but the pigment may be a tautomer other than the structure shown, and a mixture containing a plurality of kinds of tautomers may also be used. For example, the pigment represented by formula (4) is considered to have an azohydrazone tautomer represented by the following formula (4').

The compound represented by the following formula (4), which is a tautomer of the azo pigment represented by formula (4), is also included in the scope of the present invention.

[Chem. 19]

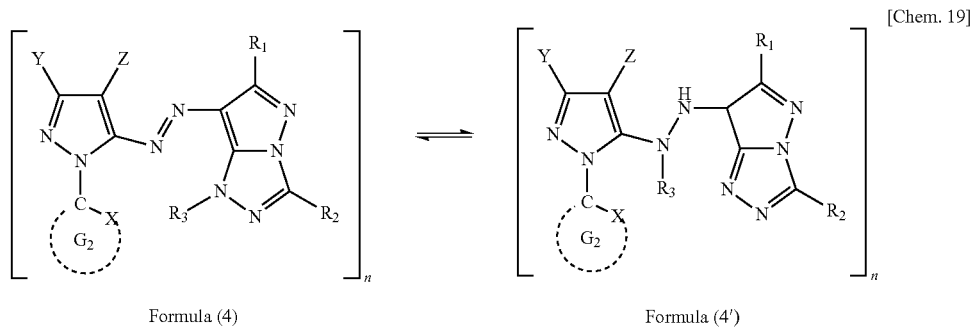

Formula (4)     Formula (4')

$R_6$ to $R_{23}$ each is independently a hydrogen atom, a hydroxyl group, an amino group, a linear or branched alkyl group having a carbon number of 1 to 4, a cycloalkyl group having a carbon number of 5 to 8, an acyl group having a carbon number of 1 to 5, an alkenyl group having a carbon number of 2 to 4, an alkynyl group having a carbon number of 2 to 4, an alkyloxy group having a carbon number of 1 to 4, an alkylamino group having a carbon number of 1 to 8, an alkyloxycarbonyl group having a carbon number of 2 to 5, an amide group having a carbon number of 1 to 5, an aralkyl group having a carbon number of 7 to 10, a 5- to 8-membered saturated or unsaturated hydrocarbon ring or a 5- to 8-membered saturated or unsaturated heterocyclic ring. When $R_6$ to $R_{23}$ each represents a 5- to 8-membered saturated or unsaturated hydrocarbon ring or heterocyclic ring, the ring is a monocyclic ring or a condensed ring. $R_6$ to $R_{23}$ may have a substituent. $R_6$ to $R_{23}$ each is preferably a hydrogen atom, a hydroxyl group, an amino group, a linear or branched alkyl group having a carbon number of 1 to 4, an acyl group having a carbon number of 1 to 5, an alkyloxy group having a carbon number of 1 to 4, an alkylamino group having a carbon number of 1 to 8, an alkyloxycarbonyl group having a carbon number of 2 to 5 or an amide group having a carbon number of 1 to 5, more preferably a hydrogen atom, a hydroxyl group, an amino group, a methyl group, a methyloxy group, a methylamino group or an acetamide group.

(wherein in formula (4), n, $R_1$, $R_2$, $R_3$, X, Y, Z and $G_2$ have the same meanings as n, $R_1$, $R_2$, $R_3$, X, Y, Z and $G_2$ in formula (4)).

The azo pigment represented by formula (2) is preferably an azo pigment represented by the following formula (5).

The azo pigment represented by formula (5), its tautomer and a salt or hydrate thereof are described in detail below.

Formula (5):

[Chem. 20]

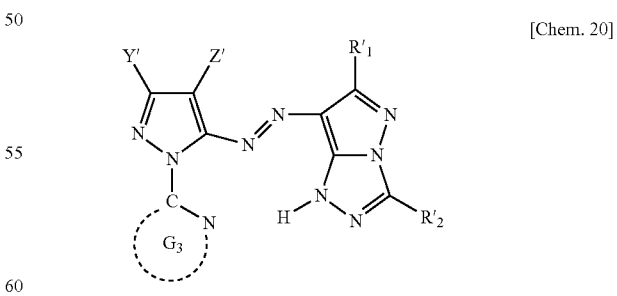

(wherein $R'_1$, $R'_2$, Y' and Z' each independently has the same meaning as $R'_1$, $R'_2$, Y' and Z' in formula (2); $G_3$ represents a nonmetallic atom group for forming a 5- or 6-membered nitrogen-containing aromatic heterocyclic ring; when $G_3$ represents a 5- or 6-membered nitrogen-containing aromatic heterocyclic ring, the ring is a mono cyclic ring or a condensed ring; G₃ may have a substituent; and when G₃ represents a 5-membered nitrogen-containing aromatic heterocyclic ring, the ring contains two or more nitrogen atoms therein).

R'₁, R'₂, Y', Z' and G₃ in formula (5) are described in more detail below.

Examples of each group of R'₁, R'₂ and Y' are independently the same as examples of respective groups of R'₁, R'₂ and Y' in formula (2), and preferred examples are also the same.

Examples of each Z' are independently the same as examples of Z in formula (1), and preferred examples are also the same.

In formula (5), G₃ is preferably a 5- or 6-membered nitrogen-containing heterocyclic ring, and when G₃ represents a 5- or 6-membered nitrogen-containing aromatic heterocyclic ring, the ring is a monocyclic ring or a condensed ring. When further substitutable, G₃ may have a substituent or may be unsubstituted. G₃ is more preferably a substituted or unsubstituted 6-membered nitrogen-containing aromatic heterocyclic ring, and most preferably any one selected from the group of substituents represented by (3)-1 to (3)-6 in the following formula (3).

[Chem. 21]

Formula (3):

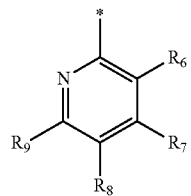
(3)-1

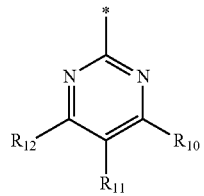
(3)-2

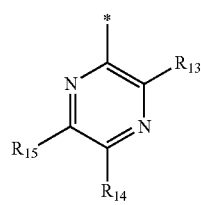
(3)-3

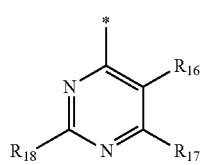
(3)-4

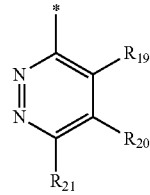
(3)-5

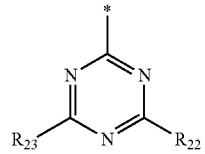
(3)-6

In formula (3), R₆ to R₂₃ each independently represents a hydrogen atom, a hydroxyl group, an amino group, a linear or branched alkyl group having a carbon number of 1 to 4, a cycloalkyl group having a carbon number of 5 to 8, an acyl group having a carbon number of 1 to 5, an alkenyl group having a carbon number of 2 to 4, an alkynyl group having a carbon number of 2 to 4, an alkyloxy group having a carbon number of 1 to 4, an alkylamino group having a carbon number of 1 to 8, an alkyloxycarbonyl group having a carbon number of 2 to 5, an amide group having a carbon number of 1 to 5, an aralkyl group having a carbon number of 7 to 10, a 5- to 8-membered saturated or unsaturated hydrocarbon ring or a 5- to 8-membered saturated or unsaturated heterocyclic ring. When R₆ to R₂₃ each represents a 5- to 8-membered saturated or unsaturated hydrocarbon ring or heterocyclic ring, the ring is a monocyclic ring or a condensed ring. R₆ to R₂₃ may have a substituent. R₆ to R₂₃ each is more preferably a hydrogen atom, a hydroxyl group, an amino group, a linear or branched alkyl group having a carbon number of 1 to 4, an acyl group having a carbon number of 1 to 5, an alkyloxy group having a carbon number of 1 to 4, an alkylamino group having a carbon number of 1 to 8, an alkyloxycarbonyl group having a carbon number of 2 to 5 or an amide group having a carbon number of 1 to 5, still more preferably a hydrogen atom, a hydroxyl group, an amino group, a methyl group, a methyloxy group, a methylamino group or an acetamide group.

R₆ to R₂₁ may form a bond with each other, and in this case, R₆ to R₂₁ each is preferably a nonmetallic atom group necessary for forming a 5- to 7-membered hydrocarbon ring or a 5- to 7-membered heterocyclic ring, more preferably for forming a 6-membered aromatic hydrocarbon ring or a 6-membered aromatic heterocyclic ring.

In formula (5), examples of the heterocyclic group represented by G₃ include, as set forth without limiting the substitution position, a pyridyl group, a pyrazinyl group, a pyridazinyl group, a pyrimidinyl group, a triazinyl group, a quinolinyl group, an isoquinolinyl, a quinazolinyl group, a cinnolinyl group, a phthalazinyl group, a quinoxalinyl group, a pyrrolyl group, an indolyl group, a furanyl group, a benzofuranyl group, a pyrazolyl group, an imidazolyl group, a benzimidazolyl group, a triazolyl group, an oxazolyl group, a benzoxazolyl group, a thiadiazolyl group, an isoxazolyl group, a benzisoxazolyl group, a pyrrolidinyl group, a piperidinyl group, a piperazinyl group, an imidazolidinyl group and a sulfolanyl group.

Among these, a pyridyl group, a pyrazinyl group, a pyrimidinyl group, a pyridazinyl group and a triazinyl group are preferred, and a pyridyl group, a pyrimidinyl group and a triazinyl group are more preferred.

As for the combination of preferred substituents in the pigment represented by formula (5) of the present invention, a compound where at least one of various groups is the above-described preferred group is preferred, a compound where a larger number of various groups are the above-described preferred groups is more preferred, and a compound where all groups are the above-described preferred groups is most preferred.

The particularly preferred combination as the azo pigment represented by formula (5) of the present invention includes the following (i) to (iv).

(i) $R'_1$ and $R'_2$ each is independently, preferably a hydrogen atom, a linear or branched alkyl group having a carbon number of 1 to 4, an alkenyl group having a carbon number of 2 to 4, an alkynyl group having a carbon number of 2 to 4, an aralkyl group having a carbon number of 7 to 9, a 5- to 8-membered saturated or unsaturated hydrocarbon ring group or a 5- to 8-membered saturated or unsaturated heterocyclic group. When either one of $R'_1$ and $R'_2$ represents a 5- to 8-membered saturated or unsaturated hydrocarbon ring group or a 5- to 8-membered saturated or unsaturated heterocyclic group, the ring is a monocyclic ring or a condensed ring, and when substitutable, $R'_1$ and $R'_2$ each may have a substituent or may be unsubstituted. $R'_1$ and $R'_2$ each is more preferably a hydrogen atom, a linear or branched alkyl group having a carbon number of 1 to 4, a 5- to 8-membered saturated or unsaturated hydrocarbon ring group or a 5- to 8-membered saturated or unsaturated heterocyclic group. When either one of $R'_1$ and $R'_2$ represents a 5- to 8-membered saturated or unsaturated hydrocarbon ring group or a 5- to 8-membered saturated or unsaturated heterocyclic group, the ring is a monocyclic ring or a condensed ring and when substitutable, $R'_1$ and $R'_2$ each may have a substituent or may be unsubstituted. In particular, $R'_1$ and $R'_2$ each is most preferably a methyl group, a tert-butyl group, a substituted or unsubstituted 5- or 6-membered aryl group or a substituted or unsubstituted 5- or 6-membered aromatic heterocyclic group.

(ii) Y' is preferably a hydrogen atom, a linear or branched alkyl group having a carbon number of 1 to 4, an alkenyl group having a carbon number of 2 to 4, an alkynyl group having a carbon number of 2 to 4, an aralkyl group having a carbon number of 7 to 9, a 5- to 8-membered saturated or unsaturated hydrocarbon ring group or a 5- to 8-membered saturated or unsaturated heterocyclic group. When Y' represents a 5- to 8-membered saturated or unsaturated hydrocarbon ring group or a 5- to 8-membered saturated or unsaturated heterocyclic group, the ring is a monocyclic ring or a condensed ring, and when substitutable, Y' may have a substituent or may be unsubstituted. Y' is more preferably a hydrogen atom, a linear or branched alkyl group having a carbon number of 1 to 4, a 5- to 8-membered saturated or unsaturated hydrocarbon ring group or a 5- to 8-membered saturated or unsaturated heterocyclic group. When Y' represents a 5- to 8-membered saturated or unsaturated hydrocarbon ring group or a 5- to 8-membered saturated or unsaturated heterocyclic group, the ring is a monocyclic ring or a condensed ring and when substitutable, Y' may have a substituent or may be unsubstituted. Y' is still more preferably a hydrogen atom, a methyl group, a tert-butyl group, a substituted or unsubstituted 6-membered aromatic hydrocarbon ring group or a substituted or unsubstituted 6-membered aromatic heterocyclic group.

(iii) Z' is preferably a cyano group, an acyl group having a carbon number of 2 to 6, an acyloxy group having a carbon number of 2 to 6, a carbamoyl group having a carbon number of 1 to 8, an alkyloxycarbonyl group having a carbon number of 2 to 8, an aryloxycarbonyl group having a carbon number of 7 to 12, a nitro group, an alkylsulfinyl group having a carbon number of 1 to 6, an arylsulfinyl group having a carbon number of 6 to 10, an alkylsulfonyl group having a carbon number of 1 to 6, an arylsulfonyl group having a carbon number of 6 to 10, a sulfamoyl group having a carbon number of 0 to 9, a halogenated alkyl group having a carbon number of 1 to 6, a halogenated aryl group having a carbon number of 1 to 6, a halogenated alkyloxy group having a carbon number of 1 to 6, a halogenated alkylthio group having a carbon number of 1 to 6, a halogenated aryloxy group having a carbon number of 6 to 12 or a 5- to 8-membered heterocyclic group, more preferably a cyano group, an alkyloxycarbonyl group having a carbon number of 2 to 8, an alkylsulfonyl group having a carbon number of 1 to 6, an arylsulfonyl group having a carbon number of 6 to 10 or a sulfamoyl group having a carbon number of 0 to 8, and most preferably a cyano group.

(iv) $G_3$ is preferably a 5- or 6-membered nitrogen-containing aromatic heterocyclic ring, and when $G_3$ represents a 5- or 6-membered nitrogen-containing aromatic heterocyclic ring, the ring is a monocyclic ring or a condensed ring. $G_3$ may have a substituent. $G_3$ is more preferably a substituted or unsubstituted 6-membered nitrogen-containing aromatic heterocyclic ring, and most preferably any one group selected from the group of monovalent substituents represented by (3)-1 to (3)-6 in formula (3).

In formula (3), $R_6$ to $R_{23}$ each is independently a hydrogen atom, a hydroxyl group, an amino group, a linear or branched alkyl group having a carbon number of 1 to 4, a cycloalkyl group having a carbon number of 5 to 8, an acyl group having a carbon number of 1 to 5, an alkenyl group having a carbon number of 2 to 4, an alkynyl group having a carbon number of 2 to 4, an alkyloxy group having a carbon number of 1 to 4, an alkylamino group having a carbon number of 1 to 8, an alkyloxycarbonyl group having a carbon number of 2 to 5, an amide group having a carbon number of 1 to 5, an aralkyl group having a carbon number of 7 to 10, a 5- to 8-membered saturated or unsaturated hydrocarbon ring or a 5- to 8-membered saturated or unsaturated heterocyclic ring. When $R_6$ to $R_{23}$ each represents a 5- to 8-membered saturated or unsaturated hydrocarbon ring or heterocyclic ring, the ring is a monocyclic ring or a condensed ring. $R_6$ to $R_{23}$ may have a substituent. $R_6$ to $R_{23}$ each is preferably a hydrogen atom, a hydroxyl group, an amino group, a linear or branched alkyl group having a carbon number of 1 to 4, an acyl group having a carbon number of 1 to 5, an alkyloxy group having a carbon number of 1 to 4, an alkylamino group having a carbon number of 1 to 8, an alkyloxycarbonyl group having a carbon number of 2 to 5 or an amide group having a carbon number of 1 to 5, more preferably a hydrogen atom, a hydroxyl group, an amino group, a methyl group, a methyloxy group, a methylamino group or an acetamide group.

$R_6$ to $R_{21}$ may form a bond with each other, and in this case, $R_6$ to $R_{21}$ each is preferably a nonmetallic atom group necessary for forming a 5- to 7-membered hydrocarbon ring or a 5- to 7-membered heteroatom ring, more preferably a nonmetallic atom group necessary for forming a 6-membered aromatic hydrocarbon ring or a 6-membered aromatic heteroatom ring.

Tautomers of the azo pigment represented by formula (5) are also included in the scope of the present invention. Formula (5) is shown in the form of a canonical formula out of several kinds of tautomers possible in terms of chemical structure, but the pigment may be a tautomer other than the structure shown, and a mixture containing a plurality of kinds of tautomers may also be used. For example, the pigment represented by formula (5) is considered to have an azo-hydrazone tautomer represented by the following formula (51).

The compound represented by the following formula (5'), which is a tautomer of the azo pigment represented by formula (5), is also included in the scope of the present invention.

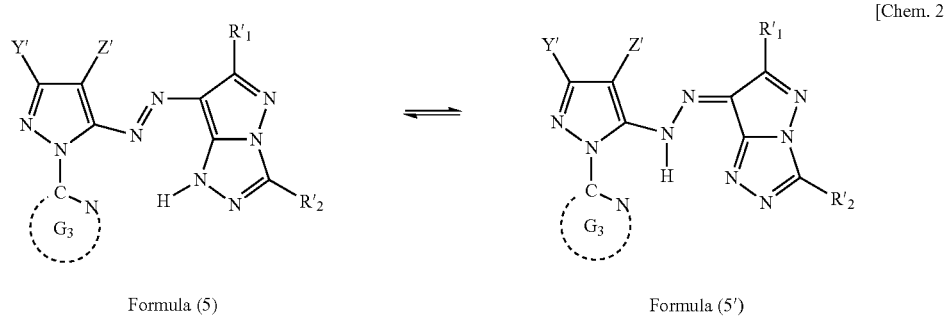

Formula (5)            Formula (5')

(wherein in formula (5'), R'$_1$, R'$_2$, Y', Z' and G$_3$ have the same meanings as in formula (5)).

The azo pigment represented by formula (2) is preferably an azo pigment represented by the following formula (6).

The azo pigment represented by formula (6), its tautomer and a salt or hydrate thereof are described in detail below.

Formula (6):

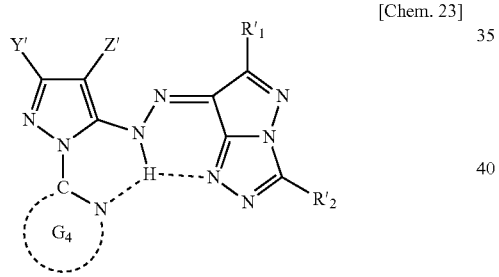

[Chem. 23]

(wherein R'$_1$, R'$_2$, Y' and Z' each independently has the same meaning as R'$_1$, R'$_2$, Y' and Z' in formula (5), and preferred combinations are also the same; and G$_4$ represents a nonmetallic atom group for forming a 6-membered nitrogen-containing aromatic heterocyclic group, and the heterocyclic ring may be a monocyclic ring or a condensed ring).

The azo pigments represented by formulae (1), (2), (4), (5) and (6) are considered to have an azo-hydrazone tautomer. Out of the azo pigments represented by formulae (1), (2), (4), (5) and (6); as described above, examples of the formula of the particularly preferred azo pigment include the azo pigment represented by formula (6).

This structure is preferred because a nitrogen atom, a hydrogen atom and a heteroatom (an oxygen atom of the carbonyl group or a nitrogen atom of the amino group) constituting the heterocyclic ring contained in the azo pigment structure as shown in formula (6) are liable to easily form at least one or more intramolecular cross-hydrogen bonds (intramolecular hydrogen bonds), which brings about an increase in the molecular planarity, in the intramolecular/intermolecular interaction and in the crystallinity of the azo pigment represented by formula (6) (a high-order structure becomes to be readily formed). As a result, the light fastness, thermal stability, wet heat stability, water resistance, gas resistance and/or solvent resistance, which are performances required of the pigment, are greatly enhanced and therefore, this structure is most preferred.

The present invention also relates to an azo compound represented by formula (2), its tautomer and a salt or hydrate thereof.

Formula (2):

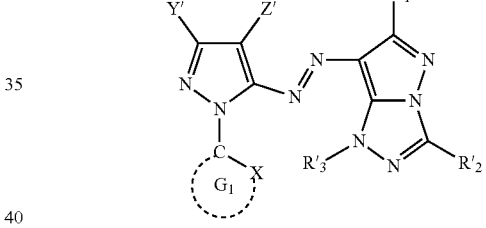

[Chem. 23]

(wherein R'$_1$, R'$_2$ and Y' each independently represents a hydrogen atom, a linear or branched alkyl group having a carbon number of 1 to 4, an alkenyl group having a carbon number of 2 to 4, an alkynyl group, having a carbon number of 2 to 4, an acyl group having a carbon number of 1 to 5, an aralkyl group having a carbon number of 7 to 9, a 5- to 8-membered saturated or unsaturated hydrocarbon ring group, or a 5- to 8-membered saturated or unsaturated heterocyclic group; R'$_3$ represents a hydrogen atom or a monovalent substituent; Z' represents an electron-withdrawing group having a Hammett's σp value of 0.2 or more; X represents a heteroatom at the position adjacent to the carbon atom bonded to the pyrazole ring; G$_1$ represents an atomic group for forming a 5- to 8-membered saturated or unsaturated heterocyclic ring; when any one of R'$_1$, R'$_2$, R'$_3$, Y' and G$_1$ represents a 5- to 8-membered saturated or unsaturated heterocyclic ring, the ring is a monocyclic ring or a condensed ring; and when any one of R'$_1$, R'$_2$, R'$_3$, Y' and G$_1$ represents a 5-membered unsaturated heterocyclic ring, the ring contains two or more nitrogen atoms therein).

Examples of the substituents and preferred combinations of substituents in the azo compound represented by formula (2) of the present invention are the same as those described for the azo pigment represented by formula (2).

In the azo compound represented by formula (2), $G_1$ in formula (2) is preferably any one selected from the group of substituents represented by the following formula (3)-1 to (3)-6:

[Chem. 25]

Formula (3):

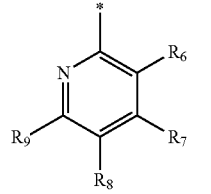
(3)-1

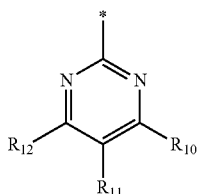
(3)-2

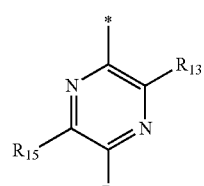
(3)-3

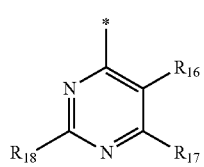
(3)-4

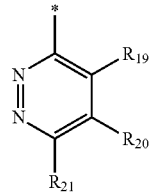
(3)-5

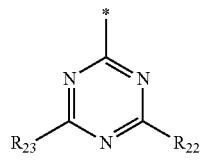
(3)-6

(wherein $R_6$ to $R_{23}$ each independently represents a hydrogen atom or a substituent, and $R_6$ to $R_{21}$ may combine with each other to form a ring).

In the azo compound represented by formula (2), examples of the group of substituents represented by formula (3)-1 to (3)-6 and preferred combinations of substituents are the same as those described for formulae (3)-1 to (3)-6 in the azo pigment represented by formula (2).

The present invention also relates to an azo compound represented by formula (4), its tautomer and a salt or hydrate thereof.

Formula (4):

[Chem. 26]

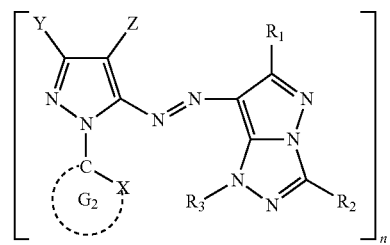

(wherein n, $R_1$, $R_2$, $R_3$, Y and Z each independently has the same meaning as n, $R_1$, $R_2$, $R_3$, Y or Z in formula (1); X represents a heteroatom at the position adjacent to the carbon atom bonded to the pyrazole ring; $G_2$ represents an atomic group for forming a 5- to 8-membered saturated or unsaturated heterocyclic ring; the formula represents a dimer through $R_1$, $R_2$, $R_3$, Y, Z or $G_2$ when n is 2, represents a trimer through $R_1$, $R_2$, $R_3$, Y, Z or $G_2$ when n is 3, and represents a tetramer through $R_1$, $R_2$, $R_3$, Y, Z or $G_2$ when n is 4; and when any one of $R_1$, $R_2$, $R_3$, Y and $G_2$ represents a 5- to 8-membered saturated or unsaturated heterocyclic ring, the ring is a monocyclic ring or a condensed ring).

Examples of the substituents and preferred combinations of substituents in the azo compound represented by formula (4) of the present invention are the same as those described for the azo pigment represented by formula (4).

In the azo compound represented by formula (4), $G_2$ in formula (4) is preferably any one group selected from the group of monovalent to trivalent substituents represented by (3)-1 to (3)-6 in the following formula (3):

[Chem. 27]

Formula (3):

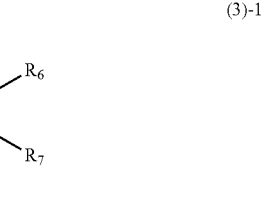
(3)-1

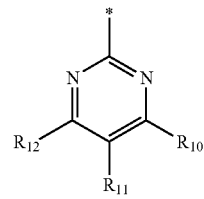
(3)-2

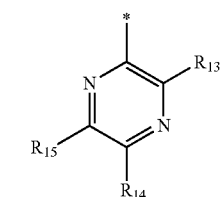
(3)-3

(3)-4

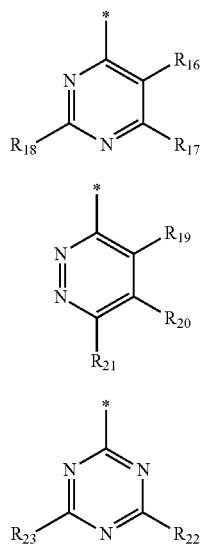

(3)-5

(3)-6

(wherein $R_6$ to $R_{23}$ each independently represents a hydrogen atom or a substituent, and $R_6$ to $R_{21}$ may combine with each other to form a ring).

In the azo compound represented by formula (4), examples of the group of substituents represented by formula (3)-1 to (3)-6 and preferred combinations of substituents are the same as those described for formulae (3)-1 to (3)-6 in the azo pigment represented by formula (4).

Examples of the salt, hydrate and tautomerism of the azo compounds represented by formulae (2) and (4) of the present invention are the same as those of the salt, hydrate and tautomerism of the azo dyes of the present invention.

The novel azo compound of the present invention is useful as an azo pigment. Also, the dispersion of the present invention preferably contains at least one member of a tautomer of the azo compound represented by formula (2) or (4) and a salt or hydrate thereof.

Specific examples of the azo pigments represented by formulae (1), (2), (4), (5) and (6), the pigment dispersion and the azo compounds represented by formulae (2) and (4) are set forth below, but the azo pigment, pigment dispersion and azo compound for use in the present invention are not limited to the following examples.

In the following, specific examples are shown in the form of a canonical formula out of several kinds of tautomers possible in terms of chemical structure, but these may be a tautomer structure other than the structures shown below.

[Chem. 28]

(2)-1

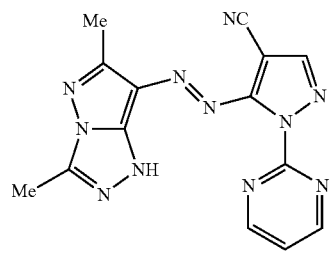

(2)-2

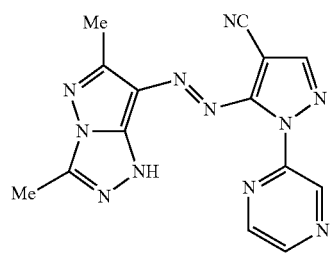

(2)-3

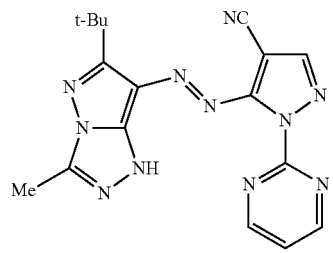

(2)-4

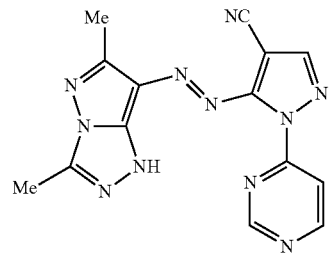

(2)-5

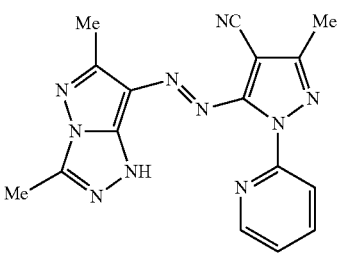

(2)-6

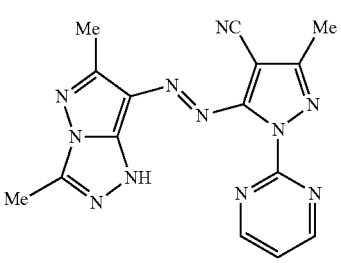

(2)-7

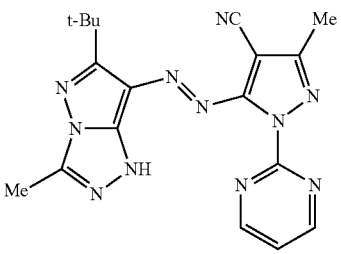

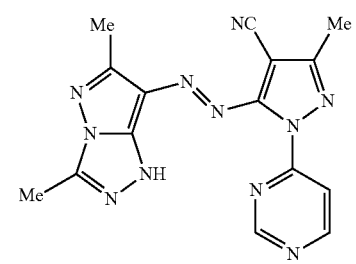
(2)-8
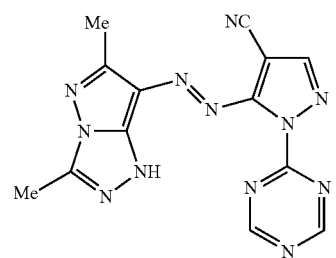
(2)-9
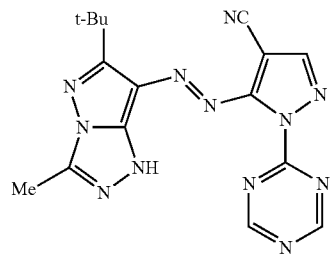
(2)-10
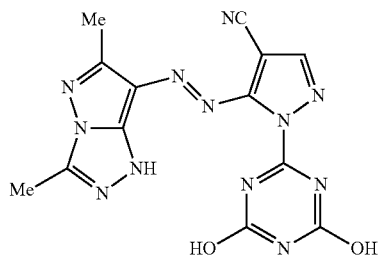
(2)-11
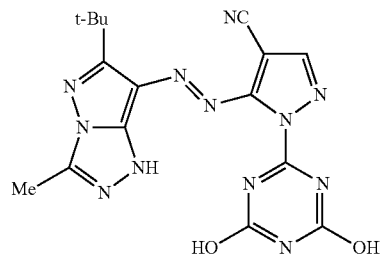
(2)-12
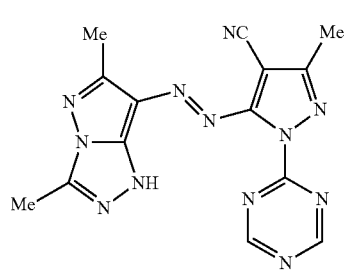
(2)-13
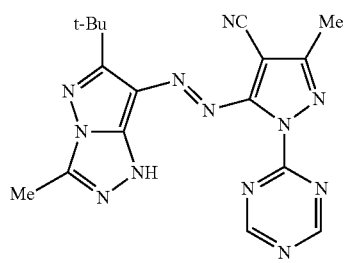
(2)-14
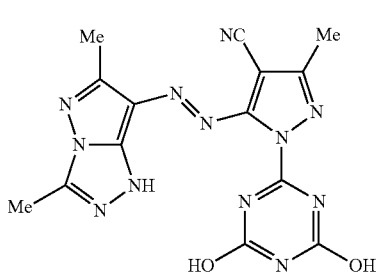
(2)-15
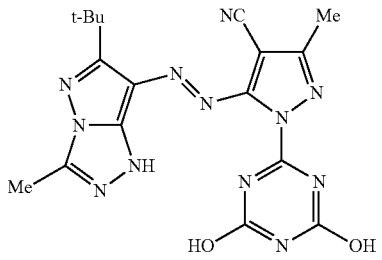
(2)-16
[Chem. 29]
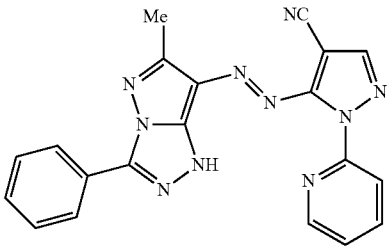
(2)-17
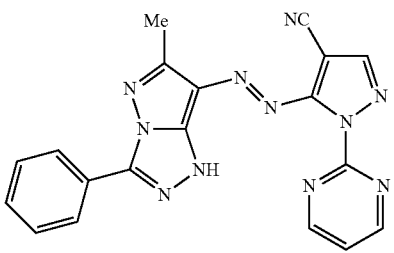
(2)-18
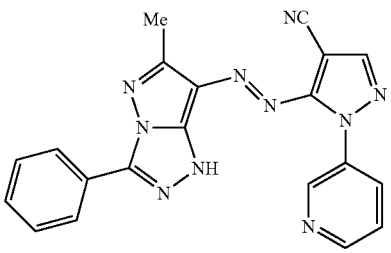
(2)-19

(2)-20
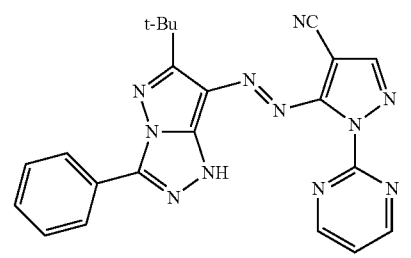
(2)-21
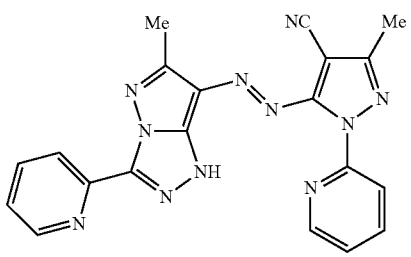
(2)-22
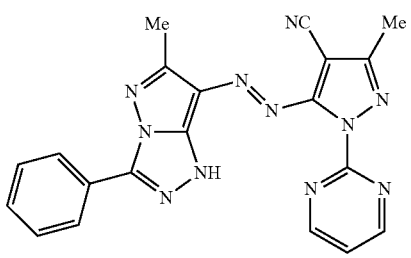
(2)-23
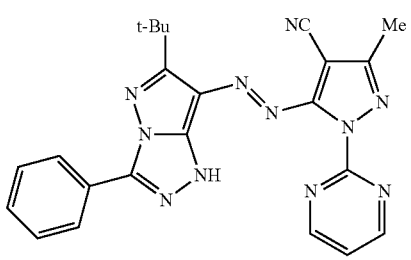
(2)-24
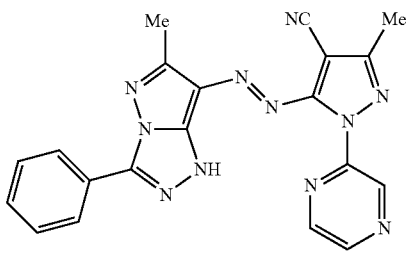
(2)-25
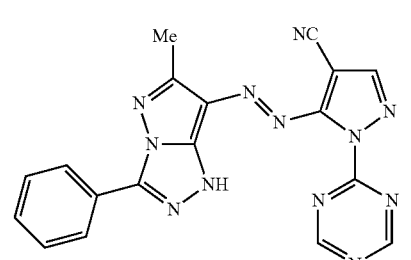
(2)-26
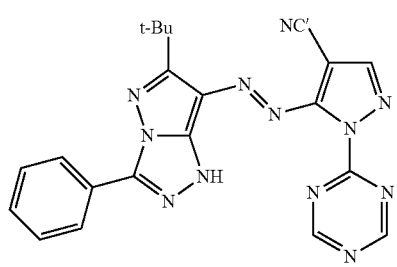
(2)-27
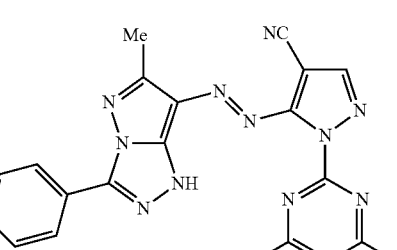
(2)-28
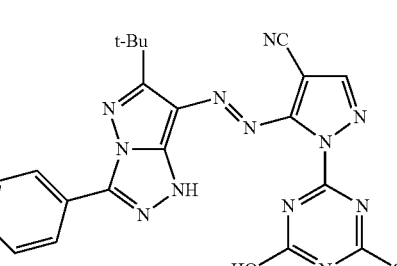
(2)-29
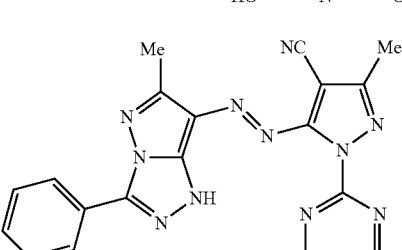
(2)-30
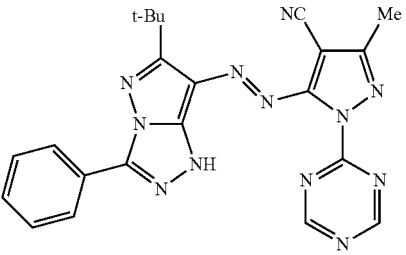
(2)-31
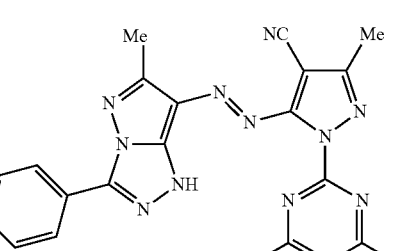

-continued
(2)-32
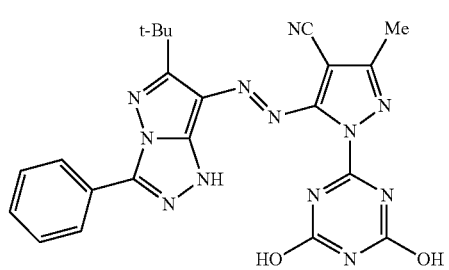
(2)-33
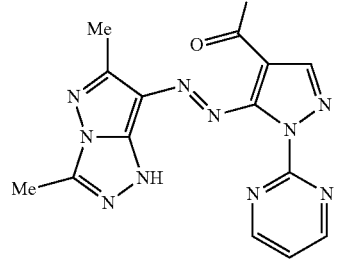
(2)-34
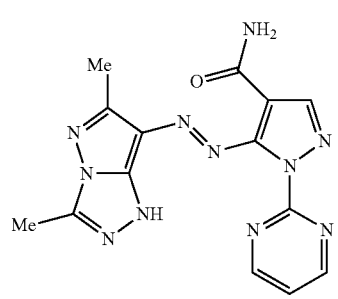
(2)-35
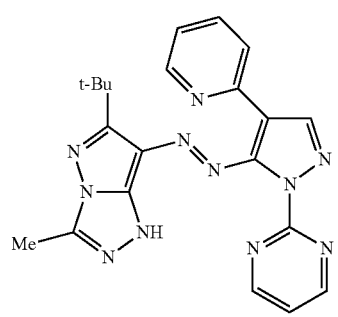
(2)-36
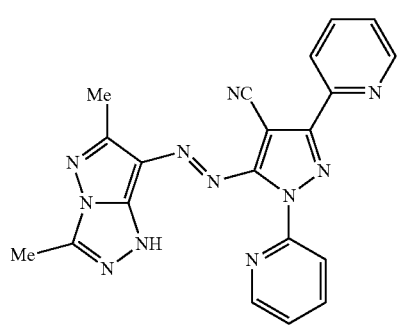
-continued
(2)-37
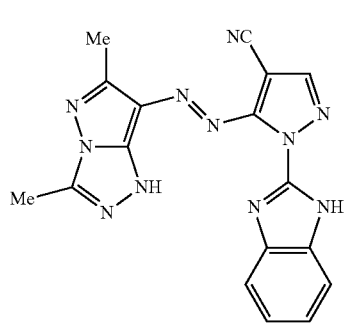
(2)-38
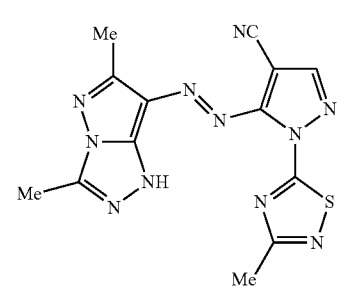
(2)-39
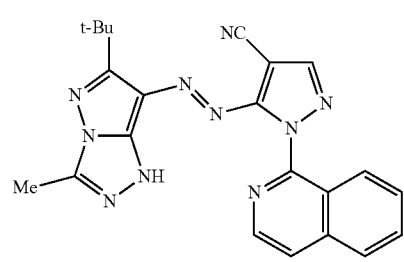
(2)-40
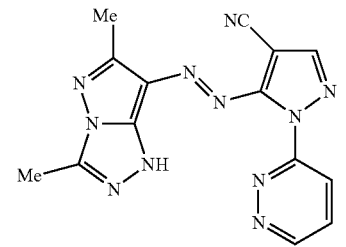
(2)-41
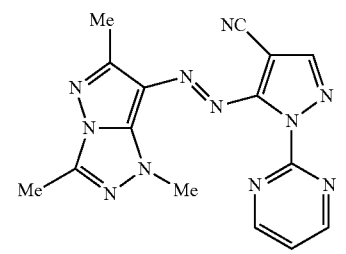
(2)-42
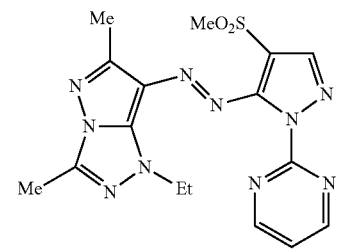

(2)-43
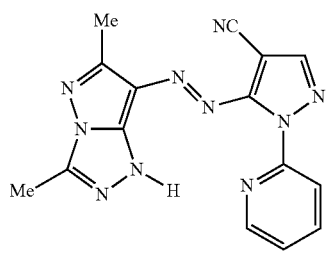
[Chem. 30]
(1)-33
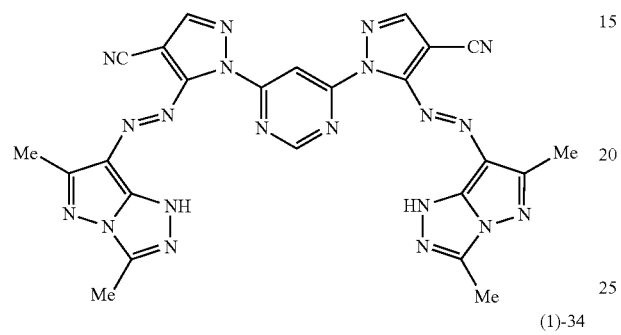
(1)-34
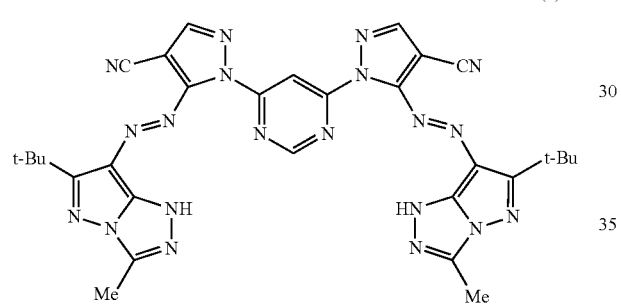
(1)-35
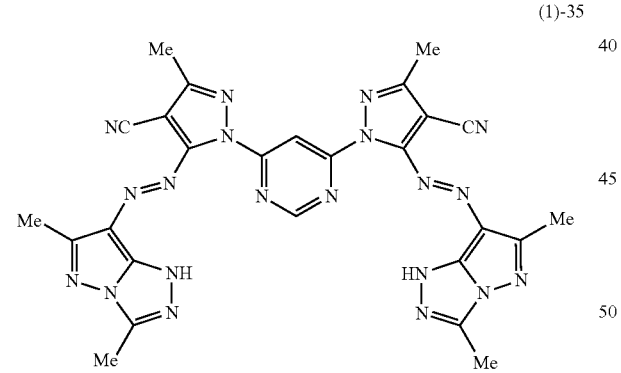
(1)-36
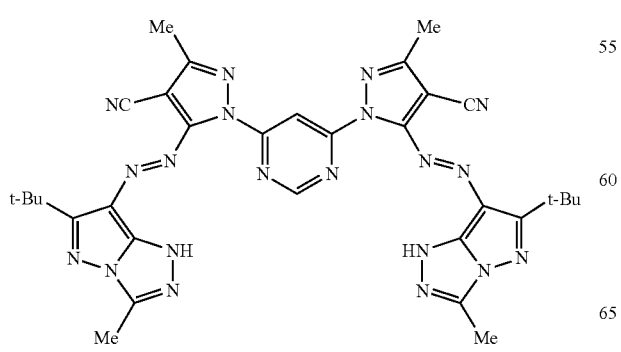
(1)-37
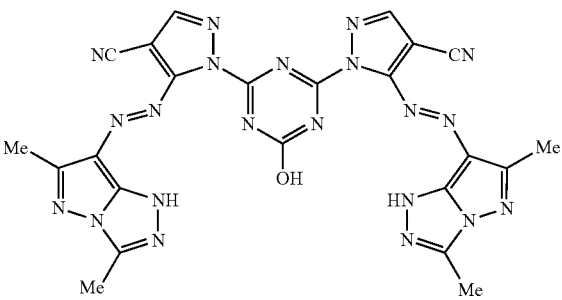
(1)-38
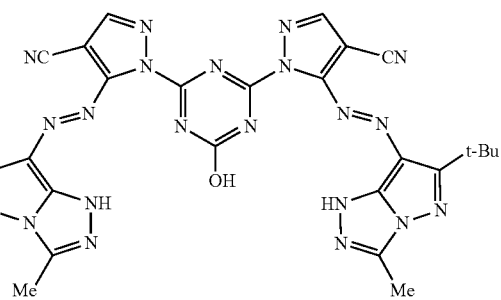
(1)-39
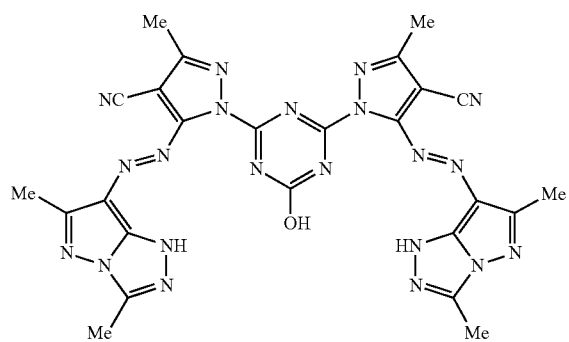
(1)-40
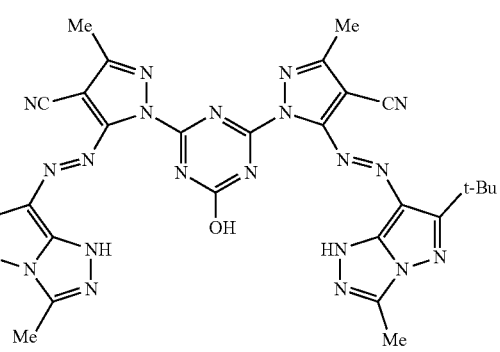

(1)-41

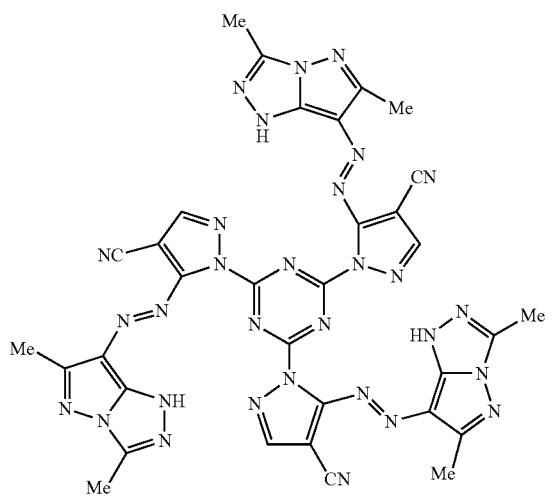

(1)-42

(1)-43

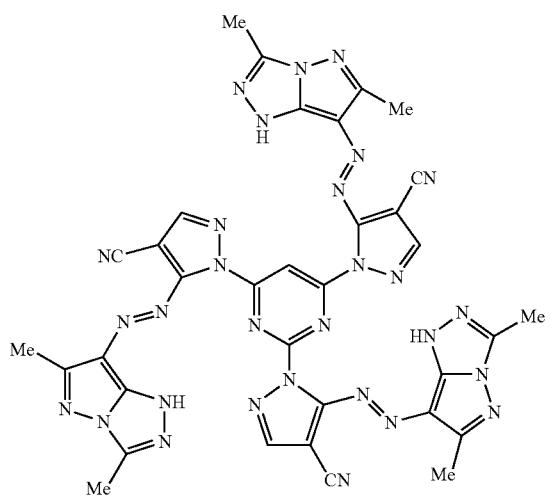

(1)-44

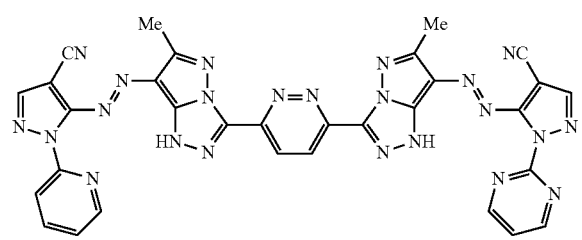

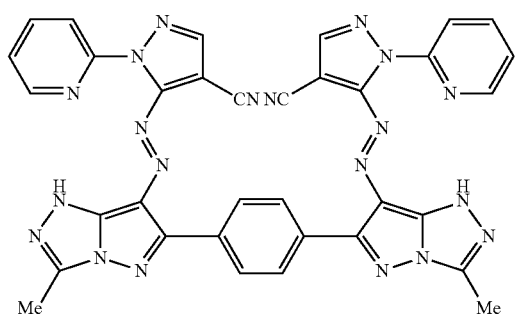

(1)-45

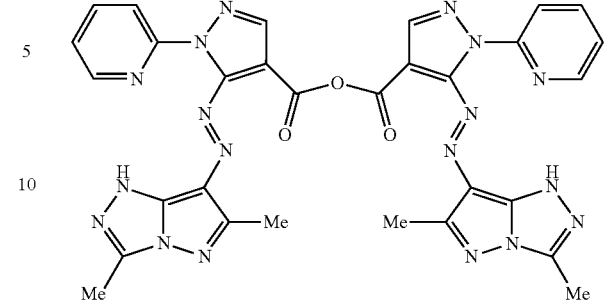

The pigments represented by formula (1), (2), (4), (5) and (6) of the present invention may be sufficient if the chemical formula thereof is formula (1), (2), (4), (5) or (6) or a tautomer thereof, and the pigment may be in any crystal morphology called polymorphs.

Crystalline polymorphs have the same chemical composition but a different arrangement of building blocks (molecules or ions) in the crystal. The crystal structure determines chemical and physical properties, and individual polymorphs can be distinguished by the rheology, color and other coloristic properties. Also, different crystalline polymorphs can be identified by X-Ray Diffraction (results of powder X-ray diffractometry) or X-Ray Analysis (results of X-ray crystal structure analysis). In the case where the pigments represented by formulae (1), (2), (4), (5) and (6) of the present invention each has crystalline polymorphs, the pigment may be any polymorph or may be a mixture of two or more polymorphs, but the main component is preferably a pigment having a single crystal form. That is, a pigment where crystalline polymorphs are not mixed is preferred. The content of the azo pigment having a single crystal form is from 70 to 100%, preferably from 80 to 100%, more preferably from 90 to 100%, still more preferably from 95 to 100%, yet still more preferably 100%, based on the entire azo pigment. When the main component is an azo pigment having a single crystal form, regularity in the colorant molecular arrangement is enhanced and the intramolecular/intermolecular interaction is strengthened to facilitate the formation of a high-order three-dimensional network, which yields preferred results in view of performances required of the pigment, such as enhanced hue, light fastness, heat fastness, humidity fastness, oxidative gas fastness and solvent resistance.

The mixing ratio of crystalline polymorphs in the azo pigment can be confirmed by the value in physicochemical measurement of a solid, such as X-ray single crystal structural analysis, powder X-ray diffraction (XRD), micrograph of crystal (TEM) and IR (KBr method).

The above-described tautomers and/or crystalline polymorphs can be controlled by the production conditions at the coupling reaction.

In the present invention, when the azo pigments represented by formula (1), (2), (4), (5) and (6) have an acid radical, the acid radicals may be partially or entirely in a salt form, and a salt-type pigment and a free acid-type pigment may be mixed. Examples of the salt form include a salt of an alkali metal such as Na, Li and K, a salt of an ammonium which may be substituted with an alkyl group or a hydroxyalkyl group, and a salt of an organic amine. Examples of the organic amine include a lower alkylamine, a hydroxy-substituted lower alkylamine, a carboxy-substituted lower alkylamine, and a polyamine containing from 2 to 10 alkyleneimine units having a carbon number of 2 to 4. In the case of such a salt form, the number of kinds thereof is not limited to one, and a plurality of kinds of salt forms may be mixed. Examples of the salt form include a salt of an alkali metal such as Na, Li and K, a salt of an ammonium which may be substituted with an alkyl group or a hydroxyalkyl group, and a salt of an organic amine. Examples of the organic amine include a lower alkylamine, a hydroxy-substituted lower alkylamine, a carboxy-substituted lower alkylamine, and a polyamine containing from 2 to 10 alkyleneimine units having a carbon number of 2 to 4. In the case of such a salt form, the number of kinds thereof is not limited to one, and a plurality of kinds of salt forms may be mixed.

Furthermore, in the structure of the pigment for use in the present invention, when a plurality of acid radicals are contained in one molecule, the plurality of acid radicals may be in a salt form or an acid form or may be different from each other.

In the present invention, the azo pigments represented by formulae (1), (2), (4), (5) and (6) may be a hydrate containing water molecules in the crystal.

The synthesis of the azo pigment of the present invention is described in detail below.

The azo pigment of the present invention can be synthesized, for example, by a coupling reaction between a diazonium salt of a diazo component of formula (7) prepared by a known method and a coupling component of formula (8).

Formula (7):

[Chem. 31]

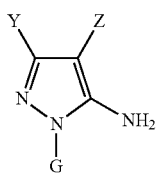

In formula (7), Y, Z and G have the same meanings as Y, Z and G in formula (1), respectively.

Formula (8):

[Chem. 32]

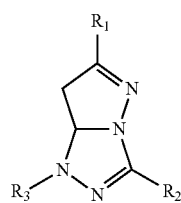

In formula (8), $R_1$, $R_2$ and $R_3$ have the same meanings as $R_1$, $R_2$ and $R_3$ in formula (1), respectively.

As for the heterocyclic amine (diazo component) represented by the amino form of formula (7), some may be commercially available, but the component can be generally produced by a conventionally known method, for example, by the method described in Japanese Patent 4,022,271. The reaction for forming a diazonium salt of the heterocyclic amine can be performed by reacting the heterocyclic amine with a reagent such as sodium nitrite, nitrosylsulfuric acid and isoamyl nitrite in an acidic solvent such as sulfuric acid, phosphoric acid and acetic acid at a temperature of 15° C. or less for approximately from 10 minutes to 6 hours. The coupling reaction can be performed by reacting the diazonium salt obtained by the method above with a compound represented by formula (8) at 40° C. or less, preferably 25° C. or less, for approximately from 10 minutes to 12 hours.

In the case where n in formulae (1) and (4) is 2 or more, the pigment can be synthesized in the same manner as in the scheme above by using a raw material prepared by introducing a substitutable divalent, trivalent or tetravalent substituent into $R_1$ to $R_3$, Y, Z, G or the like of formula (7) or (8).

In the thus-obtained reaction solution, a crystal is sometimes precipitated, but in general, after adding water or an alcohol-based solvent to precipitate a crystal, the crystal can be collected by filtration. Also, an alcohol-based solvent, water or the like may be added to the reaction solution to precipitate a crystal, and the precipitated crystal can be collected by filtration. The crystal collected by filtration is, if desired, washed and dried, whereby the azo pigment represented by formula (1) can be obtained.

As for the synthesis methods of formulae (2), (5) and (6), in the description above, Y, Z and G in formula (7) are read as Y', Z' and $G_1$ (or $G_3$ or $G_4$), respectively, and at the same time, $R_1$, $R_2$ and $R_3$ in formula (8) are read as $R'_1$, $R'_2$ and $R'_3$, respectively (here, $R_1$, $R'_2$, $R'_3$, Y', Z', $G_1$, $G_3$ and $G_4$ have the same meaning as $R'_1$, $R'_2$, $R'_3$, Y', Z', $G_1$, $G_3$ and $G_4$ in formulae (2), (5) and (6), respectively).

The compounds represented by formulae (1), (2), (4), (5) and (6) are obtained as a crude pigment by the above-described production process, but in the case of using it as the pigment dispersion of the present invention, a post-treatment is preferably performed. Examples of the post-treatment include a process of controlling the pigment particle by a milling treatment such as solvent salt milling, salt milling, dry milling, solvent milling and acid pasting or by a solvent heating treatment, and a process of treating the surface with a resin, a surfactant or a dispersant.

The post-treatment of the compounds represented by formulae (1), (2), (4), (5) and (6) of the present invention is preferably a solvent heating treatment. Examples of the solvent used for the solvent heating treatment include water, an aromatic hydrocarbon-based solvent such as toluene and xylene, a halogenated hydrocarbon-based solvent such as chloroform, chlorobenzene and o-dichlorobenzene, an alcohol-based solvent such as methanol, ethanol, isopropanol and isobutanol, a polar aprotic organic solvent such as N,N-dimethylformamide, N,N-dimethylacetamide and N-methyl-2-pyrrolidone, glacial acetic acid, pyridine and a mixture thereof. The average particle diameter of the pigment is preferably adjusted to be from 0.01 μm to 1 μm by such a post-treatment.

The compounds represented by formulae (1), (2), (4), (5) and (6) are obtained as a crude azo pigment (crude) by the above-described production process, but in the case of using it as the pigment of the present invention, a post-treatment is preferably performed. Examples of the post-treatment include a process of controlling the pigment particle by a milling treatment such as solvent salt milling, salt milling, dry milling, solvent milling and acid pasting or by a solvent heating treatment, and a process of treating the surface with a resin, a surfactant or a dispersant.

As for the post-treatment of the compounds represented by formulae (1), (2), (4), (5) and (6) of the present invention, solvent heating treatment and/or solvent salt milling are preferably performed.

Examples of the solvent used for the solvent heating treatment include water, an aromatic hydrocarbon-based solvent such as toluene and xylene, a halogenated hydrocarbon-based solvent such as chlorobenzene and o-dichlorobenzene, an alcohol-based solvent such as isopropanol and isobutanol, a polar aprotic organic solvent such as N,N-dimethylformamide, N,N-dimethylacetamide and N-methyl-2-pyrrolidone, glacial acetic acid, pyridine and a mixture thereof. In the solvent described above, an inorganic or organic acid or base may be further added. The temperature of the solvent heating treatment varies depending on the desired primary particle diameter of the pigment but is preferably from 40 to 150° C., more preferably from 60 to 100° C. Also, the treating time is preferably from 30 minutes to 24 hours.

In the solvent salt milling, for example, the crude azo pigment, an inorganic salt and an organic solvent incapable of dissolving these are charged into a kneading machine and kneading milling is performed therein. As for the inorganic salt, a water-soluble inorganic salt can be suitably used and, for example, an inorganic salt such as sodium chloride, potassium chloride and sodium sulfate is preferably used. Use of an inorganic salt having an average particle diameter of 0.5 to 50 µm is more preferred. The amount of the inorganic salt used is preferably from 3 to 20 times by mass, more preferably from 5 to 15 times by mass, based on the crude azo pigment. As for the organic solvent, a water-soluble organic solvent can be suitably used and in view of safety, a high boiling point solvent is preferred, because the solvent enters an evaporable state due to rise in the temperature during kneading. Examples of such an organic solvent include diethylene glycol, glycerin, ethylene glycol, propylene glycol, liquid polyethylene glycol, liquid polypropylene glycol, 2-(methoxymethoxy)ethanol, 2-butoxyethanol, 2-(isopentyloxy)ethanol, 2-(hexyloxy)ethanol, diethylene glycol monomethyl ether, diethylene glycol monoethyl ether, diethylene glycol monobutyl ether, triethylene glycol, triethylene glycol monomethyl ether, 1-methoxy-2-propanol, 1-ethoxy-2-propanol, dipropylene glycol, dipropylene glycol monomethyl ether, dipropylene glycol monomethyl ether, dipropylene glycol, and a mixture thereof. The amount of the water-soluble organic solvent used is preferably from 0.1 to 5 times by mass based on the crude azo pigment. The kneading temperature is preferably from 20 to 130° C., more preferably from 40 to 110° C. Examples of the kneading machine which can be used include a kneader and a mix-muller.

[Pigment Dispersion]

The pigment dispersion of the present invention contains at least one member of azo pigments represented by formulae (1), (2), (4), (5) and (6), their tautomers, and salts or hydrates thereof. Thanks to this configuration, the pigment dispersion can be a pigment dispersion excellent in the coloristic characteristics, durability and dispersion stability.

The pigment dispersion of the present invention may be aqueous or non-aqueous but is preferably an aqueous pigment dispersion. In the aqueous pigment dispersion of the present invention, the aqueous liquid used for dispersing the pigment therein may be a mixture of water as the main component and a hydrophilic organic solvent added, if desired. Examples of the hydrophilic organic solvent include alcohols such as methanol, ethanol, propanol, isopropanol, butanol, isobutanol, sec-butanol, tert-butanol, pentanol, hexanol, cyclohexanol and benzyl alcohol, polyhydric alcohols such as ethylene glycol, diethylene glycol, triethylene glycol, polyethylene glycol, propylene glycol, dipropylene glycol, polypropylene glycol, butylene glycol, hexanediol, pentanediol, glycerin, hexanetriol and thiodiglycol, glycol derivatives such as ethylene glycol monomethyl ether, ethylene glycol monoethyl ether, ethylene glycol monobutyl ether, diethylene glycol monomethyl ether, diethylene glycol monobutyl ether, propylene glycol monomethyl ether, propylene glycol monobutyl ether, dipropylene glycol monomethyl ether, triethylene glycol monomethyl ether, ethylene glycol diacetate, ethylene glycol monomethyl ether acetate triethylene glycol monoethyl ether and ethylene glycol monophenyl ether, amines such as ethanolamine, diethanolamine, triethanolamine, N-methyldiethanolamine, N-ethyldiethanolamine, morpholine, N-ethylmorpholine, ethylenediamine, diethylenetriamine, triethylenetetramine, polyethyleneimine and tetramethylpropylenediamine, formamide, N,N-dimethylformamide, N,N-dimethylacetamide, dimethylsulfoxide, sulfo lane, 2-pyrrolidone, N-methyl-2-pyrrolidone, N-vinyl-2-pyrrolidone, 2-oxazolidone, 1,3-dimethyl-2-imidazolidinone, acetonitrile and acetone.

The aqueous pigment dispersion of the present invention may contain an aqueous resin. The aqueous resin includes a water-soluble resin capable of dissolving in water, a water-dispersible resin capable of dispersing in water, a colloidal dispersion resin, and a mixture thereof. Specific examples of the aqueous resin include acryl-based, styrene-acryl-based, polyester-based, polyamide-based, polyurethane-based and fluorine-based resins.

For enhancing the dispersion of the pigment and the picture quality of the image, a surfactant and a dispersant may be used. The surfactant includes anionic, nonionic, cationic and amphoteric surfactants, and any surfactant may be used, but an anionic or nonionic surfactant is preferably used. Examples of the anionic surfactant include a fatty acid salt, an alkylsulfuric ester salt, an alkylbenzenesulfonate, an alkylnaphthalenesulfonate, a dialkylsulfosuccinate, an alkyldiaryl ether disulfonate, an alkyl phosphate, a polyoxyethylene alkyl ether sulfate, a polyoxyethylene alkylaryl ether sulfate, a naphthalenesulfonic acid formalin condensate, a polyoxyethylene alkylphosphoric ester salt, a glycerol borate fatty acid ester and a polyoxyethylene glycerol fatty acid ester.

Examples of the nonionic surfactant include a polyoxyethylene alkyl ether, a polyoxyethylene alkylaryl ether, a polyoxyethylene oxypropylene block copolymer, a sorbitan fatty acid ester, a polyoxyethylene sorbitan fatty acid ester, a polyoxyethylene sorbitol fatty acid ester, a glycerin fatty acid ester, a polyoxyethylene fatty acid ester, a polyoxyethylene alkylamine, and fluorine-containing and silicon-containing surfactants.

The non-aqueous pigment dispersion is obtained by dispersing the pigment represented by formula (1), (2), (4), (5) or (6) in a non-aqueous vehicle. Examples of the resin used for the non-aqueous vehicle include petroleum resin, casein, shellac, rosin-modified maleic acid resin, rosin-modified phenol resin, nitrocellulose, cellulose acetate butyrate, cyclized rubber, chlorinated rubber, oxidized rubber, hydrochlorinated rubber, phenol resin, alkyd resin, polyester resin, unsaturated polyester resin, amino resin, epoxy resin, vinyl resin, vinyl chloride, vinyl chloride-vinyl acetate copolymer, acrylic resin, methacrylic resin, polyurethane resin, silicon resin, fluororesin, drying oil, synthetic drying oil, styrene/maleic acid resin, styrene/acrylic resin, polyamide resin, polyimide resin, benzoguanamine resin, melamine resin, urea resin chlorinated polypropylene, butyral resin and vinylidene chloride resin. A photocurable resin may also be used as the non-aqueous vehicle.

Examples of the solvent used for the non-aqueous vehicle include an aromatic solvent such as toluene, xylene and methoxybenzene, an acetic acid ester-based solvent such as ethyl acetate, butyl acetate, propylene glycol monomethyl ether acetate and propylene glycol monoethyl ether acetate, a propionate-based solvent such as ethoxyethyl propionate, an alcohol-based solvent such as methanol and ethanol, an ether-based solvent such as butyl cellosolve, propylene glycol monomethyl ether, diethylene glycol ethyl ether and diethylene glycol dimethyl ether, a ketone-based solvent such as methyl ethyl ketone, methyl isobutyl ketone and cyclohexanone, an aliphatic hydrocarbon-based solvent such as hexane, a nitrogen compound-based solvent such as N,N-dimethylformamide, N,N-dimethylacetamide, γ-butyrolactam, N-methyl-2-pyrrolidone, aniline and pyridine, a lactone-based solvent such as γ-butyrolactone, and a carbamic acid ester such as a 48:52 mixture of methyl carbamate and ethyl carbamate.

The pigment dispersion of the present invention is obtained by dispersing the above-described azo pigment and an aqueous or non-aqueous medium by means of a dispersing device. Examples of the dispersing device which can be used include a ball mill, a sand mill, a bead mill, a roll mill, a jet mill, an attritor, an ultrasonic disperser and a disperser.

In the present invention, the volume average particle diameter of the pigment contained in the pigment dispersion is preferably from 10 nm to 250 nm. Incidentally, the volume average particle diameter of the pigment particle indicates the particle diameter of the pigment itself or when an additive such as dispersant is attached to the color material, the diameter of the particle to which the additive is attached. In the present invention, the device used for measuring the volume average particle diameter of the pigment was a Nanotrac UPA particle size distribution analyzer (UPA-EX150, manufactured by Nikkiso Co., Ltd.). The measurement was performed according to the predetermined measurement method after placing 3 ml of the pigment dispersion in the measurement cell. In this connection, as for the parameter input at the measurement, the ink viscosity was used for the viscosity, and the pigment density was used for the density of dispersed particles.

The volume average particle diameter is more preferably from 20 nm to 250 nm, still more preferably from 20 nm to 230 nm. If the number average particle diameter of the particles in the pigment dispersion is less than 10 nm, the storage stability cannot be ensured in some cases, whereas if it exceeds 250 nm, the optical density is sometimes decreased.

The concentration of the pigment contained in the pigment dispersion of the present invention is preferably from 1 to 35 mass %, more preferably from 2 to 25 mass %. If the concentration is less than 1 mass %, a sufficient image density may not be obtained when using the pigment dispersion alone as an ink, whereas if the concentration exceeds 35 mass %, the dispersion stability is sometimes decreased.

The dispersion containing the azo compound of the present invention may similarly contain the above-described components constituting the pigment dispersion, and the preferred concentration of the azo compound contained in the dispersion is also the same as that described for the pigment dispersion.

The usage of the azo pigment and azo compound of the present invention includes an image recording material for forming an image, particularly a color image, and specific examples thereof include an inkjet recording material described later in detail, a heat-sensitive recording material, a pressure-sensitive recording material, a recording material using an electrophotographic system, a transfer silver halide light-sensitive material, a printing ink, and a recording pen. Among these, an inkjet recording material, a heat-sensitive recording material and a recording material using an electrophotographic system are preferred, and an inkjet recording material is more preferred.

Also, the azo pigment and azo compound of the present invention are applicable to a color filter for recording and reproducing a color image, which is used in a solid imaging device such as CCD or in a display such as LCD or PDP, or to a dyeing solution for dyeing various fibers.

[Coloring Composition]

The coloring composition of the present invention means a coloring composition containing at least one kind of the azo pigment or azo compound of the present invention. The coloring composition of the present invention may contain a medium and when a solvent is used as the medium, the coloring composition is suitable particularly as an ink for inkjet recording. The coloring composition of the present invention can be produced by using a lipophilic medium or an aqueous medium as the medium and dispersing the azo pigment of the present invention in the medium. Use of an aqueous medium is preferred. The coloring composition of the present invention includes an ink composition after removing the medium. The coloring composition of the present invention may contain, if desired, other additives within the range not impairing the effects of the present invention. Examples of other additives include known additives (described in JP-A-2003-306623) such as drying inhibitor (wetting agent), discoloration inhibitor, emulsion stabilizer, penetration accelerator, ultraviolet absorber, antiseptic, fungicide, pH adjusting agent, surface tension adjusting agent, defoaming agent, viscosity adjusting agent, dispersant, dispersion stabilizer, rust inhibitor and chelating agent. These various additives are generally added, in the case of an aqueous ink, directly to the ink solution and, in the case of an oil-based ink, added to the dispersion after the preparation of an azo pigment dispersion but may be added to an oil phase or an aqueous phase at the preparation.

[Ink for Inkjet Recording]

The ink for inkjet recording of the present invention is described below.

The ink for inkjet recording (hereinafter sometimes referred to as "ink") of the present invention uses the above-described dispersion and is preferably prepared by mixing a water-soluble solvent, water or the like. However, if there is no problem in particular, the above-described dispersion of the present invention may be used as it is.

The ratio of the dispersion contained in the ink of the present invention is, in view of hue, color density, reproduction, transparency and the like of the image formed on a recording medium, preferably from 1 to 100 mass %, more preferably from 3 to 20 mass %, and most preferably from 3 to 10 mass %.

The ink of the present invention preferably contains the azo pigment or azo compound of the present invention in an amount of 0.1 to 20 parts by mass, more preferably from 0.2 to 10 parts by mass, still more preferably from 1 to 10 parts by mass, per 100 parts by mass of the ink. In the ink of the present invention, other pigments may be used in combination with the pigment of the present invention. In the case of using two or more kinds of pigments, the total of pigment contents is preferably in the range above.

The ink of the present invention can be used not only for the formation of a monochromatic image but also for the formation of a full color image. For forming a full color image, a magenta tone ink, a cyan tone ink and a yellow tone ink can be used. Also, for adjusting the color tone, a black tone ink may be further used.

In the ink of the present invention, a different pigment can be used at the same time in addition to the pigment of the present invention. Examples of the applicable yellow pigment include C.I.P.Y.-74, C.I.P.Y.-128, C.I.P.Y.-155 and C.I.P.Y.-213; examples of the applicable magenta pigment include C.I.P.V.-19 and C.I.P.R.-122; and examples of the applicable cyan pigment include C.I.P.B.-15:3 and C.I.P.B.-15:4. Other than these pigments, an arbitrary pigment can be used. Examples of the applicable black color material include disazo, trisazo and tetrazo pigments and a carbon black dispersion.

Examples of the water-soluble solvent used in the ink for inkjet recording of the present invention include polyhydric alcohols, polyhydric alcohol derivatives, a nitrogen-containing solvent, alcohols, and a sulfur-containing solvent.

Specific examples of the polyhydric alcohols include ethylene glycol, diethylene glycol, propylene glycol, butylene glycol, triethylene glycol, 1,5-pentanediol, 1,2,6-hexanetriol and glycerin.

Specific examples of the polyhydric alcohol derivatives include ethylene glycol monomethyl ether, ethylene glycol monoethyl ether, ethylene glycol monobutyl ether, diethylene glycol monomethyl ether, diethylene glycol monoethyl ether, diethylene glycol monobutyl ether, propylene glycol monobutyl ether, dipropylene glycol monobutyl ether, and an ethylene oxide adduct of diglycerin.

Specific examples of the nitrogen-containing solvent include pyrrolidone, N-methyl-2-pyrrolidone, cyclohexylpyrrolidone and triethanolamine; specific examples of the alcohols include alcohols such as ethanol, isopropyl alcohol, butyl alcohol and benzyl alcohol; and specific examples of the sulfur-containing solvent include thiodiethanol, thiodiglycerol, sulfolane and dimethylsulfoxide. In addition, propylene carbonate, ethylene carbonate and the like may be used.

As for the water-soluble solvent used in the present invention, one kind of a solvent may be used alone, or two or more kinds of solvents may be mixed and used. The content of the water-soluble solvent used is from 1 to 60 mass %, preferably from 5 to 40 mass %, based on the entire ink. If the amount of the water-soluble solvent in the ink is less than 1 mass %, sufficient optical density is sometimes not obtained, whereas if it exceeds 60 mass %, the viscosity of the liquid is increased and jetting characteristics of the ink liquid becomes unstable in some cases.

Preferred physical properties of the ink for inkjet recording of the present invention are as follows. The surface tension of the ink is preferably from 20 to 60 mN/m, more preferably from 20 to 45 mN/m, still more preferably from 25 to 35 mN/m. If the surface tension is less than 20 mN/m, the liquid overflows on the nozzle surface of the recording head and the printing may not be normally performed, whereas if it exceeds 60 mN/m, penetration into the recording medium after printing proceeds slowly and the drying time may become longer.

The surface tension above was measured in an environment of 23° C. and 55% RH by using a Wilhelmy surface tensiometer similarly.

The viscosity of the ink is preferably from 1.2 to 8.0 mPa·s, more preferably from 1.5 to 6.0 mPa·s, still more preferably from 1.8 to 4.5 mPa·s. If the viscosity exceeds 8.0 mPa·s, the ejection performance sometimes deteriorates, whereas if it is less than 1.2 mPa·s, the long-term jetting performance becomes worse in some cases.

Incidentally, the above-described viscosity (including those described later) was measured using rotational viscometer Rheomat 115 (manufactured by Contraves) at 23° C. and a shear velocity of $1,400\ s^{-1}$.

In the ink, water is added within the range giving the above-described preferred surface tension and viscosity, in addition to the components above. The amount of water added is not particularly limited but is preferably from 10 to 99 mass %, more preferably from 30 to 80 mass %, based on the entire ink.

For the purpose of characteristic control such as improvement of ejection performance, polyethyleneimine, polyamines, polyvinylpyrrolidone, polyethylene glycol, cellulose derivatives such as ethyl cellulose and carboxymethyl cellulose, polysaccharides and derivates thereof, other water-soluble polymers, polymer emulsions such as acrylic polymer emulsion, polyurethane-based emulsion and hydrophilic latex, hydrophilic polymer gel, cyclodextrin, macrocyclic amines, dendrimer, crown ethers, urea and derivatives thereof, acetamide, a silicone-containing surfactant, a fluorine-containing surfactant and the like can be further used, if desired.

Also, for adjusting the electrical conductivity and pH, alkali metal compounds such as potassium hydroxide, sodium hydroxide and lithium hydroxide, nitrogen-containing compounds such as ammonium hydroxide, triethanolamine, diethanolamine, ethanolamine and 2-amino-2-methyl-1-propanol, alkaline earth metal compounds such as calcium hydroxide, acids such as sulfuric acid, hydrochloric acid and nitric acid, salts of strong acid and weak alkali, such as ammonium sulfate, and the like can be used. In addition, a pH buffering agent, an antioxidant, a fungicide, a viscosity adjusting agent, an electrical conducting agent, an ultraviolet absorber and the like may be added, if desired.

[Inkjet Recording Method, Inkjet Recording Apparatus, Ink Tank for Inkjet Recording and Recorded Material]

The inkjet recording method of the present invention is a method for forming an image on a recording medium surface by using the ink for inkjet recording of the present invention and ejecting the ink on a recording medium surface from a recording head according to recording signals.

The inkjet recording apparatus of the present invention is an apparatus for forming an image by using the ink for inkjet recording of the present invention and includes a recording head for ejecting the ink (if desired, a treated solution) on a recording medium surface, where the ink is ejected from the recording head on a recording medium surface and an image is thereby formed. Incidentally, the inkjet recording apparatus of the present invention may include an ink tank for inkjet recording (sometimes referred to as an "ink tank"), which can supply the ink to the recording head and is detachable from the body of the inkjet recording apparatus. In this case, the ink of the present invention is housed in the ink tank for inkjet recording.

As for the inkjet recording apparatus of the present invention, a normal inkjet recording apparatus equipped with a printing system capable of using the ink for inkjet recording of the present invention can be utilized, and furthermore, a heater or the like for controlling the drying of the ink or an intermediate transfer mechanism, that is, a mechanism of ejecting (printing) the ink or a treated solution on an intermediate and then transferring it on a recording medium such as paper, may be mounted, if desired.

As regards the ink tank for inkjet recording of the present invention, a conventionally known ink tank can be utilized as long as it is detachable from the inkjet recording apparatus with a recording head and has a configuration capable of supplying the ink to the recording head in the state of being loaded in the inkjet recording apparatus.

In view of the effect of improving bleed and intercolor bleed, the inkjet recording method (apparatus) of the present invention preferably employs a thermal inkjet recording system or a piezoelectric inkjet recording system.

In the case of the thermal inkjet recording system, the ink is heated at the ejection to allow for low viscosity, but since the temperature of the ink lowers on a recording medium, the viscosity is abruptly increased, and this is effective in improving bleed and intercolor bleed. On the other hand, in the case of the piezoelectric inkjet system, a liquid with high viscosity can be ejected, and the high-viscosity liquid can be kept from spreading in the paper surface direction on a recording medium, which is effective in improving bleed and intercolor bleed.

In the inkjet recording method (apparatus) of the present invention, the ink is preferably replenished (supplied) to the recording head from an ink tank (if desired, including a treated solution tank) filled with an ink solution. This ink tank is preferably a cartridge system detachable from the body of the apparatus, and by replacing this ink tank cartridge, replenishment of the ink is easily performed.

The recorded material of the present invention is obtained using the inkjet ink and is suitably obtained by employing the above-describe inkjet recording method. This recorded material can be a recorded material excellent in coloristic characteristics and durability.

EXAMPLES

The present invention is described in greater detail below by referring to Examples, but the present invention is not limited to these Examples. In Examples, "parts" indicates "parts by mass".

Example 1

The diazo component represented by formula (7) in the present invention can be synthesized by a known method (for example, the method described in *Bioorganic & Medicinal Chemistry Letter*, 14, pp-2121-2125 (2004)).

Formula (7):

[Chem. 33]

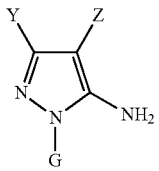

In formula (7), Y, Z and G have the same meanings as Y, Z and G in formula (1), respectively.

The coupling component represented by formula (8) in the present invention can be synthesized, for example, by the following route.

Formula (8):

[Chem. 34]

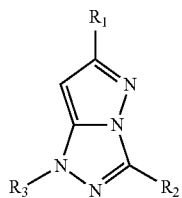

(In formula (8), $R_1$, $R_2$ and $R_3$ have the same meanings as $R_1$, $R_2$ and $R_3$ in formula (1), respectively.)

[Chem. 35]

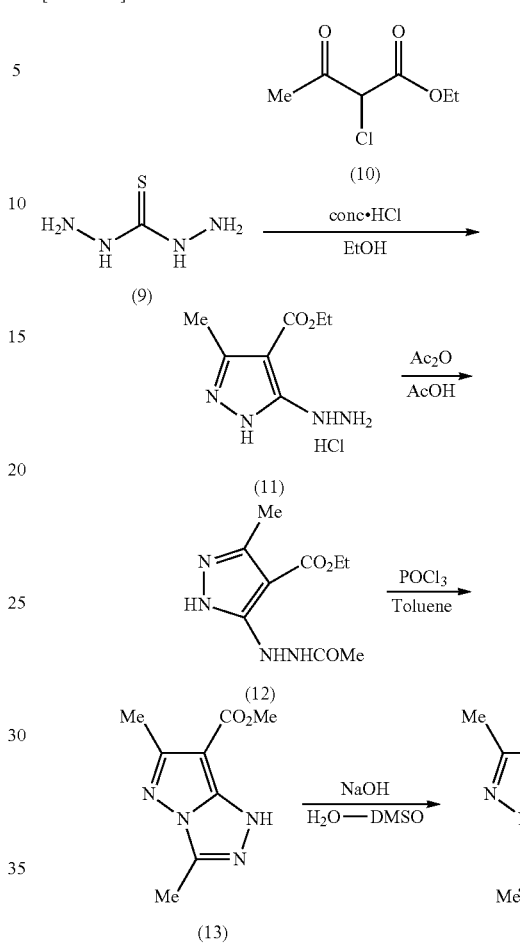

Synthesis of Compound (11):

50 Parts of thiocarbohydrazide (9) was suspended in 370 ml of ethanol at room temperature, and the suspension was heated and stirred at an internal temperature of 78° C. At the same temperature, 140 ml of 12 N hydrochloric acid was added dropwise over 30 minutes. After stirring at the same temperature for 10 minutes, 78 parts of ethyl 2-chloroacetoacetate (10) was added dropwise at the same temperature over 30 minutes. The resulting solution was stirred at the same temperature for 1 hour and then hot-filtered at the same temperature, and the precipitated solid was separated by filtration. The obtained filtrate was ice-cooled and left standing still at an internal temperature of 10° C. or less for 1 hour, and the precipitated solid was filtered, then spray-washed using 100 parts of ethyl acetate and dried at room temperature for 12 hours to obtain 33.4 parts of Compound (11) as a white solid. $^1$H NMR (300 MHz in DMSO-$d_6$; δ ppm; J Hz) 1.28 (3H, t), 2.39 (3H, s), 4.20 (2H, q), 9.7-10 (3H, br). MALDI-TOF-MS: 227.1 [M+H$^+$].

Synthesis of Compound (12):

23.3 Parts of Compound (11) was suspended in 70 parts of acetic acid at room temperature, and the suspension was heated and stirred at an internal temperature of 80° C. At the same temperature, 10 ml of acetic anhydride was added dropwise over 3 minutes. The resulting solution was stirred at the same temperature for 1 hour and then ice-cooled to an internal temperature of 10° C., and the precipitated solid was filtered, spray-washed using 20 parts of acetic acid and dried at room temperature for 12 hours under reduced pressure to obtain 22.4 g of Compound (12) as a white solid. $^1$H NMR (300 MHz in DMSO-$d_6$; δ ppm; J Hz) 1.27 (3H, t), 1.84 (3H, s), 2.31 (3H, s), 4.20 (2H, q), 9.90 (1H, s). MALDI-TOF-MS: 155.1 [M+H$^+$].

Synthesis of Compound (13):

14.3 Parts of Compound (12) was suspended in 430 parts of toluene at room temperature, and the suspension was heated and stirred at an internal temperature of 110° C. At the same temperature, 11.8 ml of phosphorus oxychloride was added dropwise over 15 minutes. After stirring at the same temperature for 1 hour, 4 ml of phosphorus oxychloride was further added dropwise over 10 minutes at the same temperature. The resulting solution was further stirred at the same temperature for 1 hour, then cooled to room temperature and added little by little to 800 parts of water while keeping the internal temperature at 20 to 25° C., and after the whole was added to water, potassium carbonate was added little by little while keeping the temperature at 20 to 25° C. until the pH became 7. The resulting solution adjusted to a pH of 7 was stirred at room temperature for 30 minutes and then subjected to liquid separation operation. The aqueous layer was extracted with 300 parts of ethyl acetate twice, and the combined oil layer was washed with 100 parts of water. The oil layer was dried over anhydrous sodium sulfate. Sodium sulfate was separated by filtration, and then the solvent was removed by distillation under reduced pressure to obtain 10.0 parts of Compound (13) as a brown solid. $^1$H NMR (300 MHz in DMSO-$d_6$; δ ppm; J Hz) 1.29 (3H, t), 2.43 (3H, s), 2.48 (3H, s), 4.20 (2H, q). MALDI-TOF-MS: 209.1 [M+H$^+$].

Synthesis of Compound (14):

22 Parts of Compound (13) was suspended in 180 parts of dimethylsulfoxide at room temperature, and the suspension was stirred at room temperature. Nitrogen gas was blown thereinto at the same temperature for 30 minutes and after deaeration, a solution separately prepared by dissolving 42 parts of sodium hydroxide in 88 parts of water was added dropwise over 30 minutes. After the dropwise addition, the resulting solution was heated and stirred at an internal temperature of 100° C. for 2 hours, and the inner temperature was lowered to 10° C. or less by ice cooling. Thereafter, the solution was poured in 1,000 parts of cool water at an internal temperature of 5° C. and then neutralized to a pH of 7 by adding 12 N hydrochloric acid. The precipitated crystal was filtered and spray-washed using 200 parts of water and 100 parts of ethyl acetate to obtain 9.1 parts of Compound (14) as a brown solid. $^1$H NMR (300 MHz in DMSO-$d_6$; δ ppm; J Hz) 2.23 (3H, s), 2.44 (3H, s), 5.49 (1H, s). MALDI-TOF-MS: 137.0 [M+H$^+$].

Example 2

Specific Compound (2)-1

Specific Compound (2)-1 was synthesized by the following route.

[Chem. 36]

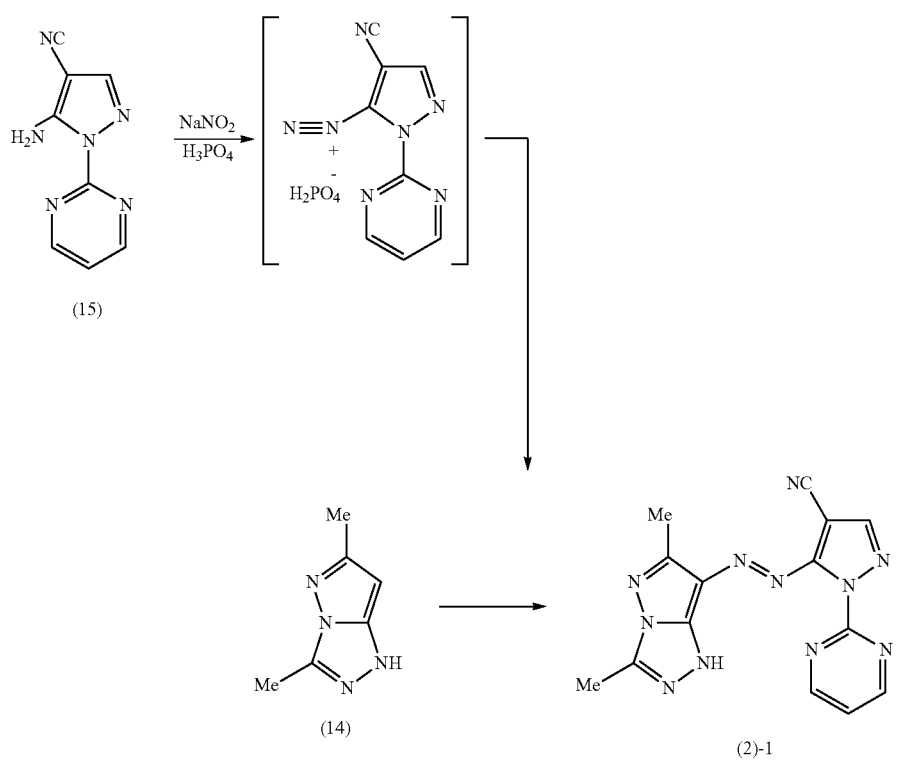

Synthesis of Pigment (2)-1:

6.6 Parts of Compound (15) was added to 79 parts of phosphoric acid at room temperature and dissolved by heating at an internal temperature of 60° C., and the resulting solution was kept at an internal temperature of −5 to 0° C. by ice cooling. 3.0 Parts of sodium nitrite was added in parts while keeping the internal temperature at 5° C. or less, and the mixture was stirred at the same temperature for 1 hour to obtain a diazonium salt solution. Separately, 4 parts of Compound (14) was added to 200 parts of methanol to prepare a suspension, and the suspension was kept at an internal temperature of 5° C. or less by ice cooling. The diazonium salt solution obtained above was gradually added thereto while keeping the internal temperature at 5° C. or less. The mixture was stirred at the same temperature for 1 hour and after removing the ice bath, stirred at room temperature for 1 hour. The precipitated crystal was separated by filtration, spray-washed with 200 parts of methanol and further thoroughly spray-washed with water. The obtained crystal was added without drying to 200 parts of methanol and 100 parts of water, and the mixture was heated with stirring at an internal temperature of 65° C. for 3 hours. The resulting solution was stirred under air cooling for 1 hour and thereby cooled to room temperature, and the precipitated crystal was separated by filtration and washed with 200 parts of methanol. The crystal was dried at room temperature for 12 hours to obtain 7.3 parts of Pigment (2)-1 of the present invention. Yield: 74.5%. FIG. 1 shows the infrared absorption spectrum (KBr method) of Pigment (2)-1.

Example 3

Specific Compound (2)-43

Specific Compound (2)-43 was synthesized by the following route.

[Chem. 37]

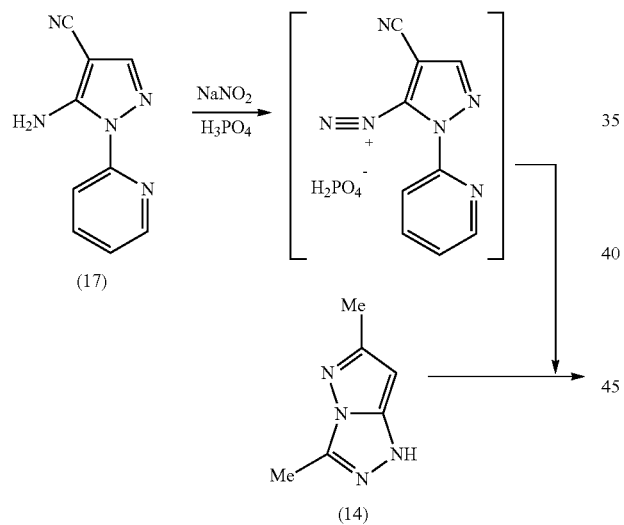

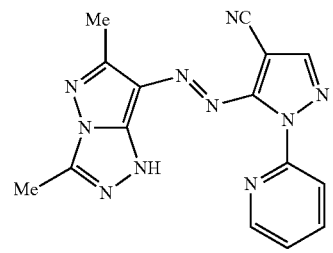

(2)-43

Figure 2:
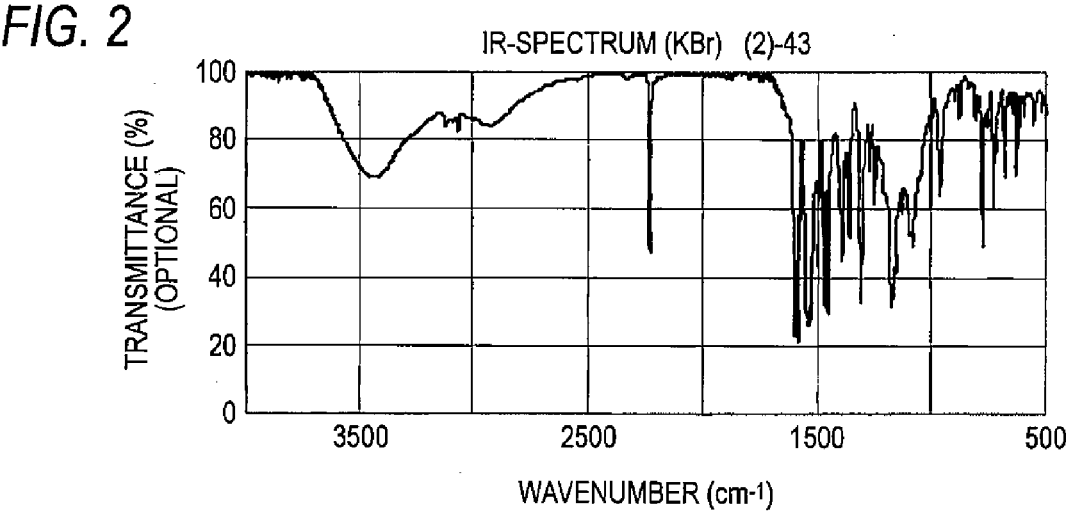
FIG. 2 The infrared absorption spectrum of Azo Pigment (2)-43 obtained in Example 3.

Synthesis of Pigment (2)-43:

13.7 Parts of Compound (17) was added to 164 parts of phosphoric acid at room temperature and dissolved by heating at an internal temperature of 60° C., and the resulting solution was kept at an internal temperature of −5 to 0° C. by ice cooling. 5.6 Parts of sodium nitrite was added in parts while keeping the internal temperature at 5° C. or less, and the mixture was stirred at the same temperature for 1 hour to obtain a diazonium salt solution. Separately, 9.0 parts of Compound (14) was added to 600 parts of methanol to prepare a suspension, and the suspension was kept at an internal temperature of 5° C. or less by ice cooling. The diazonium salt solution obtained above was gradually added thereto while keeping the internal temperature at 5° C. or less, and the mixture was stirred at the same temperature for 1 hour and after removing the ice bath, stirred at room temperature for 1 hour. The precipitated crystal was separated by filtration, spray-washed with 500 parts of methanol and further thoroughly spray-washed with water. The obtained crystal was added without drying to 200 parts of methanol and 100 parts of water, and the mixture was heated with stirring at an internal temperature of 65° C. for 3 hours. The resulting solution was stirred under air cooling for 1 hour and thereby cooled to room temperature, and the precipitated crystal was separated by filtration and washed with 200 parts of methanol. The crystal was dried at room temperature for 12 hours to obtain 17.9 parts of Pigment (2)-43 of the present invention. Yield: 81.4%. FIG. 2 shows the infrared absorption spectrum (KBr method) of Pigment (2)-43.

Example 4

Specific Compound (1)-33

Specific Compound (1)-33 was synthesized by the following route.

[Chem. 38]

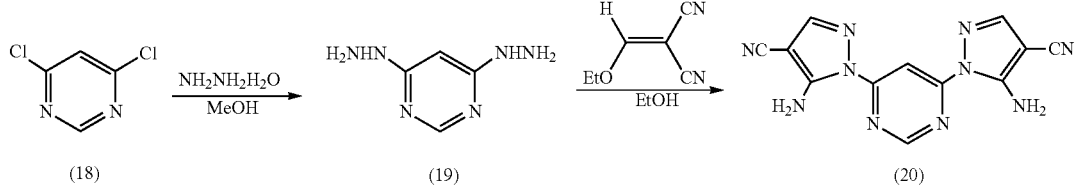

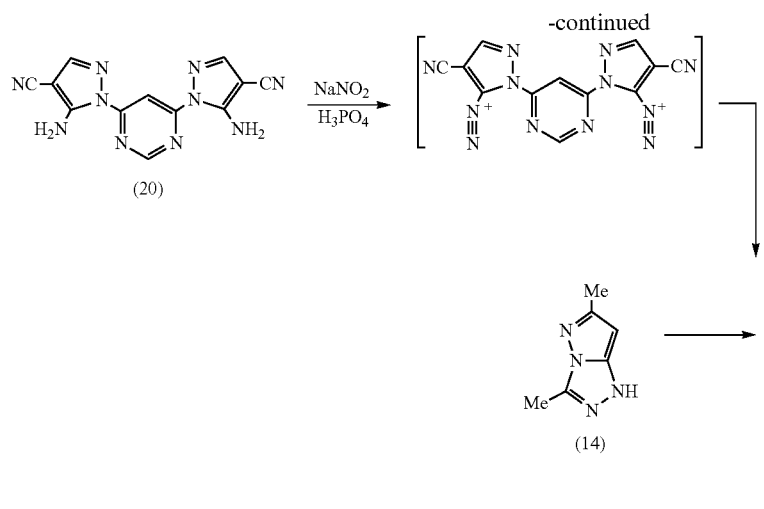

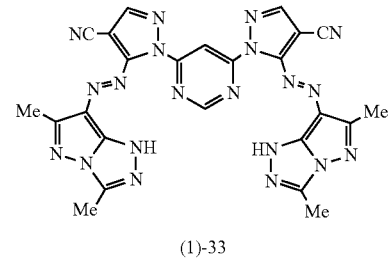

Synthesis of Intermediate (19):

Methanol (298 mL) was added to 387 mL (7.98 mol) of hydrazine monohydrate, and the mixture was cooled to 10° C. (internal temperature). To this mixed solution, 149 g (1.00 mol) of 4,6-dichloropyrimidine was gradually added (internal temperature: 20° C. or less), and the ice bath was removed. The temperature was raised to room temperature, and the mixture was stirred at the same temperature for 30 minutes, then further heated to raise the temperature to an internal temperature of 60° C., and stirred at the same temperature for 5 hours. After the completion of reaction, 750 mL of water was added, and the resulting solution was then cooled by ice cooling to an internal temperature of 8° C. The precipitated crystal was collected by filtration, spray-washed with water, further spray-washed with isopropanol and dried at room temperature for 36 hours to obtain 119 g of Intermediate (19) (white powder, yield: 84.5%). The NMR measurement results of Intermediate (19) obtained are as follows. $^1$H NMR (300 MHz in DMSO-$d_6$; δ ppm; J Hz) 7.80 (1H, s), 7.52 (2H, s), 5.98 (1H, s), 4.13 (4H, s).

Synthesis of Intermediate (20):

Ethanol (50 mL) was added to 10 g (71.3 mmol) of Intermediate (19) and after stirring at room temperature. 21.8 g (178 mmol) of ethoxymethylene malononitrile was added to this suspension. Aqueous 12 M hydrochloric acid was added dropwise at the same temperature to adjust the pH to 3, and the resulting mixture was heated to an internal temperature of 80° C. and stirred at the same temperature for 1.5 hours. After the completion of reaction, the reaction solution was cooled to room temperature, and the precipitated crystal was separated by filtration and spray-washed with 30 ml of water and 30 ml of isopropanol. The obtained crystal was dried at 60° C. under reduced pressure to obtain 18.8 g of Intermediate (20) (gray powder, yield: 90.3%). The NMR measurement results of Intermediate (20) obtained are as follows. $^1$H NMR (300 MHz in DMSO-$d_6$; δ ppm; J Hz) 8.94 (1H, s), 8.35 (4H, s), 8.03 (2H, s), 8.01 (1H, s).

Synthesis of Pigment (1)-33:

40 Parts of phosphoric acid and 10 parts of sulfuric acid were added to 2 parts of Intermediate (20), and the mixture was heated to an internal temperature of 60° C. and stirred for 30 minutes. The resulting suspension was kept at an internal temperature of 3 to 5° C. by cooling, and 1.2 parts of sodium nitrite was added. The mixture was stirred at the same temperature for 2 hours to obtain a diazonium salt solution, and Compound (14) in the powder form was gradually added thereto while keeping the internal temperature at 5° C. or less. This mixture was stirred at the same temperature for 1.5 hours and after removing the ice bath, stirred at room temperature for 30 minutes, and 60 ml of methanol was added thereto. After stirring for 30 minutes, the reaction solution was poured in 200 ml of water, and the resulting solution was stirred at room temperature for 30 minutes. The precipitated crystal was collected by filtration and spray-washed with 100 ml of water and 50 ml of methanol. Without drying the obtained crystal, 20 ml of methanol and 20 ml of water were added thereto. The mixture was heated with stirring at an internal temperature of 65° C. for 3 hours, then stirred under air cooling for 1 hour and cooled to room temperature, and the precipitated crystal was separated by filtration and washed with 30 parts of methanol. The crystal was dried at room temperature for 12 hours to obtain 2.8 parts of Pigment (1)-33 of the present invention. Yield: 69.2%.

Comparative Example 1

Comparative Compound (17)

Comparative Compound (17) was synthesized by the following route.

[Chem. 39]

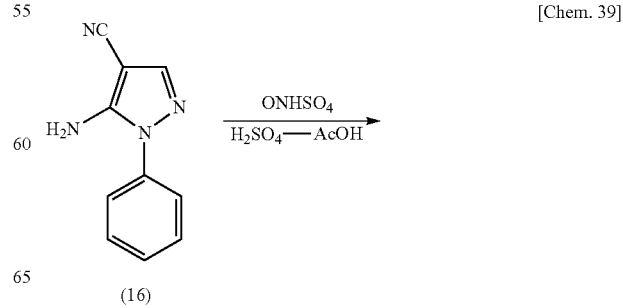

-continued

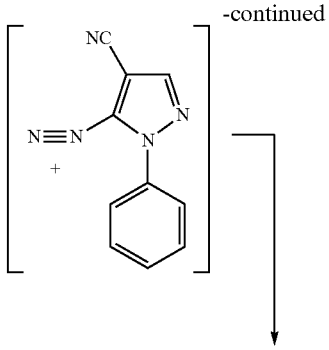

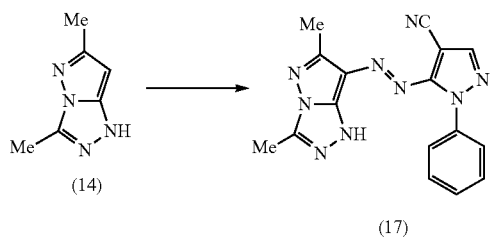

Figure 3:
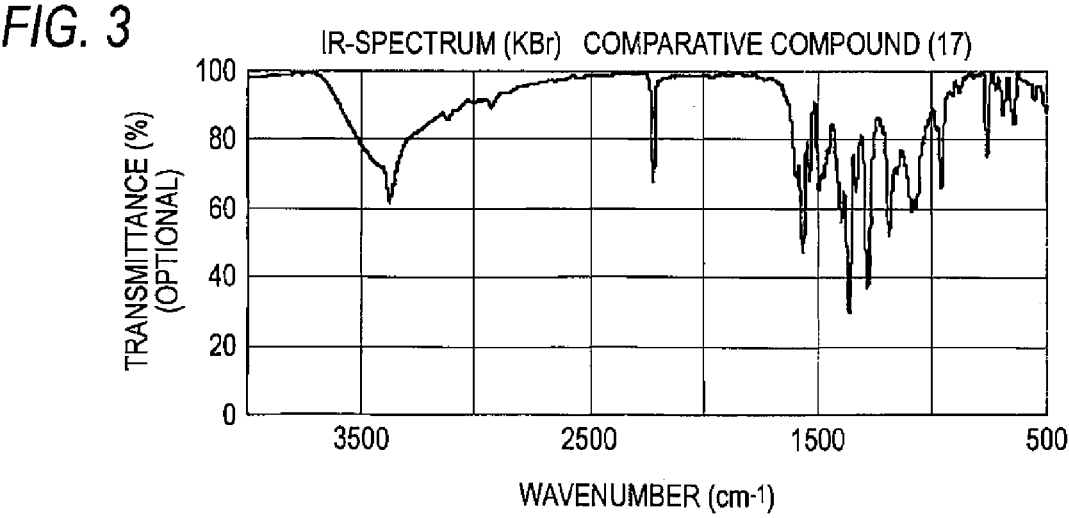
FIG. 3 The infrared absorption spectrum of Azo Compound (17) obtained in Comparative Example 1.

Synthesis of Comparative Compound (17):

8.4 Parts of 43 wt % nitrosylsulfuric acid was dissolved in 17 parts of concentrated sulfuric acid and 32 parts of acetic acid, and this solution was kept at an internal temperature of 0 to 5° C. by ice cooling. 3.0 Parts of Compound (16) was added in parts while keeping the internal temperature at 5° C. or less, and the mixture was stirred at the same temperature for 1 hours to obtain a diazonium salt solution. Separately, 2 parts of Compound (14) was added to 80 parts of methanol to prepare a suspension, and the suspension was kept at an internal temperature of 5° C. or less by ice cooling. The diazonium salt solution obtained above was gradually added thereto while keeping at 5° C. or less, and the resulting solution was stirred at the same temperature for 1 hours and after removing the ice bath, stirred at room temperature for 1 hour. The precipitated crystal was separated by filtration, spray washed with 80 parts of methanol and further thoroughly spray-washed with water. The obtained crystal was added without drying to 80 parts of methanol and 40 parts of water, and the mixture was heated with stirring at an internal temperature of 65° C. for 3 hours. The resulting solution was stirred under air cooling for 1 hour and cooled to room temperature, and the precipitated crystal was separated by filtration and washed with 30 parts of methanol. The crystal was dried at room temperature for 12 hours to obtain 3.7 parts of Comparative Compound (17). Yield: 75.5%. FIG. 3 shows the infrared absorption spectrum (KBr method) of Comparative Compound (17).

Example 5

2.5 Parts of Pigment (2)-1 synthesized in Example 2, 0.5 parts of sodium oleate, 5 parts of glycerin and 42 parts of water were mixed, and the mixture was dispersed together with 100 parts of zirconium beads having a diameter of 0.1 mm by using a planetary ball mill at 300 rpm for 6 hours. After the completion of dispersion, zirconia beads were separated to obtain yellow Pigment Dispersion 1.

Example 6

Pigment Dispersion 2 was obtained in the same manner as in Example 5 except for using Azo Pigment (2)-43 of the present invention in place of Pigment (2)-1 used in Example 5.

Example 7

Pigment Dispersion 3 was obtained in the same manner as in Example 5 except for using Azo Pigment (1)-33 of the present invention in place of Pigment (2)-1 used in Example 5.

Comparative Example 2

The same operation as in Example 5 was performed except for using Comparative Compound (17) in place of Pigment (2)-1 used in Example 5. After the dispersion operation for 6 hours, a pigment dispersion was not obtained, and the mixture was gelled.

Comparative Example 3

Yellow Pigment Dispersion 1 was obtained in the same manner as in Example 5 except for using C.I. Pigment Yellow 155 (INKJET YELLOW 4G VP2532 produced by Clariant) in place of Pigment (2)-1 used in Example 5.
<Evaluation of Hue>

The hue was evaluated by observing with an eye the chromaticity of the coated material obtained above, and rated ○ (good) when little, tinting with red and high clearness were recognized, rated Δ when either one was lacking, and rated X (bad) when both were lacking. The results are shown in Table 1.
<Evaluation of Light Fastness>

The coated material having an image density of 1.0 used for the evaluation of hue was irradiated with xenon light (170,000 Lux.; in the presence of a cut filter for 325 nm or less) for 14 days by using a fade meter and the color density before and after the xenon irradiation was measured using a reflection densitometer. Based on the colorant residual ratio [density after irradiation/density before irradiation)×100%], Pigment Dispersions 1, 2 and 3 and Comparative Pigment Dispersion 1 were evaluated and rated ○ when the residual ratio was 60% or more, rated Δ when from 50% to less than 60%, and rated X when less than 50%. The results are shown in Table 1.

The pigment dispersions obtained each was coated on Plain Paper 4024 produced by Fuji Xerox Co., Ltd. by using a No. 3 bar coater and when the coated material obtained was evaluated for light fastness in the same manner as the photomat paper, the same results as those of the photomat paper were obtained. The results are shown in Table 1.
<Dispersibility>

Pigment Dispersions 1, 2 and 3, Comparative Compound (17) and Comparative Pigment Dispersion 1 were evaluated by mixing 2.5 parts of pigment, 0.5 parts of sodium oleate, 5 parts of glycerin and 42 parts of water and dispersing the mixture together with 100 parts of zirconium beads having a diameter of 0.1 mm in a planetary ball mill at 300 rpm for 6 hours, and rated A when the pigment could be dispersed to a sufficiently small particle diameter without causing gelling and rated B when failed in dispersing in this way. The results are shown in Table 1.

TABLE 1

| | Hue | Light Fastness (photomat paper) | Light Fastness (plain paper) | Dispersibility |
|---|---|---|---|---|
| Pigment Dispersion 1 | ○ | ○ | ○ | ○ |
| Pigment Dispersion 2 | ○ | ○ | ○ | ○ |
| Pigment Dispersion 3 | ○ | ○ | ○ | ○ |
| Comparative Compound (17) | — | — | — | X |
| Comparative Pigment Dispersion 1 | X | Δ | Δ | ○ |

It is seen from the results of Table 1 that the pigment dispersion using the pigment of the present invention is excellent in hue and light fastness and exhibits excellent dispersibility.

INDUSTRIAL APPLICABILITY

The pigment dispersion can be used, for example, in an ink for printing such as inkjet recording, a color toner for electrophotography, a color filter for a display such as LCD and PDP or an imaging device such as CCD, a coating material, and a colored plastic.

While the invention has been described in detail and with reference to specific embodiments thereof, it will be apparent to one skilled in the art that various changes and modifications can be made therein without departing from the spirit and scope thereof.

This application is based on Japanese Patent Application (Japanese Patent Application No. 2008-058713) filed on Mar. 7, 2008 and Japanese Patent Application (Japanese Patent Application No. 2009-026195) filed on Feb. 6, 2009, the contents of which are incorporated herein by way of reference.

The invention claimed is:

1. An azo pigment represented by the following formula (1), its tautomer, or a salt or hydrate thereof:

Formula (1):

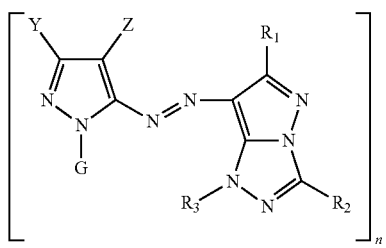

(wherein $R_1$, $R_2$, $R_3$, Y, Z and G each independently represents a hydrogen atom or a substituent; n represents and integer of 2 to 4; and the formula represents a dimer through $R_1$, $R_2$, $R_3$, Y, Z or G when n is 2, represents a trimer through $R_1$, $R_2$, $R_3$, Y, Z or G when n is 3, and represents a tetramer through $R_1$, $R_2$, $R_3$, Y, Z or G when n is 4).

2. An azo pigment represented by the following formula (2), its tautomer, or a salt or hydrate thereof:

Formula (2):

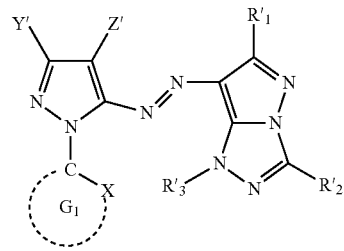

(wherein $R'_1$, $R'_2$ and Y' each independently represents a hydrogen atom, a linear or branched alkyl group having a carbon number of 1 to 4, an alkenyl group having a carbon number of 2 to 4, an alkynyl group having a carbon number of 2 to 4, an acyl group having a carbon number of 1 to 5, an aralkyl group having a carbon number of 7 to 9, a 5- to 8-membered saturated or unsaturated hydrocarbon ring group, or a 5- to 8-membered saturated or unsaturated heterocyclic group; $R'_3$ represents a hydrogen atom or a monovalent substituent; Z' represents an electron-withdrawing group having a Hammett's σp value of 0.2 or more; X represents a heteroatom at the position adjacent to the carbon atom bonded to the pyrazole ring; $G_1$ represents an atomic group for forming a 5- to 8-membered saturated or unsaturated heterocyclic ring; when any one of $R'_1$, $R'_2$, $R'_3$, Y' and $G_1$ represents a 5- to 8-membered saturated or unsaturated heterocyclic ring, the ring is a monocyclic ring or a condensed ring; and when any one of $R'_1$, $R'_2$, $R'_3$, Y' and $G_1$ represents a 5-membered unsaturated heterocyclic ring, the ring contains two or more nitrogen atoms therein).

3. The azo pigment, its tautomer or a salt or hydrate thereof according to claim 2, wherein X in formula (2) is a nitrogen atom.

4. The azo pigment, its tautomer or a salt or hydrate thereof according to claim 2, wherein $G_1$ in formula (2) is any one selected from the group of substituents represented by the following formula (3)-1 to (3)-6:

Formula (3):

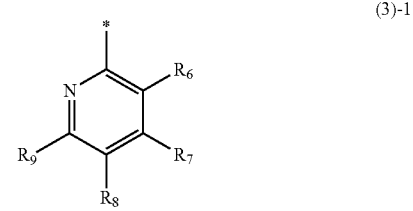

(3)-1

-continued (3)-2
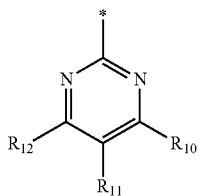

(3)-3
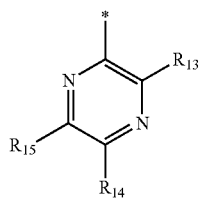

(3)-4
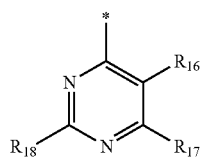

(3)-5
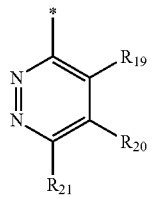

(3)-6
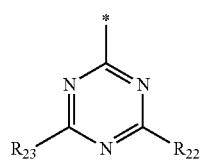

(wherein $R_6$ to $R_{23}$ each independently represents a hydrogen atom or a substituent, and $R_6$ to $R_{21}$ may combine with each other to form a ring).

5. The azo pigment, its tautomer or a salt or hydrate thereof according to claim 1, wherein the azo pigment represented by formula (1) is an azo pigment represented by the following formula (4):

Formula (4):

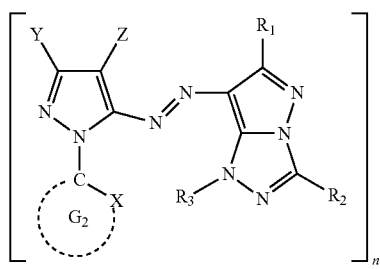

(wherein n, $R_1$, $R_2$, $R_3$, Y and Z each independently has the same meaning as n, $R_1$, $R_2$, $R_3$, Y or Z in formula (1); X represents a heteroatom at the position adjacent to the carbon atom bonded to the pyrazole ring; $G_2$ represents an atomic group for forming a 5- to 8-membered saturated or unsaturated heterocyclic ring; the formula represents a dimer through $R_1$, $R_2$, $R_3$, Y, Z or $G_2$ when n is 2, represents a trimer through $R_1$, $R_2$, $R_3$, Z or $G_2$ when n is 3, and represents a tetramer through $R_1$, $R_2$, $R_3$, Y, Z or $G_2$ when n is 4; and when any one of $R_1$, $R_2$, $R_3$, Y and $G_2$ represents a 5- to 8-membered saturated or unsaturated heterocyclic ring, the ring is a monocyclic ring or a condensed ring).

6. The azo pigment, its tautomer or a salt or hydrate thereof according to claim 5, wherein X in formula (4) is a nitrogen atom.

7. The azo pigment, its tautomer or a salt or hydrate thereof according to claim 5, wherein $G_2$ in formula (4) is any one group selected from the group of monovalent to trivalent substituents represented by (3)-1 to (3)-6 in the following formula (3):

Formula (3):

(3)-1

(3)-2
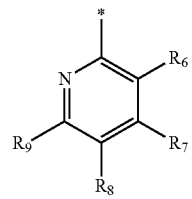

(3)-3
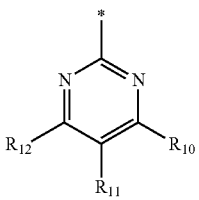

(3)-4
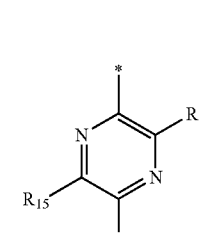

(3)-5
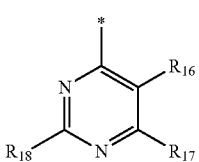

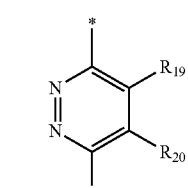

-continued (3)-6

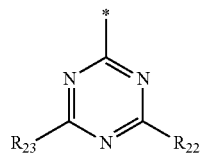

(wherein $R_6$ to $R_{23}$ each independently represents a hydrogen atom or a substituent, and $R_6$ to $R_{21}$ may combine with each other to form a ring).

8. An azo compound represented by the following formula (2):

Formula (2):

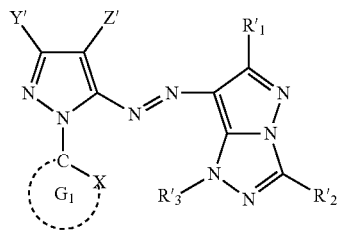

(wherein $R'_1$, $R'_2$ and $Y'$ each independently represents a hydrogen atom, a linear or branched alkyl group having a carbon number of 1 to 4, an alkenyl group having a carbon number of 2 to 4, an alkynyl group having a carbon number of 2 to 4, an acyl group having a carbon number of 1 to 5, an aralkyl group having a carbon number of 7 to 9, a 5- to 8-membered saturated or unsaturated hydrocarbon ring group, or a 5- to 8-membered saturated or unsaturated heterocyclic group; $R'_3$ represents a hydrogen atom or a monovalent substituent; $Z'$ represents an electron-withdrawing group having a Hammett's σp value of 0.2 or more; X represents a heteroatom at the position adjacent to the carbon atom bonded to the pyrazole ring; $G_1$ represents an atomic group for forming a 5- to 8-membered saturated or unsaturated heterocyclic ring; when any one of $R'_1$, $R'_2$, $R'_3$, $Y'$ and $G_1$ represents a 5- to 8-membered saturated or unsaturated heterocyclic ring, the ring is a monocyclic ring or a condensed ring; and when any one of $R'_1$, $R'_2$, $R'_3$, $Y'$ and $G_1$ represents a 5-membered unsaturated heterocyclic ring, the ring contains two or more nitrogen atoms therein).

9. The azo compound according to claim 8, wherein $G_1$ in formula (2) is any one selected from the group of substituents represented by the following formula (3)-1 to (3)-6:

Formula (3):

(3)-1

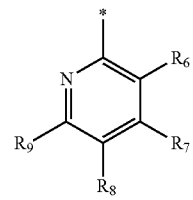

(3)-2

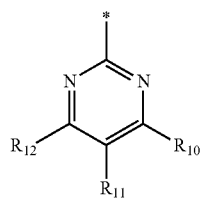

(3)-3

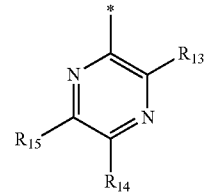

(3)-4

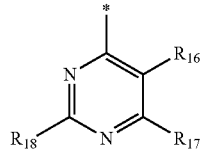

(3)-5

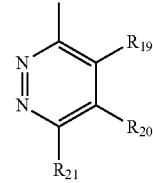

(3)-6

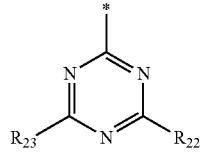

(wherein $R_6$ to $R_{23}$ each independently represents a hydrogen atom or a substituent, and $R_6$ to $R_{21}$ may combine with each other to form a ring).

10. An azo compound represented by the following formula (4):

Formula (4):

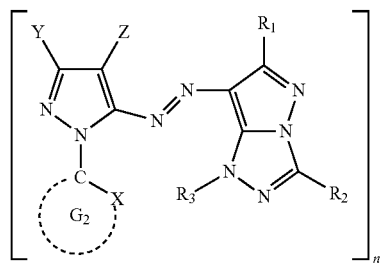

(wherein $R_1$, $R_2$, $R_3$, Y and Z each independently represents a hydrogen atom or a substituent; n represents an integer of 2 to 4; X represents a heteroatom at the position adjacent to the carbon atom bonded to the pyrazole ring; $G_2$ represents an atomic group for forming a 5-to 8-membered saturated or unsaturated heterocyclic ring; the formula represents a dimer through $R_1$, $R_2$, $R_3$, Y, Z or $G_2$ when n is 2, represents a trimer through $R_1, R_2, R_3$, Y, Z or $G_2$ when n is 3, and represents a tetramer through $R_1, R_2, R_3$, Y, Z or $G_2$ when n is 4; and when any one of $R_1, R_2, R_3$, Y and $G_2$ represents a 5- to 8-membered saturated or unsaturated heterocyclic ring, the ring is a monocyclic ring or a condensed ring).

11. The azo compound according to claim 10, wherein $G_2$ in formula (4) is any one group selected from the group of monovalent to trivalent substituents represented by (3)-1 to (3)-6 in the following formula (3):

Formula (3):

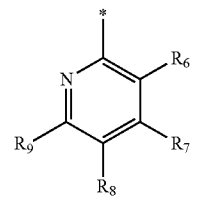
(3)-1

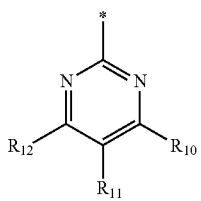
(3)-2

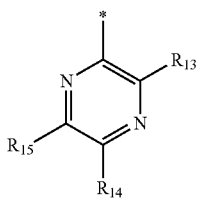
(3)-3

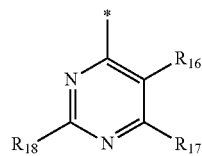
(3)-4

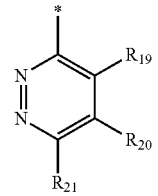
(3)-5

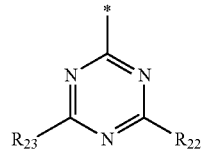
(3)-6

(wherein $R_6$ to $R_{23}$ each independently represents a hydrogen atom or a substituent, and $R_6$ to $R_{21}$ may combine with each other to form a ring).

12. A dispersion comprising at least one member of the azo pigment, its tautomer or a salt or hydrate thereof according to claim 1 or the azo compound according to claim 8.

13. A coloring composition comprising the dispersion according to claim 12.

14. An ink for inkjet recording, comprising the dispersion according to claim 12.

15. An ink tank for inkjet recording, comprising the ink for inkjet recording according to claim 14.

16. An inkjet recording method, using the ink for inkjet recording according to claim 14.

17. A recorded material obtained using the ink for inkjet recording according to claim 14.

* * * * *